US008067207B2

(12) United States Patent
Bergeron et al.

(10) Patent No.: US 8,067,207 B2
(45) Date of Patent: Nov. 29, 2011

(54) SPECIES-SPECIFIC, GENUS-SPECIFIC AND UNIVERSAL DNA PROBES AND AMPLIFICATION PRIMERS TO RAPIDLY DETECT AND IDENTIFY COMMON BACTERIAL AND FUNGAL PATHOGENS AND ASSOCIATED ANTIBIOTIC RESISTANCE GENES FROM CLINICAL SPECIMENS FOR DIAGNOSIS IN MICROBIOLOGY LABORATORIES

(75) Inventors: Michel G. Bergeron, Sillery (CA); François J. Picard, Cap-Rouge (CA); Marc Ouellette, Sillery (CA); Paul H. Roy, Loretteville (CA)

(73) Assignee: Geneohm Sciences Canada Inc., San Diego, CA (US)

( * ) Notice: Subject to any disclaimer, the term of this patent is extended or adjusted under 35 U.S.C. 154(b) by 862 days.

(21) Appl. No.: 11/416,501

(22) Filed: May 2, 2006

(65) Prior Publication Data

US 2006/0263810 A1 Nov. 23, 2006

Related U.S. Application Data

(63) Continuation of application No. 10/753,169, filed on Jan. 7, 2004, which is a continuation of application No. 09/989,643, filed on Nov. 20, 2001, now abandoned, which is a continuation of application No. 09/297,539, filed as application No. PCT/CA97/00829 on Nov. 4, 1997, now abandoned.

(51) Int. Cl.

| | |
|---|---|
| ***C12P 19/34*** | (2006.01) |
| ***C12Q 1/68*** | (2006.01) |
| ***G01N 33/53*** | (2006.01) |
| ***C07H 21/02*** | (2006.01) |
| ***C07H 21/04*** | (2006.01) |

(52) U.S. Cl. ........... 435/91.2; 435/6; 435/7.2; 435/91.1; 536/23.1; 536/23.7; 536/23.74; 536/24.3; 536/24.33

(58) Field of Classification Search ............. 435/6, 91.1, 435/91.2, 183, 7.2; 436/94, 501; 536/23.1, 536/24.3, 24.33, 25.3, 23.7, 23.74

See application file for complete search history.

(56) References Cited

U.S. PATENT DOCUMENTS

| | | | |
|---|---|---|---|
| 4,816,389 | A | 3/1989 | Sonsonetti et al. |
| 5,030,556 | A | 7/1991 | Beaulieu et al. |
| 5,041,372 | A | 8/1991 | Lampel et al. |
| 5,084,565 | A | 1/1992 | Parodos et al. |
| 5,089,386 | A | 2/1992 | Stackebrandt et al. |
| 5,162,199 | A | 11/1992 | Stern et al. |
| 5,232,831 | A | 8/1993 | Milliman et al. |
| 5,292,874 | A | 3/1994 | Milliman |
| 5,298,392 | A | 3/1994 | Atlas et al. |
| 5,334,501 | A | 8/1994 | Adams et al. |
| 5,389,513 | A | 2/1995 | Baquero et al. |
| 5,401,631 | A | 3/1995 | Lane et al. |
| 5,437,978 | A | 8/1995 | Ubikata et al. |
| 5,472,843 | A | 12/1995 | Milliman |
| 5,476,929 | A | 12/1995 | Briles et al. |
| 5,523,205 | A | 6/1996 | Cossart et al. |
| 5,523,217 | A | 6/1996 | Lupski et al. |
| 5,541,308 | A | 7/1996 | Hogan et al. |
| 5,574,145 | A | 11/1996 | Barry et al. |
| 5,595,874 | A | 1/1997 | Hogan et al. |
| 5,599,665 | A | 2/1997 | Barbieri et al. |
| 5,627,275 | A | 5/1997 | Roll |
| 5,652,102 | A | 7/1997 | Fratamico et al. |
| 5,708,160 | A | 1/1998 | Goh et al. |
| 5,866,336 | A | 2/1999 | Nazarenko et al. |
| 5,994,066 | A | 11/1999 | Bergeron et al. |
| 6,001,564 | A | 12/1999 | Bergeron et al. |
| 6,037,130 | A | 3/2000 | Tyagi et al. |
| 6,582,908 | B2 | 6/2003 | Fodor et al. |
| 6,610,836 | B1 | 8/2003 | Breton et al. |
| 2003/0180733 | A1 | 9/2003 | Bergeron et al. |
| 2004/0185478 | A1 | 9/2004 | Bergeron et al. |
| 2005/0042606 | A9 | 2/2005 | Bergeron et al. |
| 2007/0009947 | A1 | 1/2007 | Bergeron et al. |
| 2007/0105129 | A1 | 5/2007 | Bergeron et al. |
| 2009/0047671 | A1 | 2/2009 | Bergeron et al. |
| 2009/0053702 | A1 | 2/2009 | Bergeron et al. |
| 2009/0053703 | A1 | 2/2009 | Bergeron et al. |
| 2009/0068641 | A1 | 3/2009 | Bergeron et al. |
| 2010/0267012 | A1 | 10/2010 | Bergeron et al. |

FOREIGN PATENT DOCUMENTS

| | | |
|---|---|---|
| CA | 2052822 | 4/1992 |
| EP | 0 133 288 | 2/1985 |
| EP | 0 133 671 | 3/1985 |
| EP | 0 272 009 | 6/1988 |
| EP | 0 277 237 | 8/1988 |
| EP | 0 297 291 | 1/1989 |
| EP | 0 377 896 | 10/1989 |
| EP | 0 364 255 | 4/1990 |
| EP | 0 438 115 | 7/1991 |
| EP | 0 466 251 | 1/1992 |
| EP | 0 527 628 | 2/1993 |

(Continued)

OTHER PUBLICATIONS

Aminov et al. (1996), Cloning, sequencing and complementation analysis of the *rec*A gene from *Prevotella ruminicola*, FEMS Microbiology Letters 144:53-59. An, G. and Friesen, J.D. (1980), The nucleotide sequence of tufB and four nearby tRNA structural genes of *Escherichia coli*, Gene 12:33-39.

Andersson, Siv. G.E. (1995), Unusual organization of the rRNA genes in *Rickettsia prowazekii*, Journal of Bacteriology 177(14):4171-4175.

Berg et al. (1996), Development of an amplification and hybridization assay for the specific and sensitive detection of *Mycoplasma fermentans* DNA, Molecular and Cellular Probes 10:7-14.

Birnboim, H.C. and Doly, J. (1979), A rapid alkaline extraction procedure for screening recombinant plasmid DNA, Nucleic Acids Research 7(4):1513-1523.

(Continued)

*Primary Examiner* — Frank W Lu

(74) *Attorney, Agent, or Firm* — Knobbe Martens Olson & Bear LLP

(57) ABSTRACT

Embodiments disclosed herein relate to methods and compositions for species-specific detection of bacterial and fungal nucleic acids and nucleic acids of antibiotic resistance genes.

10 Claims, No Drawings

FOREIGN PATENT DOCUMENTS

| | | |
|---|---|---|
| EP | 0 577 523 | 1/1994 |
| EP | 0 630 973 A2 | 12/1994 |
| EP | 0 652 291 | 5/1995 |
| EP | 0 695 803 | 2/1996 |
| EP | 0 761 815 | 3/1997 |
| EP | 0 786 519 | 7/1997 |
| EP | 0 804 616 | 11/1997 |
| FR | 2584419 | 1/1987 |
| FR | 2599743 | 12/1987 |
| FR | 2636075 | 3/1990 |
| FR | 2685334 | 6/1993 |
| FR | 2686604 A1 | 7/1993 |
| FR | 2699539 | 6/1994 |
| JP | 6-54700 | 3/1994 |
| JP | 6-90798 | 4/1994 |
| JP | 6-165681 | 6/1994 |
| JP | 7-67657 | 3/1995 |
| JP | 7-209294 | 8/1995 |
| WO | WO 90/14444 | 11/1990 |
| WO | WO 91/08305 | 6/1991 |
| WO | WO 91/11531 | 8/1991 |
| WO | WO 91/16454 | 10/1991 |
| WO | WO 91/18926 | 12/1991 |
| WO | WO 92/03455 | 3/1992 |
| WO | WO 92/11273 | 7/1992 |
| WO | WO 92/14488 | 9/1992 |
| WO | WO 93/03186 | 2/1993 |
| WO | WO 93/12245 | 6/1993 |
| WO | WO 94/02645 | 2/1994 |
| WO | WO 94/17205 | 8/1994 |
| WO | WO 95/00650 | 1/1995 |
| WO | WO 95/09025 | 4/1995 |
| WO | WO 95/20055 | 7/1995 |
| WO | WO 96/00298 | 1/1996 |
| WO | WO 96/02648 | 2/1996 |
| WO | WO 96/08582 | 3/1996 |
| WO | WO 96/18745 | 6/1996 |
| WO | WO 98/20157 | 5/1998 |
| WO | WO 99/24059 | 5/1999 |
| WO | WO 00/14274 | 3/2000 |
| WO | WO 01/23604 | 4/2001 |
| WO | WO 2004/055205 | 7/2004 |

OTHER PUBLICATIONS

Bremaud, L. et al. (1995), Genetic and molecular analysis of the tRNA-tufB operon of the myxobacterium *Stigmatella aurantiaca*, Nucleic Acids Research 23(10):1737-1743.
Brisson-Noël, et al. (1988), Evidence for natural gene transfer from gram-positive cocci to *Escherichia coli*, Journal of Bacteriology 170(4)1739-1745.
Carlin, N.I.A. et al. (1992), Monoclonal antibodies specific for elongation factor Tu and complete nucleotide sequence of the tuf gene in *Mycobacterium tuberculosis*, Infection and Immunity 60(8):3136-3143.
Chamberland, S. et al. (1992), Antibiotic susceptibility profiles of 941 gram-negative bacteria isolated from septicemic patients throughout Canada, Clinical Infectious Diseases 15:615-628.
Croizé, J. (1995), Les méthodes automatisées d'identification des bactéries à l'aube de 1995, La Lettre de l'Infectiologue 10(4):109-113.
Designer PCR, the advertisement from Research Genetics. Nucleic Acids Res. 22(15), Aug. 11, 1994.
Dieffenbach, C.W. and Dveksler, G.S., Eds. (1995), PCR Primer: A Laboratory Manual, Cold Spring Harbor Laboratory Press, pp. 133-155.
Dutka-Malen, S. et al. (1992), Sequence of the vanC gene of *Enterococcus gallinarum* BM 4174 encoding a D-alanine:D-alanine ligase-related protein necessary for vancomycin resistance, Gene 112:53-58.
East, A.K. and Dyke, K.G.H. (1989), Cloning and sequence determination of six *Staphylococcus aureus* beta-Lactamases and their expression in *Escherichia coli* and *Staphylococcus aureus*, Journal of General Microbiology 135:1001-1015.
Ehrlich, G.D. and Greenberg, S.J. (1994), PCR-based diagnosis in infectious disease, Blackwell Scientific Publications, pp. 3-18 and 665-687.
Emori, T.G. and Gaynes, R.P. (1993), An overview of nosocomial infections, including the role of Microbiology Laboratory, Clinical Microbiology Reviews 6(4):428-442.
Evers, S. et al. (1994), Sequence of the vanB and ddl genes encoding D-alanine:D-lactate and D-alanine:D-alanine ligases in vancomycin-resistant *Enterococcus faecalis* V583, Gene 140:97-102.
Eykyn, S.J. et al. (1990), The causative organisms of septicaemia and their epidemiology, Journal of Antimicrobial Chemotherapy 25(Suppl. C):41-58.
Fani, R. et al. (1993), Use of random amplified polymorphic DNA (RAPD) for generating specific DNA probes for microorganisms, Molecular Ecology 2:243-250.
Fleischmann, R.D. et al. (1995), Whole-genome random sequencing and assembly of *Haemophilus influenzae* Rd, Science 269:496-498, 507-512.
Flores, N. et al. (1992), Recovery of DNA from agarose gels stained with Methylene Blue, Biotechniques 13(2):203-205.
Kamla, V. (1994), Database Empro, EMBL, AC:Z34275.
Kellogg, D.E. et al. (1994), TaqStart antibody: "Hot Start" PCR facilitated by a neutralizing monoclonal antibody directed against TaqDNA polymerase, BioTechniques 16(6):1134-1137.
Koenig, C. et al. (1992), Analyses of the Flash Track DNA Probe and UTIscreen bioluminescence tests for bacteriuria, Journal of Clinical Microbiology 30(2):342-345.
Kwok, S. and Higuchi, S. (1989). "Avoiding false positive with PCR." Nature 339:237-238.
Lee, H.H., Morse, S.A. and Olsvik, O., Eds. (1997), Nucleic Acid Amplification Technologies: Application to Disease Diagnosis, Biotechniques Books, Div. Eaton Publishing, p. 7.
Lewin, B. (1990), Genes IV, Oxford University Press, pp. 497-517.
Loechel, S. et al. (1989), Nucleotide sequence of the tuf gene from *Mycoplasma genitalium*, Nucleic Acids Research 17(23):10127.
Ludwig, W. et al. (1994), Database Empro. EMBL, AC:X76863, X76866, X76867, X76871, X76872.
Luneberg et al. (1993), Detection of *Mycoplasma pneumoniae* by polymerase chain reaction and nonradioactive hybridization in microtiter plates, Journal of Clinical Microbiology 31(5):1088-1094.
Monod, M. et al. (1986), Sequence and Properties of pIM13, a Macrolide-Lincosamide-Streptogramin B Resistance Plasmid from *Bacillus subtilis*, Journal of Bacteriology 167(1):138-147.
Murphy, E. et al. (1986), Database Empro. EMBL, AC:X03216.
Neidhardt, F.C. et al., Eds. (1996), *Escherichia coli* and *Salmonella* Cellular and Molecular Biology, 2nd Ed., vol. 1 ASM Press, pp. 1432-1457.
Ohama, T. et al. (1987), Organization and codon usage of the Streptomycin operon in *Micrococcus luteus*, a bacterium with a high genomic G+C content, Journal of Bacteriology 169(10):477-4777.
Olcen et al. (1995), Rapid diagnosis of bacterial meningitis by a seminested PCR strategy, Scand. J. Infect. Dis. 27:537-539.
Ouellette, M. et al. (1987), Precise insertion of antibiotic resistance determinants into Tn21-like transposons: Nucleotide sequence of the OXA-1 beta-lactamase gene, Proc. Natl. Acad. Sci. USA 84:7378-7382.
Perlee, L. et al. (1993), Database Empro. EMBL, CA:L23125.
Persing, D.H. et al., Eds. (1993). Diagnostic molecular microbiology: Principles and applications, American Society for Microbiology, Washington, D.C. pp. xxi, 51-104.
Pezzlo, M.T. et al. (1992), Detection of bacteriuria and Pyuria by URISCREEN a rapid enzymatic screening test, Journal of Clinical Microbiology 30:680-684.
Podbielski, *Streptococcus agalactiae* camp gene. Submitted to Genbank database on Mar. 22, 1993, accession No. X72754.
Podzorski, R.P. and Parsing, D.H. (1995), Molecular detection and identification of microorganisms, In "Manual of Clinical Microbiology", ASM press, pp. 130-157.
Porcella, S.F. et al. (1996), Identification of an EF-Tu protein that is periplasm-associated and process in *Neisseria gonorrhoeae*, Microbiology 142:2481-2489.

Sambrook, J. et al., Eds. (1989), Molecular Cloning: A Laboratory Manual, 2nd Ed. Cold Spring Harbor Laboratory Press, pp. 1.21-1.52, 9.31-9.62, 10.1-10.70, 11.1-11.61.
Sanger, F. et al. (1977), DNA sequencing with chain-terminating inhibitors, Proc. Natl. Acad. Sci. USA 74(12):5463-5467.
Shaw, K.J. et al. (1989), Isolation, characterization and DNA sequence analysis of an AAC(6')-II gene from *Pseudomonas aeruginosa*, Antimicrobial Agents and Chemotherapy 33(12):2052-2062.
Stager, C.E. and Davis, J.R. (1992), Automated systems for identification of microorganisms, Clinical Microbiology Reviews 5(3):302-327.
Stark, R.P. and Maki, D.G. (1984), Bacteriuria in the catherized patient, The New England Journal of Medicine 311(9):560-564.
Watson, J.D. et al. (1976), Molecular Biology of the Gene, 4th Ed. The Benjamin/Cummings Publishing Company, Inc., pp. 339-358.
York, M.K. et al. (1992), Evaluation of the autoSCAN-W/A rapid system for identification and susceptibility testing of gram-negative fermentation bacillia, Journal of Clinical Microbiology 30(11):2903-2910.
Yoshikawa et al. (1995), *Bacillus subtilis* genes for RNA polymerase beta subunit, ribosomal proteins L12 and S7, elongation factors G and Tu and ribosomal proteins S10 and L3. Submitted to DDBJ/EMBL/Genbank database on Apr. 15, 1995.
Yoshikawa, H. (1996), Database Empro. EMBL, AC:D64127.
You-Xun, Z. et al. (1994), Cloning, sequencing and expression in *Escherichia coli* of the gene encoding a 45-kilodalton protein, elongation factor Tu, from *Chlamydia trachomatis* Serovar F, Journal of Bacteriology 176(4):1184-1187.
Murakami, et al. "Identification of methicillin-resistant strains of staphylococci by polymerase chain reaction." Journal of Clinical Microbiology. 29(10): 2240-2244 (1991).
Abdulkarim et al., Homologous Recombination between the *tuf* Genes of *Salmonella typhimurium*, J Mol Bio.(1996) 260: 506-522.
Abe et al., A Sensitive Method for the Detection of Enterotoxigenic *Escherichia coli* by the Polymerase Chain Reaction Using Multiple Primer Pairs, Zentralbl bakteriol. (1992) 277(2): 170-8 (Abstract).
Akaboshi et al., Nucleotide sequence of the recA gene of *Proteus mirabilis*, Nucleic Acids Res. (1989) 17(11): 4390-4390.
Altschul et al., Basic Local Alignment Search Tool, J Mol Biol. (1990) 215: 403-410.
Amann et al., β-Subunit of ATP-Synthase: A Useful Marker for Studying the Phylogenetic Relationship of Eubacteria J Gen Microbiol. (1988) 134: 2815-2821.
Anborgh et al., New Antibiotic that Acts Specifically on the GTP-Bound Form of Elgonation Factor Tu, EMBO J. (1991) 10(4): 779-784.
Ashimoto et al., Molecular epidemiology of *Staphylococcus* spp. contamination in the ward environment: study on mecA and femA genes in methicillin-resistant strains, Kasenshogaku Zasshi (1995) 69: 15-20.
Bäckman et al., Evaluation of an Extended Diagnostic PCR Assay for Detection and Verification of the Common Causes of Bacterial Meningitis in CSF and other Biological Samples, Mol Cell Probes (1999) 13: 49-60.
Balows et al., Eds. The Prokaryotes: A Handbook on the Biology of Bacteria: Ecophysiology, Isolation, Identification, Applications, 2nd Ed., Brenner, Introduction to the Family Enterobacteriaceae, Springer Verlag (1992) Chapter 141, pp. 2673-2695.
Balows et al., Eds. The Prokaryotes: A Handbook on the Biology of Bacteria: Ecophysiology, Isolation, Identification, Applications, 2nd Ed., Brenner, Additional Genera of Enterobacteriaceae, Springer Verlag (1992) Chapter 155, pp. 2922-2937.
Bej et al., Multiplex PCR amplification and immobilized capture probes for detection of bacterial pathogens and indicators in water, Mol. Cell. Probes (1990) 4: 353-365.
Belay et al., Methanogenic Bacteria from Human Dental Plaque, App Environ Microbiol.(1988) 54(2): 600-603.
Belay et al., Methanogenic Bacteria in Human Vaginal Samples, J Clin Microbiol.(1990) 28(7): 1666-1668.
Bell et al., Outer membrane protein H1 of *Pseudomonas aeruginosa*: purification of the protein and cloning and nucleotide sequence of the gene, J Bacteriol. (1989) 171(6): 3211-3217.
Bentley et al., Development of PCR-based Hybridization Protocol for Identification of Streptococcal Species, J Clin Microbiol. (1995) 33(5): 1296-1301.
Bercovier et al, Intra and Interspecies Relatedness of *Yersinia pestis* by DNA Hybridization and its Relationship to *Yersinia pseudotuberculosis*, Curr Microbiol. (1980) 4: 225-229.
Bergeron et al., Diagnosing Bacterial Infectious Diseases in One hour: An Essential Upcoming Revolution Infection (1995) 23(2): 69-72.
Bergeron et al., Preventing Antibiotic Resistance through Rapid Genotypic Identification of Bacteria and of Their Antibiotic Resistance Genes in the Clinical Microbiology Laboratory, J Clin Microbiol. (1998) 36(8): 2169-2172.
Berkenkamp et al, Infrared MALDI Mass Spectrometry of Large Nucleic Acids, Science (1998) 281: 260-262; American Association for the Advancement of science.
Black et al., Detection of streptococcal pyrogenic exotoxin genes by a nested polymerase chain reaction, Mol. Cell. Probes, 7 (1993) 255-259.
Brakstad et al., Detection of *Staphylococcusa aureus* by Polymerase Chain Reaction Amplification of the *nuc* Gene, J Clin Microbiol. (1992) 30(7): 1654-1660.
Brakstad et al., Comparison of Various Methods and Reagents for Species Identification of *Staphylococcus aureus* Positive or Negative for the mecA Gene, APMIS (1993) 101(9):651-654.
Brakstad et al., Multiplex Polymerase Chain Reaction for Detection of Genes for *Staphylococcus aureus* Thermonuclease and Methicillin Resistance and Correlation with Oxacilin Resistance, APMIS (1993) 101(9): 681-688.
Brakstad et al., Direct Identification of *Staphylococcus aureus* in blood cultures by detection of the gene encoding the thermostable nuclease or the gene product, APMIS (1995) 103: 209-218.
Brenner et al., Polynucleotide sequence relatedness among three groups of pathogenic *Escherichia coli* strains, Infect Immun. (1972) 6(3): 308-315.
Brenner et al., Polynucleotide sequence divergence among strains of *Escherichia coli* and closely related organisms, J Bacter. (1972) 109(3): 953-965.
Brenner et al., *Enterobacter gergoviae sp nov.*: a new species of *Enterobacteriaceae* found in clinical specimens and the environment, Int J Syst Bacter. (1980) 30(1): 1-6.
Brenner et al., *Escherichia vulneris*: a New Species of *Enterobacteriaceae* associated with human wounds, J Clin Microbiol. (1982) 15(6): 1133-1140.
Brenner et al., Attempts to classify herbicola group—*Enterobacter agglomerans* strains by deoxyribonucleic acid hybridization and phenotypic tests, Int J Sys Bacter. (1984) 34(1): 45-55.
Brenner et al., *Enterobacter asburiae* sp nov., a new species found in clinical spencimens, and reassignment of *Ervinia dissolvens* and *Ervinia nimipressuralis* to the genus *Enterobacter* as *Enterobacter dissolvens* comb nov and *Enterobacter nimipressuralis* comb nov., J Clin Microbiol. (1986) 23(6): 1114-1120.
Brenner et al., Classification of citrobacteria by DNA hybridization: Designation of *Citrobacter farmeri* sp nov., *Citrobacter youngae* sp nov., *Citrobacter braakii* sp nov., *Citrrobacter werkmanii* sp nove., *Citrobacter sedlakii* sp nove., and three unnambed *Citrobacter* genomospecies, *Int J System Bacter*. (1993) 43(4): 645-658.
Brenner et al., Encoded combinatorial chemistry, Proc Natl Acad Sci. USA (1992) 89: 5381-5383.
Brenner et al., Biochemical identification of *Citrobacter* species defined by DNA hybridization and description of *Citrobacter gillenii* sp nov., J Clin Microbio. (1999) 37(8): 2619-2624.
Buck, et al., Design Strategies and Performance of Custom DNA Sequencing Primers, Biotechniques (1999) 27(3): 528-536.
Caldas et al., Chaperone properties of bacterial elongation factor EF-Tu, J Biol Chem. (1998) 273(19): 11478-11482.
Chen et al., Transcription and expression of the exotoxin A gene of *Pseudomonas aeruginosa*, Gen Microbiol. (1987) 133 (11): 3081-3091.
Chen et al., Broad range DNA probes for detecting and amplifying eubacterial nucleic acids, FEMS Micro Lett. (1989) 57: 19-24.
Chiu et al., Mass spectrometry of nucleic acids, Clin Chem. (1999) 45: 1578-1579.

Christensen et al., Phylogenetic relationships of *Salmonella* based on DNA sequence comparison of atpD encoding the β subunit of ATP synthase, FEMS Micro Lett. (1998) 161: 89-96.
Cilia et al., Sequence heterogeneities among 16S Ribosomal RNA sequences, and their effect on phylogenetic analyses at the species level, Clin Chem. ((1999) 45: 451-461.
Clayton et al., Intraspecific variation in small-subunit rRNA sequences in GenBank: Why single sequences may not adequately represent prokaryotic taxa, Int J System Bacteriol. (1995) 45(3): 595-599.
Cleuziat et al., Specific detection of *Escherichia coli* and *Shigella* species using fragments of genes coding for b-glucuronidase, FEMS Microbiol. Letters, (1990) 72: 315-322.
Cormican et al., Multiplex PCR for identifying mycobacterial isolates, J Clin Pathol. (1995) 48: 203-205.
Cote et al. Molecular Typing of *Haemophilus influenzae* Using a DNA Probe and Multiplex PCR, Mol Cell Probes, (1994) 8(1): 23-37.
Cousineau et al., On the Origin of Protein Synthesis Factors: A Gene Duplication/Fusion Model, J Mol Evol (1997) 45: 661-670.
Deneer et al., Species-Specific Detection of *Listeria monocytogens* by DNA amplification, Appl. Envion Mircobiol. (1991) 57(2): 606-609.
Dickey et al., Emended description of *Enterobacter cancerogenus* comb nov. Int J System Bacteriol. (1988) 38(4): 371-374.
Dieffenbach et al., General concepts for PCR primer design, Genome Research (1993) 3: 30-37.
Dieffenbach et al. Eds. PCR Primer: A laboratory manual, Kwok et al., Design and use of mismatched and degenerate primers, Cold Spring Harbor Laboratory Press (1995) pp. 143-155.
Dopazo, et al., A Computer Program for the Design of PCR Primers for Diagnosis of Highly Variable Genomes, J Virol Meth. (1993) 41:157-165.
Drmanac et al., DNA Sequence Determination by Hybridization: A strategy for efficient large-scale sequencing, Science (1993) 260: 1649-1652.
Dutilh et al., Specific Amplifications of a DNA Sequence Common Toall *Chylamydia trachomatis* Serovars using the Polymerase Chain Reaction, Res Microbiol., (1989) 140: 7-16.
Dutka-Malen et al., Detection of Glycopeptide Resistance Genotypes and Identification to the Species Level of Clinically Relevant *Enterococci* by PCR, J Clin Microbiol. (1995) 31(1): 24-27.
Edwards et al., Multiplex PCR: Advantages, Development, and Applications, PCR Meth. Appl. (1994) 3: 565-575.
Egholm et al., PNA hybridizes to complementary oligonucleotides obeying the Watson-Crick hydrogen-bonding rules, Nature (1993) 365(10): 566-568.
Experimental Protocol concerning Enablement of EP-B1 804 616 signed by Martin Gagnon/Marc Ouellette on Mar. 24, 2004.
Farmer III et al., *Enterobacter sakazakii*: A new species of "*Enterobacteriaceae*" isolated from clinical specimens, Int J System Bacter. (1980) 30(3): 569-584.
Farmer III et al., Biochemical identification of new species and biogroups of *Enterobacteriaceae* isolated i from clinical specimens, J Clin Microbiol. (1985) 21(1): 46-76.
Farmer III et al., *Escherichia fergusonii* and *Enterobacter taylorae*, two new species of *Enterobacteriaceae* isolated from clinical specimens, J Clin Microbiol. (1985) 21(1): 77-81.
Farmer III, Proposed Rewording of Rule 10C of the Bacteriological Code, Int J Syst Bacter. (1985) 35(2): 222.
Figueroa et al., Multiplex Polymerase Chain Reaction based Assay for the Detection of *Babesia bigemina, Babesia bovis* and *Anaplasma marginale* DNA in Bovine Blood, Vet Parasit., (1993) 50: 69-81.
Filer et al., Duplication of the *tuf*Gene, which encodes peptide chain elongation factor Tu, is widespread in gram-negative bacteria, J Bacter. (1981) 148(3): 1006-1011.
Fischer et al., Mannitol-specific Phosphoenolpyruvate-dependent Phosphotransferase System of *Enterococcus faecalis*: Molecular Cloning and Nucleotide Sequences of the Enzyme $III^{Mtl}$ Gene and the Mannitol-1-phosphate Dehydrogenase Gene, Expression in *Escherichia coli*, and Comparison of the Gene Products with Similar Enzymes, J Bacteriol. (1991) 173(12): 3709-3715.
Fischer et al., Predicting structures for genome proteins, Curr Opin Struct Biol. (1999) 9: 2008-211.
Fox et al., How Close is Close: 16S rRNA sequence identity may not be sufficient to guarantee species identity, Int J Syst Bacter. (1992) 42(1): 166-170.
Fratamico et al., Detection of *Escherichia coli* O157:H7 by multiplex PCR, J Clin Microbiol., (1995) 33(8): 2188-2191.
Friedland et al., Development of a Polymerase Chain Reaction Assay to Detect the Presence of *Streptococcus pneumoniae* DNA, Diagn Microbio Infect Dis. (1994) 20(4): 187-193.
Gannon et al., Rapid and Sensitive Method for Detection of Shiga-like Toxin-producing *Escherichia coli* in Ground Beef Using the Polymerase Chain Reaction, Appl Env Microbiol. (1992) 58(12): 3809-3815.
Gavini et al., Transfer of *Enterobacter agglomerans* (Beijerinck 1999) Ewing and Fife 1972 to *Pantoea* gen. nov. as *Pantoea agglomerans* comb. Nov. and description of *Pantoea dispersa* sp nov., Int J System Bacteriol. (1989) 39(3): 337-345.
Geha et al., Multiplex PCR for Identification of Methicillin-Resistant Staphylococci in the Clinical Labortory, J Clin Microbiol. (1994), 32(7): 1768-72.
GenBank GI:147581 [online] Sep. 14, 1992 [retrieved on Oct. 12, 2008], retrieved from http://www.ncbi.nlm.nik.gov/entrez/viewer.fcgi?147581:OLDID:114614 (4 pages).
Gillespie et al., Detection of *Streptococcus pneumoniae* in sputum samples by PCR, J Clin Microbiol. (1994) 32(5): 1308-11.
Gogarten et al., Evolution of the vacuolar $H^+$-ATPase: Implications for the origin off eukaryotes, Proc Natl Acad Sci. USA, 86: 6661-6665.
Gray et al., Cloning, Nucleotide Sequence, and Expression in *Escherichia coli* of the Exotoxin A Structural Gene of *Pseudomonas aeruginosa*, Proc Natl Acad Sci USA. (1984) 81(9): 2645-2649.
Greer, Comparative modeling of homologous proteins, Methods in Enzymology, (1991) 202: 239-252.
Greisen et al., PCR Primers and Probes for the 16S rRNA Gene of Most Species of Pathogenic Bacteria, Including Bacteria Found in Cerebospinal Fluid, J Clin Microbiol. (1994) 32(2): 335-351.
Griffin et al., Eds PCR Technology—Current Innovations; Sharrocks, Chapter 2: The Design of Primers for PCR; CRC Press (1994) 5-11.
Guay et al., Detection of the Pathogenic Parasite *Toxoplasma gondii* by Specific Amplification of Ribosomal Sequences Using Comultiplex Polymerase Chain Reaction, J Clin Microbiol. (1993) 31(2): 203-207.
Guex et al., Protein modelling for all (Swiss-Model), TIBS 24 Computer Corner (1999) pp. 364-367.
Gupta et al., Protein phylogenies and signature sequences: a reappraisal of evolutionary relationships among *Archaebacteria, Eubacteria*, and *Eukaryotes*, Micro Mol Bio Rev. (1998) 62(4): 1435-1491.
Gutierrez et al., Point Mutations that Reduce the Expression of malPQ, a Positively Controlled Operon of *Escherichia coli*, J Mol Biol. (1984) 177(1): 69-86.
Harrison et al., Eds Micro Total Analysis Systems '98, Anderson et al., Advances in Integrated Genetic Analysis, Proceedings of the uTAS '98 Workshop, Banff, Canada Oct. 13-16, 1998; Kluwer Academic Publishers, Dordrecht, The Netherlands (1998) pp. 11-16, Heller et al., An integrated microelectronic hybridization system for genomic research and diagnostic applications, pp. 221-224.
Hartl et al., The Population Genetics of *Escherichia coli*, Ann Rev Genet. (1984) 18: 31-68.
Hedegaard et al., Identification of *Enterobacteriaceae* by partial sequencing of the gene encoding translation initiation factor 2, Int J System Bacter. (1999) 49: 1531-1538.
Hill et al., Inversions between ribosomal RNA genes of *Escherichia coli*, Proc Natl Acad Sci. USA (1981) 78(11): 7069-7072.
Horii et al., Organization of the recA Gene of *Escherichia coli*, Proc Natl Acad Sci USA. (1980) 77(1): 313-317.
Hotomi et al., Detection of *Haemophilus influenzae* in Middle Ear of Otitis Media with Effusion by Polymerase Chain Reaction, Int J Pediatr Otorhinolaryngol. (1993) 27(2): 19-26.
Houard, et al. Specific Identification of *Bordetella pertussis* by the Polymerase Chain Reaction, Res Microbio. (1989) 140: 477-487.
Hynes et al., PCR Amplification of Streptococcal DNA Using Crude Cell Lysates, FEMS Microbiol Lett. (1992) 94: 139-142.

Ibrahim et al., The phylogeny of the genus *Yersinia* based on 16S rDNA sequences, FEMS Micro Lett. (1993) 114: 173-178.
Innis et al., Eds. Statistical Refinement of Primary Design Parameters, PCR Applications; Beasley et al., Statistical refinement of primer design parameters, Academic Press (1999) Chapter 5: 55-71.
Iwabe et al., Evolutionary relationship of archaebacteria, eubacteria, and eukaryotes inferred from phylogenetic trees of duplicated genes, Proc Natl Acad Sci. USA (1989) 86: 9355-9359.
Izard et al., Deoxyribonucleic acid relatedness between *Enterobacter cloacae* and *Enterobacter amnigenu* sp nov., Int J System Bacter. (1981) 31(1): 35-42.
Janda et al., Prototypal diarrheagenic strains of *Hafnia alvei* are actually members of the genus *Escherichia*, J Clin Microbiol. (1999) 37(8): 2399-2401.
Johnson, et al. Urinary Tract Infections in Women: Diagnosis and Treatment, Ann Intern Med. (1989) 111: 906-917.
Kaper et al., Pathogenicity islands and Other Mobile Genetic Elements of Diarrheagenic *Escherichia coli*, Am Soc Microbio. (1999) 3: 33-58.
Kaufhold et al., Identical Genes Confer High-Level Resistance to Gentamicin upon *Enterococcus faecalis, Enterococcus faecium*, and *Streptococcus agalactiae*, Antimicrob Agents Chemother. (1992) 36(6): 1215-1218.
Kearns et al., Rapid Detection of Methicillin-Resistant Staphylococci by Multiplex PCR, J Hosp Infect. (1999) 43: 33-37.
Khan et al., Detection of *Pseudomonas aeruginosa* from Clinical and Environmental Samples by Amplification of the Exotoxin A Gene Using PCR, Appl Environ Microbiol. (1994) 60(10): 3739-3745.
Kimura, A simple method for estimating evolutionary rates of base substitutions through comparative studies of nucleotide sequences, J Mol Evol (1980) 16: 111-120.
Kitch et al., Evaluation of RApID onE system for identification of 379 strains in the family *Enterobacteriaceae* and oxidase negative, gram-negative nonfermenters, J Clin Microbiol. (1994) 32(4): 931-934.
Kloos et al., Siplified scheme for routine identification of human *Staphylococcus* species, J Clin Microbiol. (1975) 1(1): 82-88.
Kong et al., Co-detection of Three Species of Water-borne Bacteria by Multiplex PCR, Marine Pollution Bulletin, (1995) 31 (4-12): 317-324.
Koshkin et al., LNA (Locked Nucleic Acids): Synthesis of the Adenine, Cytosine, Guanine, 5-Methylcytosine, Thymine and Uracil bicyclonucleoside monomers, oligomerisation, and unprecedented nucleic acid recognition, Tetrahedron (1998) 54: 3607-3630.
Lawrence et al., Molecular and Evolutionary Relationships Among Enteric Bacteria, J Gen Microbiol. (1991) 137(8): 1911-1921.
Le Bouguenec et al., Rapid and Specific Detection of the pap, afa, and sfa Adhesin-encoding Operons in Uropathogenic *Escherichia coli* Strains by Polymerase Chain Reaction, J Clin Microbiol. (1992) 30(5): 1189-1193.
Lewin, Benjamin, Genes IV, Chapter 3: Genes are mutable units; Oxford University Press (1990) pp. 41-56.
Li et al., Identification of *Bordetella pertussis* Infection by Shared-primer PCR, J Clin Microbiol., (1994) 32(3): 783-789.
Livak et al., Oligonucleotides with fluorescent dyes at opposite ends provide a quenched probe system useful for detecting PCR product and nuclei acid hybridization, PCR Methods & Applications, (1995) Cold Spring Harbor Laboratory Press, 4: 357-362.
Lowe et al., Nucleotide Sequence of the Aliphatic Amidase Regulator Gene (amiR) of *Pseudomonas aeruginosa*, FEBS Lett. (1989) 246 (1-2): 39-43.
Ludwig et al., Complete nucleotide sequences of seven eubacterial genes coding for the elongation factor Tu: functional, structural and phylogenetic evaluations, Arch Microbiol. (1990) 153: 241-247.
Ludwig et al., Phylogenetic relationships of *Bacteria* based on comparative sequence analysis of elongation factor Tu and ATP-synthase β-subunit genes, Antonie von Leeuwenhoek (1993) 64: 285-305.
Malloy et al., Detection of *Borrelia burgdorferi* Using Polymerase Chain Reaction, J Clin Microbiol. (1990), 28(6): 1089-1093.
McCabe et al., Bacterial species identification after DNA amplification with a universal primer pair, Mol Gen Metabol. (1999) 66: 205-211.
McIntosh et al., Detection of *Pseudomonas aeruginosa* in Sputum from Cystic Fibrosis Patients by the Polymerase Chain Reactions, Mol Cell Probes (1992) 6(4): 299-304 Abstract.
McMillin et al., Simultaneous Detection of Toxin A and Toxin B Genetic Determinants of *Clostridium difficile* Using the Multiplex Polymerase Chain Reaction, Can J Microbiol., (1992) 38: 81-83.
Miller et al., General microbiology of *recA*: Environmental and evolutionary significance, Ann Rev Microbiol. (1990) 44: 365-394.
Mollet et al., *rpoB* sequence analysis as a novel basis for bacterial identification, Mol Microbiol. (1997) 26(5): 1005-1011.
Murray et al., Eds. Manual of Clinical Microbiology; Tang et al., Molecular detection and identification of microorganisms, ASM Press, 7th Ed, (1999) Chapter 13, pp. 215-244.
Neidhardt et al., Eds. *Escherichia coli* and *Salmonella* Cellular and Molecular Biology, Selander et al., Evolutionary Genetics of *Salmonella enterica*, ASM Press (1996) 2nd Ed., Chapt 147: 2691-2707.
Nelson et al., The Evolution of $H^+$-ATPases, TIBS (1989) 14: 113-116.
Nichols et al., A universal nucleoside for use of ambiguous sites in DNA primers, Letters to Nature (1994) 369: 492-493.
Nikiforov et al., The use of 96-well Polystyrene plates for DNA hybridization-based assays: An evaluation of different approaches of oligonucleotide immobilization, Anal. Biochem. (1995) 227: 201-209.
Nikiforov et al., The use of phosphorothioate primers and exonuclease hydrolysis for the preparation of single-stranded PCR products and their detection by solid-phase hybridization, PCR Methods and Applications, (1994) 3: 285-291.
O'Callaghan et al., Development of a PCR Probe Test for Identifying *Pseudomonas aeruginosa and Pseudomonas* (*Burkholderia*) *cepacia*, J Clin Pathol. (1994) 47(3): 222-226.
Persing et al., Eds. Diagnostic Molecular Microbiology: Principles and Applications, Nucleic Acid Probes for Detection and Identification of Infectious Agents by Tenover, et al., American Society for Microbiology (1993) pp. 3-25.
Persing et al., Eds. Suppl to Diagnostic Molecular Microbiology: Principles and Applications, Genotypic Methods for microbial identification by Relman et al., American Society for Microbiology (1996) pp. 3-31.
Pezzlo, Detection of Urinary Tract Infections by Rapid Methods, Clin Microbiol Rev. (1988) 1(2): 268-280.
Pollard et al., A Polymerase Chain Reaction (PCR) Protocol for the Specific Detection of *Chlamydia* spp., Mol Cell Probes., (1989) 3: 383-389.
Post et al., Molecular Analysis of Bacterial Pathogens in Otitis Media with Effusion, JAMA (1995) 273(20): 1598-1604.
Priebe, et al., Nucleotide Sequence of the *hexA* Gene for DNA Mismatch Repair in *Streptococcus pneumoniae* and Homology of *hexA* to *mutS* of *Escherichia coli* and *Salmonella typhimurium*. J. Bacteriol. (1988) 170: 190-196.
Pritchard et al., Possible Insertion Sequences in a Mosaic Genome Organization Upstream of the Exotoxin A Gene in *Pseudomonas aeruginosa*, J Bacteriol. (1990) 172(4): 2020-2028.
Radstrom et al., Detection of Bacterial DNA in Cerebrospinal Fluid by an Assay for Simultaneous Detection of *Neisseria meningitidis, Haemophilus influenzae*, and *Streptococci* Using a Seminested PCR Strategy, J Clin Microbiol. (1994) 32(11): 2738-2744.
Reeve, Archaebacteria then . . . archaes now (Are there really no archaeal pathogens? J Bacter. (1999) 181(12): 3613-3617.
Rosa et al., A Specific and Sensitive Assay for the Lyme Disease Spirochete *Borrelia burgdorferi* Using the Polymerase Chain Reaction, J Infect Dis. (1989) 160(6): 1018-1028.
Rosa et al., Polymerase Chain Reaction Analyses Identify Two Distinct Classes of *Borrelia burgodorferi*, J Clin Microbiol., (1991) 29(3): 524-532.
Rudolph et al., Evaluation of Polymerase Chain Reaction for Diagnosis of Pneumococcal pneumonia, J Clin Microbiol. (1993) 31(10): 2661-2666.
Ryffel et al., Sequence Comparison of mecA Genes Isolated from Methicillin-resistant *Staphylococcus aureus and Staphylococcus epidermidis*, Gene (1990) 94(1): 137-8 (Abstract).
Sali, Modelling mutations and homologous proteins, Curr Opin Biotech. (1995) 6: 437-451.

Sambrook et al., Eds. Molecular Cloning: A Laboratory Manual, 2nd Ed. Cold Spring Harbor Laboratory Press, (1989) pp. pp. 18.35-18.39.

Sánchez et al., Advances in comparative protein-structure modelling, Curr Opin Struct Biol. (1997) 7: 206-214.

Saraste et al., The atp operon: nucleotide sequence of the genes for the γ, β, and ϵ subunits of *Escherichia coli* ATP synthase, Nucl Acids Res. (1981) 9(20): 5287-5296.

Schaechter et al., Mechanisms of Microbial Disease. The Enteric Bacteria: Diarrhea and Dysentery, Dept Microbiol Immunol., (1989), 17: 256-265.

Sela et al., Duplication of the *tuf* Gene: a new insight into the Phylogeny of Eubacteria, J Bacteriol. (1989) 171(1): 581-584.

Sharma et al., Identification of *Yersinia* species by the API 20E, J Clin Microbio. (1990) 28(6): 1443-1444.

Silvestrini et al., Nitrite Reductase from *Pseudomonas aeruginosa*: Sequence of the Gene and the Protein, FEBS Lett. (1989) 254(1-2): 33-38.

Spierings et al., Characterization of the *Citrobacter freundii phoE* Gene and Development of *C. freundii-specific Oligonucleotides*, FEMS Microbiol. Letters (1992) 99:199-204.

Spröer et al., The phylogenetic position of *Serratia, Buttiauxella* and some other genera of the family Enterobacteriaceae, Int J System Bacteriol. (1999) 49: 1433-1438.

Stackebrandt et al., Taxonomic note: A place for DNA-DNA reassociation and 16S rRNA sequence analysis in the present species definition in bacteriology, Int J System Bacteriol. (1994) 44(4): 846-849.

Stacy-Phipps et al. Multiplex PCR Assay and Simple Preparation Method for Stool Specimans Detect Enterotoxigenic *Escherichia coli* DNA during Course of Infection, J Clin Microbio. (1995) 33(5): 1054-1059.

Steigerwalt et al., DNA relatedness among species of *Enterobacter* and *Serratia*, Can J Microbiol. (1976) 22: 121-137.

Su et al., Nucleotide Sequence of the Gelatinase Gene (gelE) from *Enterococcus faecalis* subsp. *liquefaciens*, Infect. Immun. (1991) 59(1): 415-420.

Takezaki et al. Phylogenetic test of the molecular clock and linearized trees, Mol Biol Evol. (1995) 12(5): 823-833.

Taylor, Remotely related sequences and structures: analysis and predictive modelling, Trends 220 Biotechnol. (1994) 12(5): 154-158.

Tyagi et al., Molecular beacons: probes that fluoresce upon hybridization, Nature Biotech. (1996) 14: 303-308.

Tyler et al., Streptococcal Erythrogenic Toxin Genes: Detection by Polymerase Chain Reaction and Association with Disease in Strains Isolated in Canada from 1940 to 1991, J Clin Microbiol. (1992) 30(12): 3127-3131.

Ubukata et al., Rapid Detection of the mecA Gene in Methicillin-resistant Staphylococci by Enzymatic Detection of Polymerase Chain Reaction Products, J Clin Microbiol. (1992) 30(7): 1728-1733.

Ueyama et al., High Incidence of *Haemophilus influenzae* in Nasopharyngeal Secretions and Middle Ear Effusions as Detected by PCR, J Clin Microbiol. (1995) 33(7): 1835-1838.

Ünal et al., Detection of Methicillin-Resistant Staphylococci by Using the Polymerase Chain Reaction, J Clin Microbio., (1992) 1685-1691.

Van Burik et al., Panfungal PCR Assay for Detection of Fungal Infection in Human Blood Specimens, J Clin Microbiol. (1998) 36(5): 1169-1175.

van Ketel, Detection of *Haemophilus influenzae* in Cerebrospinal Fluids by Polymerase Chain Reaction DNA Amplification, J Med Microbiol., (1990) 33: 271-276.

Vannuffel et al., Specific Detection of Methicillin-Resistant *Staphylococcus* Species by Multiplex PCR, J Clin Microbiology, (1995) 2864-2867.

Vijgenboom et al., Three *tuf*-like genes in the Kirromycin producer *Strept myc s ramocissimus*, Microbiol. (1994) 140: 983-998.

Wang et al., A 16S rDNA-based PCR Method for Rapid and Specific Detection of *Clostridium perfringens* in Food, Mol Cell Probes (1994) 8(2): 131-137.

Wang et al., Phylogenetic analysis and identification of *Shigella spp by molecular probes, Mol Cell Probes* (1997) 11: 427-432.

Watson et al., Molecular Biology of the Gene, vol. I—General Principles; 4th Ed. The Benjamin/Cummings Publishing Company, Inc., (1987) pp. 431-462.

Way et al., Specific Detection of *Salmonella spp*. By Multiplex Polymerase Chain Reaction, App Environ Microbiol. (1993) 59(5): 1473-1479.

Wayne et al., Report of the Ad Hoc Committee on Reconciliation of approaches to bacterial systematics, Int J Sys Bacter. (1987) 37(4): 463-464.

Weaver et al., Incidence of methanogenic bacteria in a sigmoidoscopy population: an association of methanogenic bacteria and diverticulosis, Gut 27: 698-704.

Weickmann and Weickmann, Reference D34, European Opposition for EP 0804616Spezifität der Primer, Annex II: Specific and ubiquitous primers for DNA amplification, 11 pages, (Sep. 13, 2007).

Weickmann and Weickmann, Reference D35, European Opposition for EP 0804616, Vergleich: Bacterial species: *Escherichia coli* (Sep. 13, 2007).

Weickmann and Weickmann, Reference D40, European Opposition for EP 0804616, Comparison of Sequences TRP.0O3 and TRP.004 of W0 93/12245 with SEQ ID No. 5 of EP 804616 (Sep. 13, 2007).

Weickmann and Weickmann, Reference D43, European Opposition for EP 0804616Comparison of Sequence *E. coli* malPQ operon, 5'-end of Gutierrez et al., J. Mol. Biol. 177(1) (1984) 69-86 with SEQ ID No. 6 (glycogen phosphorylase) of EP 804616; of Sequence *E.coli* recA gene, 5'-region of Zhao et al., Mol.Gen.Genet. 222(2-3) (1990) 369-376 with SEQ ID No. 7 of EP 804616, and of exotoxin A gene of Chen et al., J. Gen. Microbiol. 133(11) (1987) 3081-3091 with SEQ ID No. 18 of EP 804616 (Sep. 13, 2007).

Weickmann and Weickmann, Reference D49, European Opposition for EP 0804616, Vergleich der SEQ ID No. 26 (*Haemophilus influenzae* omp P1 gene) aus EP804616 und Sonde 106b aus EP804616 mit Primer Homp1 und Homp3 aus Cote S. et al., Mol. Cell. Probes (Feb. 1994) 8:23-37 (Sep. 13, 2007).

Weickmann and Weickmann, Reference D50, European Opposition for EP 0804616, Vergleich der SEQ ID No. 27 (*Haemophilus influenzae*transformation gene cluster) und Primer 154 bzw 155b und Sonde 107b aus EP804616 mit Primer Htra3 aus Cote S. et al., Mol. Cell. Probes (Feb. 1994) 8:23-37.

Weickmann and Weickmann, Reference D52, European Opposition for EP 0804616, Comparison of SEQ ID No. 8 to 21 of EP577523 with neuraminidase nanA of *Streptococcus pneumoniae* (cf. SEQ ID No. 35 of EP804616).

Weickmann and Weickmann, Reference D54, European Opposition for EP 0804616, Comparison of SEQ ID No. 1 and Primers YR2 and YR6 of FR2686604 with primers SEQ ID No. 141 and 142 of EP804616 (Sep. 13, 2007).

Weickmann and Weickmann, Reference D56, European Opposition for EP 0804616, Vergleich der SEQ ID No. 33 (*Streptococcus pyogenes* Exotoxin A gene) aus EP804616 und Primern SEQ ID Nos. 143 bzw. 144b (EP804616) mit speA-Primern P1-P4 aus Black C.M. et al., Mol. Cell. Probes (1993) 7:255-259 und speA-primern SPEA-1, SPEA-2 aus Tyler S.D. et al., J.Clin.Microbiol.Dis. (1992) 30:3127-3131 (Sep. 13, 2007).

Weickmann and Weickmann, Reference D58, European Opposition for EP 0804616, References for target genes (Sep. 13, 2007).

Weickmann and Weickmann, Reference D72, European Opposition for EP 0804616Vergleich der SEQ ID Nos. 18 und 20 (*Pseudomonas aeruginosa*) aus EP804616 und der entsprechenden Probesequenzen SEQ ID Nos. 87-90 und 94+95 mit Primer und Probesequenzen ETA1-ETA7 aus Khan et al., Appl. Environment. Microbiol. Oct. 1994.

Westin et al., Anchored multiplex amplification on a microelectronic chip array, Nature Biotech. (2000) 18: 199-204.

Whitcombe et al., Detection of PCR products using self-probing amplicons and fluorescence, Nature Biotech. (1999) 17: 804-807.

White et al., The Polymerase Chain Reaction: Clinical Applications, Adv Clin Chem. (1992) 29: 161-196.

Wilson et al., Detection of Enterotoxigenic *Staphlococcus aureus* in Dried Skimmed Milk: Use of the Polymerase Chain Reaction for Amplification and Detection of Staphylococcal Enterotoxin Genes *entB* and *entC1* and the Thermonuclease Gene *nuc*. Appl Environ Microbiol., (1991) 1793-1798.

Wittwer et al., Rapid Cycle DNA Amplification: Time and Temperature Optimization, Biotechniques (1991) 10(1): 76-83.
Wittwer et al., The LightCycler™: A microvolume multisample fluorimeter with rapid temperature control, Bio Techniques (1997) 22: 176-181.
Yanofsky et al., The Complete Nucleotide Sequence of the Tryptophan Operon of *Escherichia coli*. Nucleic Acids Res. (1981) 9(24): 6647-6668.
Zakrewska-Czerwińska et al., Identification of *Staphylococcus epidermidis* Using a 16S rRNA-directed Oligonucleotide Probe, FEMS Microbiol Lett. (1992) 100: 51-58.
Zambardi et al., Laboratory Diagnosis of Oxacillin Resistance in *Staphylococcus aureus* by a Multiplex-polymerase Chain Reaction Assay, Diagn Microbiol Infect Dis. (1994) 19: 25-31.
Zhao et al., DNA Sequence Analysis of the recA Genes from *Proteus vulgaris, Erwinia carotovora, Shigella flexneri* and *Escherichia coli* B/r, Mol Gen Genet. (1990) 222(2-3): 369-376.
Aragón et al., Increase in β-lactam-resistant *Proteus mirabilis* Strains due to CTX-M- and CMY-type as well as New VEB- and Inhibitor-resistant TEM-type β-lactamases, J Antimicro Chemother. (2008) 61: 1029-1032.
Bagley et al., Significance of Fecal Coliform-positive *Klebsiella*, App Environ Microbio. (May 1977) 33(5): 1141-1148.
Duncan, Susceptibility of 1,500 Isolates of *Pseudomonas aeruginosa* to Gentamicin, Carbenicillin, Colistin, and Polymyxin B, Antimicro Agents Chemother. (Jan. 1974) 5(1): 9-15.
Feizabadi, Drug Resistant Patterns of *Enterococci Recovered from Patients in Tehran During 2000-2003, Letters to the Editor, Int J Antimicrob Agents* (2004) 24: 521-522.
Fenoll et al., Serotype Distribution and Antimicrobial Resistance of *Streptococcus pneumoniae* Isolates Causing Systemic Infections in Spain, 1979-1989, (1991) 13: 56-60.
Higashide et al., Methicillin-resistant *Staphylococcus saprophyticus* Isolates Carrying Staphylococcal Cassette Chromosome *mec* Have Emerged in Urogenital Tract Infections, Antimicrob Agents Chemother. (Jun. 2008) 52(6): 2061-2068.
Madico et al., Touchdown Enzyme Time Release-PCR for Detection and Identification of *Chlamydia trachomatic, C. pneumoniae*, and *C. psittaci* Using the 16S and 16S-23S Spacer rRNA Genes, J Clin Microbiol., (Mar. 2000) 38(3): 1085-1093.
Metherell et al., Rapid, sensitive, mircobial detection by gene amplification using restriction endonuclease target sequences, Mol Cell Probes (1997) 11: 297-308.
NCBI Blast: Nucleotide Sequence, Attachment for Sequence Comparison between 5'-CCAGCTGTA TTAGAAGTA-3' from Seq ID No:9 and Genomes of *Bacteria Bacillus Cereus* Q1 and AH187, (online: Apr. 12, 2009) 1 page.
NCBI Blast: Nucleotide Sequence, Attachment for Sequence Comparison between 5'CTGAACATTATC TTTGAT-3' from Seq ID No. 10 and Complete Genome of *Streptococcus mutans* UA159, (online: Apr. 12, 2009) 1 page.
Paradis et al., The Potential of EF-Tu Sequences for Identification of Clinically Important *Enterobacteriaceae* Species (Sep. 1999) 39: 227; Abstract 1574, only.
Post et al., Development and Validation of a Multiplex PCR-based Assay for the Upper Respiratory Tract Bacterial Pathogens *Haemophilus influenzae, Streptococcus pneumoniae*, and *Moraxella catarrhalis*, (1996) 1(1): 29-39.
Zhanel et al., Antimicrobial Resistance in *Haemophilus influenzae* and *Moraxella catarrhalis* Respiratory Tract Isolates: Results of the Canadian Respiratory Organizm Susceptibility Study, 1997 to 2002, Antimicrob Agents Chemother., (Jun. 2003) 47(6): 1875-1881.
Bej et al., Detection of coliform bacteria and *Escherichia coli by* multiplex polymerase chain reaction: Comparison with defined substrate and plating methods for water quality monitoring, Appl Environ Microbio., (Aug. 1991) 57(8): 2429-2432.
Cebula, et al., Simultaneous identification of strains of *Escherichia coli* Serotype O157:H7 and their shiga-like toxin type by mismatch amplification mutation assay-multiplex PCR, J Clin Microbio. (Jan. 1995) 33(1): 248-250.
Frankel et al., Multi-gene amplification: simultaneous detection of three virulence genes in diarrhoeal stool, Mol Microbio. (1989) 3(12): 1729-1734.
Haas et al., Universal PCR primers for detection of phytopathogenic *Agrobacterium* strains, App Environ Microbio., (Aug. 1995) 61(8): 2879-2884.
Kaltenboeck et al., Two-step polymerase chain reactions and restriction endonuclease analyses detect and differentiate *ompA* DNA of *Chlamydia* spp., J Clin Microbio. (May 1992) 30(5): 1098-1104.
GenBank Accession No. FJ858146, *Enterococcus faecium* Strain QSE32 fsr Operon, Complete Sequence; and GelE (gelE) and SprE (sprE) Genes, Complete CDS, (Nov. 2009) http://ncbi.nlm.nih.gov/nuccore/226938234.
GenBank Accession No. AP000565, *Homo sapiens* Genomic DNA, Chromosome 21Q22, clone:f79A10, D21S226-AML Region, Complete Sequence, (Nov. 1999) http://ncbi.nlm.nih.gov/nuccore/6015482.
Harth et al., Epidemiology of *Vibrio parahaemolyticus* Outbreaks, Southern Chile, Emerg Infect Dis., (Feb. 2009) 15(2): 163-168 and GenBank Accession No. EU185084 downloaded from http://ncbi.nlm.nih.gov/nuccore/158524083.
Lucotte et al., A multiple primer pairs polymerase chain reaction for the detection of human genital papillomavirus types, Mol Cell Probes (1993) 7: 339-344.
Opposition Brief by Infectio Diagnostic (I.D.I.) Inc. dated Sep. 14, 2007 from EP Application No. 95931109.3, filed Sep. 12, 1995.
Opposition Brief by Roche Diagnostics GmbH dated Sep. 21, 2007 from EP Application No. 95931109.3, filed Sep. 12, 1995.
Reply Brief by Roche Diagnostics GmbH dated Jan. 29, 2008 to Opposition Brief by I.D.I. from EP Application No. 95931109.3, filed Sep. 12, 1995 (w/English translation).
Reply Brief by I.D.I. dated Apr. 1, 2008 to Roche's Appeal Brief from EP Application No. 95931109.3, filed Sep. 12, 1995.
EPO Notice of Summons to Oral Proceedings and Preliminary Opinion dated May 20, 2010 from EP Application No. 95931109.3, filed Sep. 12, 1995.
Reply Brief by I.D.I. dated Sep. 6, 2010 to Summons/Preliminary Opinion from EP Application No. 95931109.3, filed Sep. 12, 1995.
Reply Brief by Roche dated Sep. 6, 2010 to Summons/Preliminary Opinion from EP Application No. 95931109.3, filed Sep. 12, 1995 (w/English translation).
EPO Notice of Decision of Appeal dated Oct. 6, 2010 from EP Application No. 95931109.3, filed Sep. 12, 1995.
Ako-Nai et al., The Characterisation of Clinical Isolates of *Staphylococcus aureus* in Ile-Ife, Nigeria, J Med Microbiol. (1991) 34: 109-112.
Betzl et al., Identification of Lactococci and Enterococci by Colony Hybridization with 23S rRNA-Targeted Oligonucleotide Probes, Appl Environ Microbio., (Sep. 1990) 56(9):2927-2929.
Bongaerts et al., In Vitro Activities of BAY Y3118, Ciprofloxacin, Ofloxacin, and Fleroxacin against Gram-Positive and Gram-Negative Pathogens from Respiratory Tract and Soft Tissue Infections, Antimicro Agents Chemother. (Sep. 1993) 37(9):2017-2019.
Derecola et al., A 5-Year Surveillance Study of 44,691 Isolates of *Haemophilus Influenzae* Project Beta-Alert 1993-1997, Antimicro Agen Chemothera. (Jan. 1999) 43(1):185-186.
Ehrlich et al., Eds. PCR-Based Diagnosis in Infectious Disease, Chapters 1, 3 , Blackwell Scientific Publications (1994), pp. 3-18 and 45-55.
GenBank Accession No. M37185, *Enterococcus faecalis Gelatinase* (gelE) Gene, Complete CDS (Apr. 1993).
GenBank Accession No. Z26902, Phylogenetic Analysis Using 16S rDNA Sequencing of Staphylococci (Oct. 1993).
Guzmàn et al., Role of Adherence in Pathogenesis of *Enterococcus faecalis* Urinary Tract Infection and Endocarditis, Infect Immun. (Jun. 1989) 57(6): 1834-1838.
Izumiya et al., Characterization of Multidrug-Resistant *Salmonella enterica* Serovar Typhimurium Isolated in Japan, J Clin Microbio. (Jul. 2001) 39(7):2700-2703.
Jenkins, F. J., Basic Methods for the Detection of PCR Products, Genome Res. (Apr. 1994) 3:S77-S82.
Jordá, et al. Diagnosis of *Nosocomial pneumonia* in Mechanically Ventilated Patients by the Blind Protected Telescoping Catheter, Intensive Care Med. (1993) 19:377-382.

Kim et al., Simultaneous Detection by PCR of *Escherichia coli, Listeria monocytogenes* and *Salmonella typhimurium* in Artificially Inoculated Wheat Grain, Inter'l J Food Microbio. (Apr. 2006) 111:21-25.
Lewis et al., Emergence of Clinical Isolates of *Staphylococcus aureus* Resistant to Gentamicin and Correlation of Resistance with Bacteriophage Type, J Infect Diseases, (Mar. 1978) 137(3): 314-317.
Miller et al., Community Acquired Lobar pneumonia in Patients with HIV Infection and AIDS, Thorax (Apr. 1994) 49:367-368.
Mitsuhashi M., Technical Report: Part 2. Basic Requirements for Designing Optimal PCR Primers, J Clin Lab Anal., (1996) 10: 285-293.
Neu, Harold C., The Crisis in Antibiotic Resistance, Science (Aug. 1992) 257:1064-1073.
Powers, Robert D., New Directions in the Diagnosis and Therapy of Urinary Tract Infections, (1991) Am J Obstet Gynecol., 164:1387-1389.

SPECIES-SPECIFIC, GENUS-SPECIFIC AND UNIVERSAL DNA PROBES AND AMPLIFICATION PRIMERS TO RAPIDLY DETECT AND IDENTIFY COMMON BACTERIAL AND FUNGAL PATHOGENS AND ASSOCIATED ANTIBIOTIC RESISTANCE GENES FROM CLINICAL SPECIMENS FOR DIAGNOSIS IN MICROBIOLOGY LABORATORIES

CROSS-REFERENCE TO RELATED APPLICATIONS

This application is a continuation of U.S. patent application Ser. No. 10/753,169, to Bergeron, et al., entitled "Species-specific, genus-specific and universal DNA probes and amplification primers to rapidly detect and identify common bacterial and fungal pathogens and associated antibiotic resistance genes from clinical specimens for diagnosis in microbiology laboratories," filed Jan. 7, 2004, which is a continuation of U.S. patent application Ser. No. 09/989,643 filed Nov. 20, 2001, now abandoned, which is a continuation of U.S. patent application Ser. No. 09/297,539, filed May 3, 1999, now abandoned, which is a National Phase Application of International Patent Application No. PCT/CA97/00829, filed Nov. 4, 1997, now closed, which PCT application claims priority under 35 U.S.C. §365(c) to U.S. patent application Ser. No. 08/743,637, filed Nov. 4, 1996, now U.S. Pat. No. 5,994,066.

REFERENCE TO SEQUENCE LISTING, TABLE, OR COMPUTER PROGRAM LISTING

The present application is being filed along with duplicate copies of a CD-ROM marked "Copy 1" and "Copy 2" containing a Sequence Listing in electronic format. The duplicate copies of CD-ROM entitled The "Copy 1" and "Copy 2" each contains a file entitled GENOM047C1C1C.txt created on May 2, 2006 which is 115,712 Bytes in size. The information on these duplicate CD-ROMs is incorporated herein by reference in its entirety.

The Sequence Listing in electronic format is provided as a file entitled GENOM.047C1C1C.TXT which is 110 KB in size. The information in the electronic format of the Sequence Listing is incorporated herein by reference in its entirety.

BACKGROUND OF THE INVENTION

Classical Methods for the Identification and Susceptibility Testing of Bacteria Bacteria are classically identified by their ability to utilize different substrates as a source of carbon and nitrogen through the use of biochemical tests such as the API20E™ system (bioMérieux). For susceptibility testing, clinical microbiology laboratories use methods including disk diffusion, agar dilution and broth microdilution. Although identifications based on biochemical tests and antibacterial susceptibility tests are cost-effective, at least two days are required to obtain preliminary results due to the necessity of two successive overnight incubations to identify the bacteria from clinical specimens as well as to determine their susceptibility to antimicrobial agents. There are some commercially available automated systems (i.e. the MicroScan system from Dade Diagnostics Corp. and the Vitek system from bioMérieux) which use sophisticated and expensive apparatus for faster microbial identification and susceptibility testing (Stager and Davis, 1992, Clin. Microbiol. Rev. 5:302-327). These systems require shorter incubation periods, thereby allowing most bacterial identifications and susceptibility testing to be performed in less than 6 hours. Nevertheless, these faster systems always require the primary isolation of the bacteria as a pure culture, a process which takes at least 18 hours for a pure culture or 2 days for a mixed culture. The fastest identification system, the autoSCAN-Walk-Away™ system (Dade Diagnostics Corp.) identifies both gram-negative and gram-positive bacterial species from standardized inoculum in as little as 2 hours and gives susceptibility patterns to most antibiotics in 5.5 hours. However, this system has a particularly high percentage (i.e. 3.3 to 40.5%) of non-conclusive identifications with bacterial species other than Enterobacteriaceae (Croizé J., 1995, Lett. Infectiol. 10:109-113; York et al., 1992, J. Clin. Microbiol. 30:2903-2910). For Enterobacteriaceae, the percentage of non-conclusive identifications was 2.7 to 11.4%.

A wide variety of bacteria and fungi are routinely isolated and identified from clinical specimens in microbiology laboratories. Tables 1 and 2 give the incidence for the most commonly isolated bacterial and fungal pathogens from various types of clinical specimens. These pathogens are the most frequently associated with nosocomial and community-acquired human infections and are therefore considered the most clinically important.

Clinical Specimens Tested in Clinical Microbiology Laboratories

Most clinical specimens received in clinical microbiology laboratories are urine and blood samples. At the microbiology laboratory of the Centre Hospitalier de l'Université Laval (CHUL), urine and blood account for approximately 55% and 30% of the specimens received, respectively (Table 3). The remaining 15% of clinical specimens comprise various biological fluids including sputum, pus, cerebrospinal fluid, synovial fluid, and others (Table 3). Infections of the urinary tract, the respiratory tract and the bloodstream are usually of bacterial etiology and require antimicrobial therapy. In fact, all clinical samples received in the clinical microbiology laboratory are tested routinely for the identification of bacteria and susceptibility testing.

Conventional Pathogen Identification from Clinical Specimens

Urine Specimens

The search for pathogens in urine specimens is so preponderant in the routine microbiology laboratory that a myriad of tests have been developed. However, the gold standard remains the classical semi-quantitative plate culture method in which 1 μL of urine is streaked on plates and incubated for 18-24 hours. Colonies are then counted to determine the total number of colony forming units (CFU) per liter of urine. A bacterial urinary tract infection (UTI) is normally associated with a bacterial count of 1 CFU/L or more in urine. However, infections with less than $10^7$ CFU/L in urine are possible, particularly in patients with a high incidence of diseases or those catheterized (Stark and Maki, 1984, N. Engl. J. Med. 311:560-564). Importantly, approximately 80% of urine specimens tested in clinical microbiology laboratories are considered negative (i.e. bacterial count of less than $10^7$ CFU/L; Table 3). Urine specimens found positive by culture are further characterized using standard biochemical tests to identify the bacterial pathogen and are also tested for susceptibility to antibiotics. The biochemical and susceptibility testing normally require 18-24 hours of incubation.

Accurate and rapid urine screening methods for bacterial pathogens would allow a faster identification of negative specimens and a more efficient treatment and care management of patients. Several rapid identification methods (Uriscreen™, UTIscreen™, Flash Track™ DNA probes and others) have been compared to slower standard biochemical methods, which are based on culture of the bacterial pathogens. Although much faster, these rapid tests showed low sensitivities and poor specificities as well as a high number of false negative and false positive results (Koening et al., 1992, J. Clin. Microbiol. 30:342-345; Pezzlo et al., 1992, J. Clin. Microbiol. 30:640-684).

Blood Specimens

The blood specimens received in the microbiology laboratory are always submitted for culture. Blood culture systems may be manual, semi-automated or completely automated. The BACTEC system (from Becton Dickinson) and the BacTAlert system (from Organon Teknika Corporation) are the two most widely used automated blood culture systems. These systems incubate blood culture bottles under optimal conditions for bacterial growth. Bacterial growth is monitored continuously to detect early positives by using highly sensitive bacterial growth detectors. Once growth is detected, a Gram stain is performed directly from the blood culture and then used to inoculate nutrient agar plates. Subsequently, bacterial identification and susceptibility testing are carried out from isolated bacterial colonies with automated systems as described previously. The bottles are normally reported as negative if no growth is detected after an incubation of 6 to 7 days. Normally, the vast majority of blood cultures are reported negative. For example, the percentage of negative blood cultures at the microbiology laboratory of the CHUL for the period February 1994-January 1995 was 93.1% (Table 3).

Other Clinical Samples

Upon receipt by the clinical microbiology laboratory, all body fluids other than blood and urine that are from normally sterile sites (i.e. cerebrospinal, synovial, pleural, pericardial and others) are processed for direct microscopic examination and subsequent culture. Again, most clinical samples are negative for culture (Table 3).

Regarding clinical specimens which are not from sterile sites such as sputum or stool specimens, the laboratory diagnosis by culture is more problematic because of the contamination by the normal flora. The bacterial pathogens potentially associated with the infection are purified from the contaminants and then identified as described previously. Of course, the universal detection of bacteria would not be useful for the diagnosis of bacterial infections at these non sterile sites. On the other hand, DNA-based assays for species or genus detection and identification as well as for the detection of antibiotic resistance genes from these specimens would be very useful and would offer several advantages over classical identification and susceptibility testing methods.

DNA-Based Assays with any Clinical Specimens

There is an obvious need for rapid and accurate diagnostic tests for bacterial detection and identification directly from clinical specimens. DNA-based technologies are rapid and accurate and offer a great potential to improve the diagnosis of infectious diseases (Persing et al., 1993, Diagnostic Molecular Microbiology: Principles and Applications, American Society for Microbiology, Washington, D.C.). The DNA probes and amplification primers which are objects of the present invention are applicable for bacterial or fungal detection and identification directly from any clinical specimens such as blood cultures, blood, urine, sputum, cerebrospinal fluid, pus and other type of specimens (Table 3). The DNA-based tests proposed in this invention are superior in terms of both rapidity and accuracy to standard biochemical methods currently used for routine diagnosis from any clinical specimens in microbiology laboratories. Since these tests are performed in around only one hour, they provide the clinicians with new diagnostic tools which should contribute to increase the efficiency of therapies with antimicrobial agents. Clinical specimens from organisms other than humans (e.g. other primates, birds, plants, mammals, farm animals, livestock and others) may also be tested with these assays.

A High Percentage of Culture Negative Specimens

Among all the clinical specimens received for routine diagnosis, approximately 80% of urine specimens and even more (around 95%) for other types of clinical specimens are negative for the presence of bacterial pathogens (Table 3). It would also be desirable, in addition to identify bacteria at the species or genus level in a given specimen, to screen out the high proportion of negative clinical specimens with a test detecting the presence of any bacterium (i.e. universal bacterial detection). Such a screening test may be based on the DNA amplification by PCR of a highly conserved genetic target found in all bacteria. Specimens negative for bacteria would not be amplified by this assay. On the other hand, those that are positive for bacteria would give a positive amplification signal with this assay.

Towards the Development of Rapid DNA-Based Diagnostic Tests

A rapid diagnostic test should have a significant impact on the management of infections. DNA probe and DNA amplification technologies offer several advantages over conventional methods for the identification of pathogens and antibiotic resistance genes from clinical samples (Persing et al., 1993, Diagnostic Molecular Microbiology: Principles and Applications, American Society for Microbiology, Washington, D.C.; Ehrlich and Greenberg, 1994, PCR-based Diagnostics in Infectious Disease, Blackwell Scientific Publications, Boston, Mass.). There is no need for culture of the bacterial pathogens, hence the organisms can be detected directly from clinical samples, thereby reducing the time associated with the isolation and identification of pathogens. Furthermore, DNA-based assays are more accurate for bacterial identification than currently used phenotypic identification systems which are based on biochemical tests. Commercially available DNA-based technologies are currently used in clinical microbiology laboratories, mainly for the detection and identification of fastidious bacterial pathogens such as *Mycobacterium tuberculosis, Chlamydia trachomatis, Neisseria gonorrhoeae* as well as for the detection of a variety of viruses (Podzorski and Persing, Molecular detection and identification of microorganisms, In: P. Murray et al., 1995, Manual of Clinical Microbiology, ASM press, Washington D.C.). There are also other commercially available DNA-based assays which are used for culture confirmation assays.

Others have developed DNA-based tests for the detection and identification of bacterial pathogens which are objects of the present invention: *Staphylococcus* spp. (U.S. Pat. No. 5,437,978), *Neisseria* spp. (U.S. Pat. No. 5,162,199 and European patent application serial No. EP 0 337 896 131) and *Listeria monocytogenes* (U.S. Pat. Nos. 5,389,513 and 5,089,386). However, the diagnostic tests described in these patents are based either on rRNA genes or on genetic targets different from those described in the present invention.

Although there are diagnostic kits or methods already used in clinical microbiology laboratories, there is still a need for an advantageous alternative to the conventional culture identification methods in order to improve the accuracy and the speed of the diagnosis of commonly encountered bacterial infections. Besides being much faster, DNA-based diagnostic tests are more accurate than standard biochemical tests presently used for diagnosis because the bacterial genotype (e.g. DNA level) is more stable than the bacterial phenotype (e.g. metabolic level).

Knowledge of the genomic sequences of bacterial and fungal species continuously increases as testified by the number of sequences available from databases. From the sequences readily available from databases, there is no indication therefrom as to their potential for diagnostic purposes. For determining good candidates for diagnostic purposes, one could select sequences for DNA-based assays for (i) the species-specific detection and identification of commonly encountered bacterial or fungal pathogens, (ii) the genus-specific detection and identification of commonly encountered bacterial or fungal pathogens, (iii) the universal detection of bacterial or fungal pathogens and/or (iv) the specific detection and identification of antibiotic resistance genes. All of the above types of DNA-based assays may be performed directly from any type of clinical specimens or from a microbial culture.

In our co-pending U.S. Ser. No. 08/526,840 and PCT (PCT/CA/95/00528) patent applications, we described DNA sequences suitable for (i) the species-specific detection and identification of 12 clinically important bacterial pathogens, (ii) the universal detection of bacteria, and (iii) the detection of 17 antibiotic resistance genes. This co-pending application described proprietary DNA sequences and DNA sequences selected from databases (in both cases, fragments of at least 100 base pairs), as well as oligonucleotide probes and amplification primers derived from these sequences. All the nucleic acid sequences described in this patent application enter the composition of diagnostic kits and methods capable of a) detecting the presence of bacteria, b) detecting specifically the presence of 12 bacterial species and 17 antibiotic resistance genes. However, these methods and kits need to be improved, since the ideal kit and method should be capable of diagnosing close to 100% of microbial pathogens and antibiotic resistance genes. For example, infections caused by *Enterococcus faecium* have become a clinical problem because of its resistance to many antibiotics. Both the detection of these bacteria and the evaluation of their resistance profiles are desirable. Besides that, novel DNA sequences (probes and primers) capable of recognizing the same and other microbial pathogens or the same and additional antibiotic resistance genes are also desirable to aim at detecting more target genes and complement our earlier patent application.

STATEMENT OF THE INVENTION

It is an object of the present invention to provide a specific, ubiquitous and sensitive method using probes and/or amplification primers for determining the presence and/or amount of nucleic acids:

from specific microbial species or genera selected from the group consisting of *Streptococcus* species, *Streptococcus agalactiae, Staphylococcus* species, *Staphylococcus saprophyticus, Enterococcus* species, *Enterococcus faecium, Neisseria* species, *Neisseria meningitidis, Listeria monocytogenes, Candida* species and *Candida albicans* from an antibiotic resistance gene selected from the group consisting of $bla_{tem}$, $bla_{rob}$, $bla_{shv}$, $bla_{oxa}$, blaZ, aadB, aacC1, aacC2, aacC3, aacA4, aac6'-IIa, ermA, ermB, ermC, mecA, vanA, vanB, vanC, satA, aac(6')-aph(2''), aad(6'), vat, vga, msrA, sul and int, and optionally, from any bacterial species in any sample suspected of containing said nucleic acids, wherein each of said nucleic acids or a variant or part thereof comprises a selected target region hybridizable with said probe or primers;

said method comprising the steps of contacting said sample with said probes or primers and detecting the presence and/or amount of hybridized probes or amplified products as an indication of the presence and/or amount of said any bacterial species, specific microbial species or genus and antibiotic resistance gene.

In a specific embodiment, a similar method directed to each specific microbial species or genus detection and identification, antibiotic resistance genes detection, and universal bacterial detection, separately, is provided.

In a more specific embodiment, the method makes use of DNA fragments (proprietary fragments and fragments obtained from databases), selected for their capacity to sensitively, specifically and ubiquitously detect the targeted bacterial or fungal nucleic acids.

In a particularly preferred embodiment, oligonucleotides of at least 12 nucleotides in length have been derived from the longer DNA fragments, and are used in the present method as probes or amplification primers.

The proprietary oligonucleotides (probes and primers) are also another object of the invention.

Diagnostic kits comprising probes or amplification primers for the detection of a microbial species or genus selected from the group consisting of *Streptococcus* species, *Streptococcus agalactiae, Staphylococcus* species, *Staphylococcus saprophyticus, Enterococcus* species, *Enterococcus faecium, Neisseria* species, *Neisseria meningitidis, Listeria monocytogenes, Candida* species and *Candida albicans* are also objects of the present invention.

Diagnostic kits further comprising probes or amplification primers for the detection of an antibiotic resistance gene selected from the group consisting of $bla_{tem}$, $bla_{rob}$, $bla_{shv}$, $bla_{oxa}$, blaZ, aadB, aacC1, aacC2, aacC3, aacA4, aac6'-IIa, ermA, ermB, ermC, mecA, vanA, vanB, vanC, satA, aac(6)-aph(2'), aad(6), vat, vga, msrA, sul and int are also objects of this invention.

Diagnostic kits further comprising probes or amplification primers for the detection of any bacterial or fungal species, comprising or not comprising those for the detection of the specific microbial species or genus listed above, and further comprising or not comprising probes and primers for the antibiotic resistance genes listed above, are also objects of this invention.

In a preferred embodiment, such a kit allows for the separate or the simultaneous detection and identification of the above-listed microbial species or genus, antibiotic resistance genes and for the detection of any bacterium.

In the above methods and kits, amplification reactions may include a) polymerase chain reaction (PCR), b) ligase chain reaction, c) nucleic acid sequence-based amplification, d) self-sustained sequence replication, e) strand displacement amplification, f) branched DNA signal amplification, g) transcription-mediated amplification, h) cycling probe technology (CPT) i) nested PCR, or j) multiplex PCR.

In a preferred embodiment, a PCR protocol is used as an amplification reaction.

In a particularly preferred embodiment, a PCR protocol is provided, comprising, for each amplification cycle, an annealing step of 30 seconds at 45-55° C. and a denaturation step of only one second at 95° C., without any time allowed specifically for the elongation step. This PCR protocol has been standardized to be suitable for PCR reactions with all selected primer pairs, which greatly facilitates the testing because each clinical sample can be tested with universal, species-specific, genus-specific and antibiotic resistance gene PCR primers under uniform cycling conditions. Furthermore, various combinations of primer pairs may be used in multiplex PCR assays.

We aim at developing a rapid test or kit to discard rapidly all the samples which are negative for bacterial cells and to subsequently detect and identify the above bacterial and/or fungal species and genera and to determine rapidly the bacterial resistance to antibiotics. Although the sequences from the selected antibiotic resistance genes are available from databases and have been used to develop DNA-based tests for their detection, our approach is unique because it represents a major improvement over current gold standard diagnostic methods based on bacterial cultures. Using an amplification method for the simultaneous bacterial detection and identification and antibiotic resistance genes detection, there is no need for culturing the clinical sample prior to testing. Moreover, a modified PCR protocol has been developed to detect all target DNA sequences in approximately one hour under uniform amplification conditions. This procedure will save lives by optimizing treatment, will diminish antibiotic resistance because less antibiotics will be prescribed, will reduce the use of broad spectrum antibiotics which are expensive, decrease overall health care costs by preventing or shortening hospitalizations, and decrease the time and costs associated with clinical laboratory testing.

In the methods and kits described herein below, the oligonucleotide probes and amplification primers have been derived from larger sequences (i.e. DNA fragments of at least 100 base pairs). All DNA fragments have been obtained either from proprietary fragments or from databases. DNA fragments selected from databases are newly used in a method of detection according to the present invention, since they have been selected for their diagnostic potential.

It is clear to the individual skilled in the art that other oligonucleotide sequences appropriate for (i) the universal bacterial detection, (ii) the detection and identification of the above microbial species or genus and (iii) the detection of antibiotic resistance genes other than those listed in Annex VI may also be derived from the proprietary fragments or selected database sequences. For example, the oligonucleotide primers or probes may be shorter or longer than the ones we have chosen; they may also be selected anywhere else in the proprietary DNA fragments or in the sequences selected from databases; they may be also variants of the same oligonucleotide. If the target DNA or a variant thereof hybridizes to a given oligonucleotide, or if the target DNA or a variant thereof can be amplified by a given oligonucleotide PCR primer pair, the converse is also true; a given target DNA may hybridize to a variant oligonucleotide probe or be amplified by a variant oligonucleotide PCR primer. Alternatively, the oligonucleotides may be designed from any DNA fragment sequences for use in amplification methods other than PCR. Consequently, the core of this invention is the identification of universal, species-specific, genus-specific and resistance gene-specific genomic or non-genomic DNA fragments which are used as a source of specific and ubiquitous oligonucleotide probes and/or amplification primers. Although the selection and evaluation of oligonucleotides suitable for diagnostic purposes requires much effort, it is quite possible for the individual skilled in the art to derive, from the selected DNA fragments, oligonucleotides other than the ones listed in Annex VI which are suitable for diagnostic purposes. When a proprietary fragment or a database sequence is selected for its specificity and ubiquity, it increases the probability that subsets thereof will also be specific and ubiquitous.

Since a high percentage of clinical specimens are negative for bacteria (Table 3), DNA fragments having a high potential for the selection of universal oligonucleotide probes or primers were selected from proprietary and database sequences. The amplification primers were selected from a gene highly conserved in bacteria and fungi, and are used to detect the presence of any bacterial pathogen in clinical specimens in order to determine rapidly (approximately one hour) whether it is positive or negative for bacteria. The selected gene, designated tuf encodes a protein (EF-Tu) involved in the translational process during protein synthesis. The tuf gene sequence alignments used to derive the universal primers include both proprietary and database sequences (Example 1 and Annex I). This strategy allows the rapid screening of the numerous negative clinical specimens (around 80% of the specimens received, see Table 3) submitted for bacteriological testing. Tables 4, 5 and 6 provide a list of the bacterial or fungal species used to test the specificity of PCR primers and DNA probes. Table 7 gives a brief description of each species-specific, genus-specific and universal amplification assays which are objects of the present invention. Tables 8, 9 and 10 provide some relevant information about the proprietary and database sequences selected for diagnostic purposes.

DETAILED DESCRIPTION OF THE INVENTION

Development of Species-Specific, Genus-Specific, Universal and Antibiotic Resistance Gene-Specific DNA Probes and Amplification Primers for Microorganisms

Selection from Databases of Sequences Suitable for Diagnostic Purposes

In order to select sequences which are suitable for species-specific or genus-specific detection and identification of bacteria or fungi or, alternatively, for the universal detection of bacteria, the database sequences (GenBank, EMBL and Swiss-Prot) were chosen based on their potential for diagnostic purposes according to sequence information and computer analysis performed with these sequences. Initially, all sequence data available for the targeted microbial species or genus were carefully analyzed. The gene sequences which appeared the most promising for diagnostic purposes based on sequence information and on sequence comparisons with the corresponding gene in other microbial species or genera performed with the Genetics Computer Group (GCG, Wisconsin) programs were selected for testing by PCR. Optimal PCR amplification primers were chosen from the selected database sequences with the help of the Oligo™ 4.0 primer analysis software (National Biosciences Inc., Plymouth, Minn.). The chosen primers were tested in PCR assays for their specificity and ubiquity for the target microbial species or genus. In general, the identification of database sequences from which amplification primers suitable for species-specific or genus-specific detection and identification were selected involved the computer analysis and PCR testing of several candidate gene sequences before obtaining a primer pair which is specific and ubiquitous for the target microbial species or genus. Annex VI provides a list of selected specific and ubiquitous PCR primer pairs. Annexes I to V and Examples 1 to 4 illustrate the strategy used to select genus-specific, species-specific and universal PCR primers from tuf sequences or from the recA gene.

Oligonucleotide Primers and Probes Design and Synthesis

The DNA fragments sequenced by us or selected from databases (GenBank and EMBL) were used as sources of oligonucleotides for diagnostic purposes. For this strategy, an array of suitable oligonucleotide primers or probes derived from a variety of genomic DNA fragments (size of more than 100 bp) selected from databases were tested for their specificity and ubiquity in PCR and hybridization assays as described later. It is important to note that the database sequences were selected based on their potential for being species-specific, genus-specific or universal for the detection of bacteria or fungi according to available sequence information and extensive analysis and that, in general, several candidate database sequences had to be tested in order to obtain the desired specificity, ubiquity and sensitivity.

Oligonucleotide probes and amplification primers derived from species-specific fragments selected from database sequences were synthesized using an automated DNA synthesizer (Perkin-Elmer Corp., Applied Biosystems Division). Prior to synthesis, all oligonucleotides (probes for hybridization and primers for DNA amplification) were evaluated for their suitability for hybridization or DNA amplification by polymerase chain reaction (PCR) by computer analysis using standard programs (i.e. the Genetics Computer Group (GCG) programs and the primer analysis software Oligo™ 4.0). The potential suitability of the PCR primer pairs was also evaluated prior to the synthesis by verifying the absence of unwanted features such as long stretches of one nucleotide and a high proportion of G or C residues at the 3' end (Persing et al., 1993, Diagnostic Molecular Microbiology: Principles and Applications, American Society for Microbiology, Washington, D.C.).

The oligonucleotide primers or probes may be derived from either strand of the duplex DNA. The primers or probes may consist of the bases A, G, C, or T or analogs and they may be degenerated at one or more chosen nucleotide position(s). The primers or probes may be of any suitable length and may be selected anywhere within the DNA sequences from proprietary fragments or from selected database sequences which are suitable for (i) the universal detection of bacteria, (ii) the species-specific detection and identification of *Enterococcus faecium, Listeria monocytogenes, Neisseria meningitidis, Staphylococcus saprophyticus, Streptococcus agalactiae* and *Candida albicans* (iii) the genus-specific detection of *Streptococcus* species, *Enterococcus* species, *Staphylococcus* species and *Neisseria* species or (iv) the detection of the 26 above-mentioned clinically important antibiotic resistance genes.

Variants for a given target bacterial gene are naturally occurring and are attributable to sequence variation within that gene during evolution (Watson et al., 1987, Molecular Biology of the Gene, 4$^{th}$ ed., The Benjamin/Cummings Publishing Company, Menlo Park, Calif.; Lewin, 1989, Genes IV, John Wiley & Sons, New York, N.Y.). For example, different strains of the same bacterial species may have a single or more nucleotide variation(s) at the oligonucleotide hybridization site. The person skilled in the art is well aware of the existence of variant bacterial or fungal DNA sequences for a specific gene and that the frequency of sequence variations depends on the selective pressure during evolution on a given gene product. The detection of a variant sequence for a region between two PCR primers may be demonstrated by sequencing the amplification product. In order to show the presence of sequence variants at the primer hybridization site, one has to amplify a larger DNA target with PCR primers outside that hybridization site. Sequencing of this larger fragment will allow the detection of sequence variation at this site. A similar strategy may be applied to show variants at the hybridization site of a probe. Insofar as the divergence of the target sequences or a part thereof does not affect the specificity and ubiquity of the amplification primers or probes, variant bacterial DNA is under the scope of this invention. Variants of the selected primers or probes may also be used to amplify or hybridize to a variant DNA.

Sequencing of Tuf Sequences from a Variety of Bacterial and Fungal Species

The nucleotide sequence of a portion of tuf genes was determined for a variety of bacterial and fungal species. The amplification primers SEQ ID NOs: 107 and 108, which amplify a tuf gene portion of approximately 890 bp, were used for the sequencing of bacterial tuf sequences. The amplification primers SEQ ID NOs: 109 and 172, which amplify a tuf gene portion of approximately 830 bp, were used for the sequencing of fungal tuf sequences. Both primer pairs can amplify tufA and tufB genes. This is not surprising because these two genes are nearly identical. For example, the entire tufA and tufB genes from *E. coli* differ at only 13 nucleotide positions (Neidhardt et al., 1996, *Escherichia coli* and *Salmonella*: Cellular and Molecular Biology, 2$^{nd}$ ed., American Society for Microbiology Press, Washington, D.C.). These amplification primers are degenerated at several nucleotide positions and contain inosines in order to allow the amplification of a wide range of tuf sequences. The strategy used to select these amplification primers is similar to that illustrated in Annex I for the selection of universal primers. The amplification primers SEQ ID NOs: 107 and 108 could be used to amplify the tuf genes from any bacterial species. The amplification primers SEQ ID NOs: 109 and 172 could be used to amplify the tuf genes from any fungal species.

The tuf genes were amplified directly from bacterial or yeast cultures using the following amplification protocol: One µL of cell suspension was transferred directly to 19 µL of a PCR reaction mixture containing 50 mM KCl, 10 mM Tris-HCl (pH 9.0), 0.1% Triton X-100, 2.5 mM $MgCl_2$, 1 µM of each of the 2 primers, 200 µM of each of the four dNTPs, 0.5 unit of Taq DNA polymerase (Promega Corp., Madison, Wis.). PCR reactions were subjected to cycling using a MJ Research PTC-200 thermal cycler (MJ Research Inc., Watertown, Mass.) as follows: 3 min at 96° C. followed by 30-35 cycles of 1 min at 95° C. for the denaturation step, 1 min at 30-50° C. for the annealing step and 1 min at 72° C. for the extension step. Subsequently, twenty microliters of the PCR-amplified mixture were resolved by electrophoresis in a 1.5% agarose gel. The gel was then visualized by staining with methylene blue (Flores et al., 1992, Biotechniques, 13:203-205). The size of the amplification products was estimated by comparison with a 100-bp molecular weight ladder. The band corresponding to the specific amplification product (i.e. approximately 890 or 830 bp for bacterial or fungal tuf sequences, respectively) was excised from the agarose gel and purified using the QIAquick™ gel extraction kit (QIAGEN Inc., Chatsworth, Calif.). The gel-purified DNA fragment was then used directly in the sequencing protocol. Both strands of the tuf genes amplification product were sequenced by the dideoxynucleotide chain termination sequencing method by using an Applied Biosystems automated DNA sequencer (model 373A) with their PRISM™ Sequenase® Terminator Double-stranded DNA Sequencing Kit (Perkin-Elmer Corp., Applied Biosystems Division, Foster City, Calif.). The sequencing reactions were all performed by using the amplification primers (SEQ ID NOs: 107 to 109 and 172) and 100 ng per reaction of the gel-purified amplicon. In order to ensure that the determined sequence did not contain errors attributable to the sequencing of PCR artefacts, we have sequenced two preparations of the gel-purified tuf amplification product originating from two independent PCR amplifications. For all target microbial species, the sequences determined for both amplicon preparations were identical.

Furthermore, the sequences of both strands were 100% complementary thereby confirming the high accuracy of the determined sequence. The tuf sequences determined using the above strategy are all in the Sequence Listing (i.e. SEQ ID NOs: 118 to 146). Table 13 gives the originating microbial species and the source for each tuf sequence in the Sequence Listing.

The alignment of the tuf sequences determined by us or selected from databases reveals clearly that the length of the sequenced portion of the tuf genes is variable. There may be insertions or deletions of several amino acids. This explains why the size of the sequenced tuf amplification product was variable for both bacterial and fungal species. Among the tuf sequences determined by our group, we found insertions and deletions adding up to 5 amino acids or 15 nucleotides. Consequently, the nucleotide positions indicated on top of each of Annexes I to V do not correspond for tuf sequences having insertions or deletions.

It should also be noted that the various tuf sequences determined by us occasionally contain degenerescences. These degenerated nucleotides correspond to sequence variations between tufA and tufB genes because the amplification primers amplify both tuf genes. These nucleotide variations were not attributable to nucleotide misincorporations by the taq DNA polymerase because the sequence of both strands were identical and also because the sequences determined with both preparations of the gel-purified tuf amplicons were identical.

The Selection of Amplification Primers from Tuf Sequences

The tuf sequences determined by us or selected from databases were used to select PCR primers for (i) the universal detection of bacteria, (ii) the genus-specific detection and identification of *Enterococcus* spp. and *Staphylococcus* spp. and (iii) the species-specific detection and identification of *Candida albicans*. The strategy used to select these PCR primers was based on the analysis of multiple sequence alignments of various tuf sequences. For more details about the selection of PCR primers from tuf sequences, please refer to Examples 1 to 3 and Annexes I to IV.

The Selection of Amplification Primers from recA

The comparison of the nucleotide sequence for the recA gene from various bacterial species including 5 species of streptococci allowed the selection of *Streptococcus*-specific PCR primers. For more details about the selection of PCR primers from recA, please refer to Example 4 and Annex V.

DNA Fragment Isolation from *Staphylococcus saprophyticus* by Arbitrarily Primed PCR DNA sequences of unknown coding potential for the species-specific detection and identification of *Staphylococcus saprophyticus* were obtained by the method of arbitrarily primed PCR (AP-PCR).

AP-PCR is a method which can be used to generate specific DNA probes for microorganisms (Fani et al., 1993, Mol. Ecol. 2:243-250). A description of the AP-PCR protocol used to isolate a species-specific genomic DNA fragment from *Staphylococcus saprophyticus* follows. Twenty different oligonucleotide primers of 10 nucleotides in length (all included in the AP-PCR kit OPAD (Operon Technologies, Inc., Alameda, Calif.)) were tested systematically with DNAs from 3 bacterial strains of *Staphylococcus saprophyticus* (all obtained from the American Type Culture Collection (ATCC): numbers 15305, 35552 and 43867) as well as with DNA from four other *staphylococcal* species (*Staphylococcus aureus* ATCC 25923, *Staphylococcus epidermidis* ATCC 14990, *Staphylococcus haemolyticus* ATCC 29970 and *Staphylococcus hominis* ATCC 35982). For all bacterial species, amplification was performed from a bacterial suspension adjusted to a standard 0.5 McFarland which corresponds to approximately $1.5\times10^8$ bacteria/mL. One μL of the standardized bacterial suspension was transferred directly to 19 μL of a PCR reaction mixture containing 50 mM KCl, 10 mM Tris-HCl (pH 9.0), 0.1% Triton X-100, 2.5 mM $MgCl_2$, 1.2 μM of only one of the 20 different AP-PCR primers OPAD, 200 μM of each of the four dNTPs and 0.5 unit of Taq DNA polymerase (Promega Corp., Madison, Wis.). PCR reactions were subjected to cycling using a MJ Research PTC-200 thermal cycler (MJ Research Inc.) as follows: 3 min at 96° C. followed by 35 cycles of 1 min at 95° C. for the denaturation step, 1 min at 32° C. for the annealing step and 1 min at 72° C. for the extension step. A final extension step of 7 min at 72° C. was made after the 35 cycles to ensure complete extension of PCR products. Subsequently, twenty microliters of the PCR amplified mixture were resolved by electrophoresis in a 2% agarose gel containing 0.25 μg/mL of ethidium bromide. The size of the amplification products was estimated by comparison with a 50-bp molecular weight ladder.

Amplification patterns specific for *Staphylococcus saprophyticus* were observed with the AP-PCR primer OPAD-9 (SEQ ID NO: 25). Amplification with this primer consistently showed a band corresponding to a DNA fragment of approximately 450 bp for all *Staphylococcus saprophyticus* strains tested but not for any of the four other *staphylococcal* species tested. This species-specific pattern was confirmed by testing 10 more clinical isolates of *S. saprophyticus* selected from the culture collection of the microbiology laboratory of the CHUL as well as strains selected from the gram-positive bacterial species listed in Table 5.

The band corresponding to the approximately 450 bp amplicon which was specific and ubiquitous for *S. saprophyticus* based on AP-PCR was excised from the agarose gel and purified using the QIAquick™ gel extraction kit (QIAGEN Inc.). The gel-purified DNA fragment was cloned into the T/A cloning site of the pCR 2.1™ plasmid vector (Invitrogen Inc.) using T4 DNA ligase (New England BioLabs). Recombinant plasmids were transformed into *E. coli* DH5α competent cells using standard procedures. Plasmid DNA isolation was done by the method of Bimboim and Doly (Nucleic Acids Res. 7:1513-1523) for small-scale preparations. All plasmid DNA preparations were digested with the EcoRI restriction endonuclease to ensure the presence of the approximately 450 bp AP-PCR insert into the recombinant plasmids. Subsequently, a large-scale and highly purified plasmid DNA preparation was performed from two selected clones shown to carry the AP-PCR insert by using the QIAGEN plasmid purification kit. These plasmid preparations were used for automated DNA sequencing.

Both strands of the AP-PCR insert from the two selected clones were sequenced by the dideoxynucleotide chain termination sequencing method with SP6 and T7 sequencing primers, by using an Applied Biosystems automated DNA sequencer as described previously. The analysis of the obtained sequences revealed that the DNA sequences for both strands from each clone were 100% complementary. Furthermore, it showed that the entire sequence determined for each clone were both identical. These sequencing data confirm the 100% accuracy for the determined 438 bp sequence (SEQ ID NO: 29). Optimal amplification primers have been selected from the sequenced AP-PCR *Staphylococcus saprophyticus* DNA fragment with the help of the primer analysis software Oligo™ 4.0. The selected primer sequences have been tested in PCR assays to verify their specificity and ubiquity (Table 7). These PCR primers were specific since there was no amplification with DNA from bacterial species other than *S.*

*saprophyticus* selected from Tables 4 and 5. Furthermore, this assay was ubiquitous since 245 of 260 strains of *S. saprophyticus* were efficiently amplified with this PCR assay. When used in combination with another *S. saprophyticus*-specific PCR assay, which is an object of our co-pending U.S. Ser. No. 08/526,840 and PCT (PCT/CA/95/00528) patent applications, the ubiquity reaches 100% for these 260 strains.

DNA Amplification

For DNA amplification by the widely used PCR (polymerase chain reaction) method, primer pairs were derived from proprietary DNA fragments or from database sequences. Prior to synthesis, the potential primer pairs were analyzed by using the Oligo™ 4.0 software to verify that they are good candidates for PCR amplification.

During DNA amplification by PCR, two oligonucleotide primers binding respectively to each strand of the heat-denatured target DNA from the bacterial genome are used to amplify exponentially in vitro the target DNA by successive thermal cycles allowing denaturation of the DNA, annealing of the primers and synthesis of new targets at each cycle (Persing et al, 1993, Diagnostic Molecular Microbiology: Principles and Applications, American Society for Microbiology, Washington, D.C.).

Briefly, the PCR protocols were as follow: Treated clinical specimens or standardized bacterial or fungal suspensions (see below) were amplified in a 20 μL PCR reaction mixture containing 50 mM KCl, 10 mM Tris-HCl (pH 9.0), 2.5 mM $MgCl_2$, 0.4 μM of each primer, 200 μM of each of the four dNTPs and 0.5 unit of Taq DNA polymerase (Promega) combined with the TaqStart™ antibody (Clontech Laboratories Inc., Palo Alto, Calif.). The TaqStart™ antibody, which is a neutralizing monoclonal antibody to Taq DNA polymerase, was added to all PCR reactions to enhance the specificity and the sensitivity of the amplifications (Kellogg et al., 1994, Biotechniques 16:1134-1137). The treatment of the clinical specimens varies with the type of specimen tested, since the composition and the sensitivity level required are different for each specimen type. It consists in a rapid protocol to lyse the bacterial cells and eliminate the PCR inhibitory effects (see example 11 for urine specimen preparation). For amplification from bacterial or fungal cultures, the samples were added directly to the PCR amplification mixture without any pre-treatment step (see example 10). Primer sequences derived from highly conserved regions of the bacterial 16S ribosomal RNA gene were used to provide an internal control for all PCR reactions. Alternatively, the internal control was derived from sequences not found in microorganisms or in the human genome. The internal control was integrated into all amplification reactions to verify the efficiency of the PCR assays and to ensure that significant PCR inhibition was absent. The internal control derived from rRNA was also useful to monitor the efficiency of bacterial lysis protocols.

PCR reactions were then subjected to thermal cycling (3 min at 95° C. followed by 30 cycles of 1 second at 95° C. for the denaturation step and 30 second at 55° C. for the annealing-extension step) using a PTC-200 thermal cycler (MJ Research Inc.) and subsequently analyzed by standard ethidium bromide-stained agarose gel electrophoresis. The number of cycles performed for the PCR assays varies according to the sensitivity level required. For example, the sensitivity level required for microbial detection directly from clinical specimens is higher for blood specimens than for urine specimens because the concentration of microorganisms associated with a septicemia can be much lower than that associated with a urinary tract infection. Consequently, more sensitive PCR assays having more thermal cycles are required for direct detection from blood specimens. Similarly, PCR assays performed directly from bacterial or fungal cultures may be less sensitive than PCR assays performed directly from clinical specimens because the number of target organisms is normally much lower in clinical specimens than in microbial cultures.

It is clear that other methods for the detection of specific amplification products, which may be faster and more practical for routine diagnosis, may be used. Such methods may be based on the detection of fluorescence after amplification (e.g. TaqMan™ system from Perkin Elmer or Amplisensor™ from Biotronics). Methods based on the detection of fluorescence are particularly promising for utilization in routine diagnosis as they are very rapid, quantitative and can be automated (Example 14).

Microbial pathogens detection and identification may also be performed by solid support or liquid hybridization using species-specific internal DNA probes hybridizing to an amplification product. Such probes may be generated from any species-specific or genus-specific DNA amplification products which are objects of the present invention. Alternatively, the internal probes for species or genus detection and identification may be derived from the amplicons produced by the universal amplification assay. The oligonucleotide probes may be labeled with biotin or with digoxigenin or with any other reporter molecules.

To assure PCR efficiency, glycerol, dimethyl sulfoxide (DMSO) or other related solvents can be used to increase the sensitivity of the PCR and to overcome problems associated with the amplification of a target DNA having a high GC content or forming strong secondary structures (Dieffenbach and Dveksler, 1995, PCR Primer: A Laboratory Manual, Cold Spring Harbor Laboratory Press, Plainview, N.Y.). The concentration ranges for glycerol and DMSO are 5-15% (v/v) and 3-10% (v/v), respectively. For the PCR reaction mixture, the concentration ranges for the amplification primers and $MgCl_2$ are 0.1-1.5 μM and 1.5-3.5 mM, respectively. Modifications of the standard PCR protocol using external and nested primers (i.e. nested PCR) or using more than one primer pair (i.e. multiplex PCR) may also be used (Persing et al., 1993, Diagnostic Molecular Microbiology: Principles and Applications, American Society for Microbiology, Washington, D.C.). For more details about the PCR protocols and amplicon detection methods, see Examples 9 to 14.

The person skilled in the art of DNA amplification knows the existence of other rapid amplification procedures such as ligase chain reaction (LCR), transcription-mediated amplification (TMA), self-sustained sequence replication (3SR), nucleic acid sequence-based amplification (NASBA), strand displacement amplification (SDA), branched DNA (bDNA) and cycling probe technology (CPT) (Lee et al., 1997, Nucleic Acid Amplification Technologies: Application to Disease Diagnosis, Eaton Publishing, Boston, Mass.; Persing et al., 1993, Diagnostic Molecular Microbiology: Principles and Applications, American Society for Microbiology, Washington, D.C.). The scope of this invention is not limited to the use of amplification by PCR, but rather includes the use of any rapid nucleic acid amplification method or any other procedure which may be used to increase rapidity and sensitivity of the tests. Any oligonucleotide suitable for the amplification of nucleic acids by approaches other than PCR and derived from the species-specific, genus-specific and universal DNA fragments as well as from selected antibiotic resistance gene sequences included in this document are also under the scope of this invention.

Hybridization Assays with Oligonucleotide Probes

In hybridization experiments, single-stranded oligonucleotides (size less than 100 nucleotides) have some advantages over DNA fragment probes for the detection of bacteria, such as ease of synthesis in large quantities, consistency in results from batch to batch and chemical stability. Briefly, for the hybridizations, oligonucleotides were 5' end-labeled with the radionucleotide $\gamma$-$^{32}$P(dATP) using T4 polynucleotide kinase (Pharmacia) (Sambrook et al., 1989, Molecular Cloning: A Laboratory Manual, 2$^{nd}$ ed., Cold Spring Harbor Laboratory Press, Cold Spring Harbor, N.Y.). The unincorporated radionucleotide was removed by passing the labeled oligonucleotide through a Sephadex G-50™ column. Alternatively, oligonucleotides were labeled with biotin, either enzymatically at their 3' ends or incorporated directly during synthesis at their 5' ends, or with digoxigenin. It will be appreciated by the person skilled in the art that labeling means other than the three above labels may be used.

Each oligonucleotide probe was then tested for its specificity by hybridization to DNAs from a variety of bacterial and fungal species selected from Tables 4, 5 and 6. All of the bacterial or fungal species tested were likely to be pathogens associated with common infections or potential contaminants which can be isolated from clinical specimens. Each target DNA was released from bacterial cells using standard chemical treatments to lyse the cells (Sambrook et al., 1989, Molecular Cloning: A Laboratory Manual, 2$^{nd}$ ed., Cold Spring Harbor Laboratory Press, Cold Spring Harbor, N.Y.). Subsequently, the DNA was denatured by conventional methods and then irreversibly fixed onto a solid support (e.g. nylon or nitrocellulose membranes) or free in solution. The fixed single-stranded target DNAs were then hybridized with the oligonucleotide probe cells (Sambrook et al., 1989, Molecular Cloning: A Laboratory Manual, 2$^{nd}$ ed., Cold Spring Harbor Laboratory Press, Cold Spring Harbor, N.Y.). Pre-hybridization conditions were in 1 M NaCl+10% dextran sulfate+1% SDS+100 μg/mL salmon sperm DNA at 65° C. for 15 min. Hybridization was performed in fresh pre-hybridization solution containing the labeled probe at 65° C. overnight. Post-hybridization washing conditions were as follows: twice in 3×SSC containing 1% SDS, twice in 2×SSC containing 1% SDS and twice in 1×SSC containing 1% SDS (all of these washes were at 65° C. for 15 min), and a final wash in 0.1×SSC containing 1% SDS at 25° C. for 15 min. Autoradiography of washed filters allowed the detection of selectively hybridized probes. Hybridization of the probe to a specific target DNA indicated a high degree of similarity between the nucleotide sequence of these two DNAs because of the high stringency of the washes.

An oligonucleotide probe was considered specific only when it hybridized solely to DNA from the species or genus from which it was isolated. Oligonucleotide probes found to be specific were subsequently tested for their ubiquity (i.e. ubiquitous probes recognized most or all isolates of the target species or genus) by hybridization to microbial DNAs from clinical isolates of the species or genus of interest including ATCC strains. The DNAs from strains of the target species or genus were denatured, fixed onto nylon membranes and hybridized as described above. Probes were considered ubiquitous when they hybridized specifically with the DNA from at least 80% of the isolates of the target species or genus.

Specificity and Ubiquity Tests for Oligonucleotide Primers and Probes

The specificity of oligonucleotide primers and probes, derived either from the DNA fragments sequenced by us or selected from databases, was tested by amplification of DNA or by hybridization with bacterial or fungal species selected from those listed in Tables 4, 5 and 6, as described in the two previous sections. Oligonucleotides found to be specific were subsequently tested for their ubiquity by amplification (for primers) or by hybridization (for probes) with bacterial DNAs from isolates of the target species or genus. Results for specificity and ubiquity tests with the oligonucleotide primers are summarized in Table 7. The specificity and ubiquity of the PCR assays using the selected amplification primer pairs were tested directly from cultures (see Examples 9 and 10) of bacterial or fungal species.

The various species-specific and genus-specific PCR assays which are objects of the present invention are all specific. For the PCR assays specific to bacterial species or genus, this means that DNA isolated from a wide variety of bacterial species, other than that from the target species or genus and selected from Tables 4 and 5, could not be amplified. For the PCR assay specific to *Candida albicans*, it means there was no amplification with genomic DNA from the fungal species listed in Table 6 as well as with a variety of bacterial species selected from Tables 4 and 5.

The various species-specific and genus-specific PCR assays which are objects of the present invention are also all ubiquitous (Table 7). (i) The species-specific PCR assays for *E. faecium, L. monocytogenes, S. saprophyticus, S. agalactiae* and *C. albicans* amplified genomic DNA from all or most strains of the target species tested, which were obtained from various sources and which are representative of the diversity within each target species (Table 7). The species identification of all of these strains was based on classical biochemical methods which are routinely used in clinical microbiology laboratories. (ii) The genus-specific PCR assays specific for *Enterococcus* spp., *Staphylococcus* spp., *Streptococcus* spp. and *Neisseria* spp. amplified genomic DNA from all or most strains of the target genus tested, which represent all clinically important bacterial species for each target genus. These strains were obtained from various sources and are representative of the diversity within each target genus. Again, the species identification of all of these strains was based on classical biochemical methods which are routinely used in clinical microbiology laboratories. More specifically, the four genus-specific PCR assays amplified the following species: (1) The Enterococcus-specific assay amplified efficiently DNA from all of the 11 enterococcal species tested including *E. avium, E. casseliflavus, E. dispar, E. durans, E. faecalis, E. faecium, E. flavescens, E. gallinarum, E. hirae, E. mundtii* and *E. raffinosus*. (2) The *Neisseria*-specific assay amplified efficiently DNA from all of the 12 *neisserial* species tested including *N. canis, N. cinerea, N. elongata, N. flavescens, N. gonorrhoeae, N. lactamica, N. meningitidis, N. mucosa, N. polysaccharea, N. sicca, N. subflava* and *N. weaveri*. (3) The *Staphylococcus*-specific assay amplified efficiently DNA from 13 of the 14 *staphylococcal* species tested including *S. aureus, S. auricularis, S. capitis, S. cohnii, S. epidermidis, S. haemolyticus, S. hominis, S. lugdunensis, S. saprophyticus, S. schleiferi, S. simulans, S. warneri* and *S. xylosus*. The *staphylococcal* species which could not be amplified is *S. sciuri*. (4) Finally, the *Streptococcus*-specific assay amplified efficiently DNA from all of the 22 *streptococcal* species tested including *S. agalactiae, S. anginosus, S. bovis, S. constellatus, S. crista, S. dysgalactiae, S. equi, S. gordonii, S. intermedius, S. mitis, S. mutans, S. oralis, S. parasanguis, S. pneumoniae, S. pyogenes, S. salivarius, S. sanguis, S. sabrinus, S. suis, S. uberis, S. vestibularis* and *S. viridans*. On the other hand, the *Streptococcus*-specific assay did not amplify 3 out of 9 strains of *S. mutans* and 1 out of 23 strains of *S. salivarius*, thereby showing a slight lack of ubiquity for these two *streptococcal* species.

All specific and ubiquitous amplification primers for each target microbial species or genus or antibiotic resistance gene investigated are listed in Annex VI. Divergence in the sequenced DNA fragments can occur, insofar as the divergence of these sequences or a part thereof does not affect the specificity of the probes or amplification primers. Variant bacterial DNA is under the scope of this invention.

The PCR amplification primers listed in Annex VI were all tested for their specificity and ubiquity using reference strains as well as clinical isolates from various geographical locations. The 351 reference strains used to test the amplification and hybridization assays (Tables 4, 5 and 6) were obtained from (i) the American Type Culture Collection (ATCC): 85%, (ii) the Laboratoire de santé publique du Québec (LSPQ): 10%, (iii) the Centers for Disease Control and Prevention (CDC): 3%, (iv) the National Culture Type Collection (NCTC): 1% and (v) several other reference laboratories throughout the world: 1%. These reference strains are representative of (i) 90 gram-negative bacterial species (169 strains; Table 4), (ii) 97 gram-positive bacterial species (154 strains; Table 5) and (iii) 12 fungal species (28 strains; Table 6).

Antibiotic Resistance Genes

Antimicrobial resistance complicates treatment and often leads to therapeutic failures. Furthermore, overuse of antibiotics inevitably leads to the emergence of bacterial resistance. Our goal is to provide clinicians, in approximately one hour, the needed information to prescribe optimal treatments. Besides the rapid identification of negative clinical specimens with DNA-based tests for universal bacterial detection and the identification of the presence of a specific pathogen in the positive specimens with species- and/or genus-specific DNA-based tests, clinicians also need timely information about the ability of the bacterial pathogen to resist antibiotic treatments. We feel that the most efficient strategy to evaluate rapidly bacterial resistance to antimicrobials is to detect directly from the clinical specimens the most common and clinically important antibiotic resistance genes (i.e. DNA-based tests for the detection of antibiotic resistance genes). Since the sequence from the most important and common bacterial antibiotic resistance genes are available from databases, our strategy was to use the sequence from a portion or from the entire resistance gene to design specific oligonucleotide primers or probes which will be used as a basis for the development of rapid DNA-based tests. The sequence from each of the bacterial antibiotic resistance genes selected on the basis of their clinical relevance (i.e. high incidence and importance) is given in the Sequence Listing. Tables 9 and 10 summarize some characteristics of the selected antibiotic resistance genes. Our approach is unique because the antibiotic resistance genes detection and the bacterial detection and identification are performed simultaneously in multiplex assays under uniform PCR amplification conditions (Example 13).

Annex VI provides a list of all amplification primers selected from 26 clinically important antibiotic resistance genes which were tested in PCR assays. The various PCR assays for antibiotic resistance genes detection and identification were validated by testing several resistant bacterial isolates known to carry the targeted gene and obtained from various countries. The testing of a large number of strains which do not carry the targeted resistance gene was also performed to ensure that all assays were specific. So far, all PCR assays for antibiotic resistance genes are highly specific and have detected all control resistant bacterial strains known to carry the targeted gene. The results of some clinical studies to validate the array of PCR assays for the detection and identification of antibiotic resistance genes and correlate these DNA-based assays with standard antimicrobials susceptibility testing methods are presented in Tables 11 and 12.

Universal Bacterial Detection

In the routine microbiology laboratory, a high percentage of clinical specimens sent for bacterial identification are negative by culture (Table 4). Testing clinical samples with universal amplification primers or universal probes to detect the presence of bacteria prior to specific identification and screen out the numerous negative specimens is thus useful as it saves costs and may rapidly orient the clinical management of the patients. Several amplification primers and probes were therefore synthesized from highly conserved portions of bacterial sequences from the tuf genes (Table 8). The universal primer selection was based on a multiple sequence alignment constructed with sequences determined by us or selected from available database sequences as described in Example 1 and Annex I.

For the identification of database sequences suitable for the universal detection of bacteria, we took advantage of the fact that the complete genome sequences for two distant microorganisms (i.e. *Mycoplasma genitalium* and *Haemophilus influenzae*) are available. A comparison of the amino acid sequence for all proteins encoded by the genome of these two distant microorganisms led to the identification of highly homologous proteins. An analysis of these homologous proteins allowed to select some promising candidates for the development of universal DNA-based assays for the detection of bacteria. Since the complete nucleotide sequence of several other microbial genomes are presently available in databases, a person skilled in the art could arrive to the same conclusions by comparing genomes sequences other than those of *Mycoplasma genitalium* and *Haemophilus influenzae*. The selected tuf gene encodes a protein (EF-Tu) involved in the translation process during protein synthesis. Subsequently, an extensive nucleotide sequence analysis was performed with the tuf gene sequences available in databases as well as with novel tuf sequences which we have determined as described previously. All computer analysis of amino acid and nucleotide sequences were performed by using the GCG programs. Subsequently, optimal PCR primers for the universal amplification of bacteria were selected with the help of the Oligo™ program. The selected primers are degenerated at several nucleotide positions and contain several inosines in order to allow the amplification of all clinically relevant bacterial species (Annex I). Inosine is a nucleotide analog able to specifically bind to any of the four nucleotides A, C, G or T. Degenerated oligonucleotides consist of an oligonucleotide mix having two or more of the four nucleotides A, C, G or T at the site of mismatches. The inclusion of inosine and/or of degenerescences in the amplification primers allow mismatch tolerance thereby permitting the amplification of a wider array of target nucleotide sequences (Dieffenbach and Dveksler, 1995 PCR Primer: A Laboratory Manual, Cold Spring Harbor Laboratory Press, Plainview, N.Y.).

The amplification conditions with the universal primers were identical to those used for the species- and genus-specific amplification assays except that the annealing temperature was 50° C. instead of 55° C. This universal PCR assay was specific and nearly ubiquitous for the detection of bacteria. The specificity for bacteria was verified by amplifying genomic DNA isolated from the 12 fungal species listed in Table 6 as well as genomic DNA from *Leishmania donovani, Saccharomyces cerevisiae* and human lymphocytes. None of the above eukaryotic DNA preparations could be amplified by the universal assay, thereby suggesting that this test is specific for bacteria. The ubiquity of the universal assay was verified by amplifying genomic DNAs from 116 reference strains which represent 95 of the most clinically relevant bacterial species. These species have been selected from the bacterial species listed in Tables 4 and 5. We found that 104 of these 116 strains could be amplified. The bacterial species which could not be amplified belong to the following genera: *Corynebacterium* (11 species) and *Stenotrophomonas* (1 species). Sequencing of the tuf genes from these bacterial species has been recently performed. This sequencing data has been used to select new universal primers which may be more ubiquitous. These primers are in the process of being tested. We also observed that for several species the annealing temperature had to be reduced to 45° C. in order to get an efficient amplification. These bacterial species include *Gemella morbilbrum, Listeria* spp. (3 species) and *Gardnerella vaginalis*. It is important to note that the 95 bacterial species selected from Tables 4 and 5 to test the ubiquity of the universal assay include all of the most clinically relevant bacterial species associated with a variety of human infections acquired in the community or in hospitals (nosocomial infections). The most clinically important bacterial and fungal pathogens are listed in Tables 1 and 2.

Examples and Annexes

The following examples and annexes are intended to be illustrative of the various methods and compounds of the invention, rather than limiting the scope thereof.

The various annexes show the strategies used for the selection of amplification primers from tuf sequences or from the recA gene: (i) Annex I illustrates the strategy used for the selection of the universal amplification primers from tuf sequences. (ii) Annex II shows the strategy used for the selection of the amplification primers specific for the genus *Enterococcus* from tuf sequences. (iii) Annex III illustrates the strategy used for the selection of the amplification primers specific for the genus *Staphylococcus* from tuf sequences. (iv) Annex IV shows the strategy used for the selection of the amplification primers specific for the species *Candida albicans* from tuf sequences. (v) Annex V illustrates the strategy used for the selection of the amplification primers specific for the genus *Streptococcus* from recA sequences. (vi) Annex VI gives a list of all selected primer pairs. As shown in these annexes, the selected amplification primers may contain inosines and/or degenerescences. Inosine is a nucleotide analog able to specifically bind to any of the four nucleotides A, C, G or T. Alternatively, degenerated oligonucleotides which consist of an oligonucleotide mix having two or more of the four nucleotides A, C, G or T at the site of mismatches were used. The inclusion of inosine and/or of degenerescences in the amplification primers allow mismatch tolerance thereby permitting the amplification of a wider array of target nucleotide sequences (Dieffenbach and Dveksler, 1995 PCR Primer: A Laboratory Manual, Cold Spring Harbor Laboratory Press, Plainview, N.Y.).

EXAMPLES

Example 1

Selection of Universal PCR Primers from Tuf Sequences

As shown in Annex I, the comparison of tuf sequences from a variety of bacterial and eukaryotic species allowed the selection of PCR primers which are universal for the detection of bacteria. The strategy used to design the PCR primers was based on the analysis of a multiple sequence alignment of various tuf sequences. This multiple sequence alignment includes tuf sequences from 38 bacterial species and 3 eukaryotic species either determined by us or selected from databases (Table 13). A careful analysis of this multiple sequence alignment allowed the selection of primer sequences which are conserved within eubacteria but which discriminate sequences from eukaryotes, thereby permitting the universal detection of bacteria. As shown in Annex I, the selected primers contain several inosines and degenerescences. This was necessary because there is a relatively high polymorphism among bacterial tuf sequences despite the fact that this gene is highly conserved. In fact, among the tuf sequences that we determined, we found many nucleotide variations as well as some deletions and/or insertions of amino acids. The selected universal primers were specific and ubiquitous for bacteria (Table 7). Of the 95 most clinically important bacterial species tested, 12 were not amplified. These species belong to the genera *Corynebacterium* (11 species) and *Stenotrophomonas* (1 species). The universal primers did not amplify DNA of non-bacterial origin, including human and other types of eukaryotic DNA.

Example 2

Selection of Genus-Specific PCR Primers from Tuf Sequences

As shown in Annexes 2 and 3, the comparison of tuf sequences from a variety of bacterial species allowed the selection of PCR primers specific for *Enterococcus* spp. or for *Staphylococcus* spp. The strategy used to design the PCR primers was based on the analysis of a multiple sequence alignment of various tuf sequences. These multiple sequence alignments include the tuf sequences of four representative bacterial species selected from each target genus as well as tuf sequences from species of other closely related bacterial genera. A careful analysis of those alignments allowed the selection of oligonucleotide sequences which are conserved within the target genus but which discriminate sequences from other closely related genera, thereby permitting the genus-specific and ubiquitous detection and identification of the target bacterial genus.

For the selection of primers specific for *Enterococcus* spp. (Annex II), we have sequenced a portion of approximately 890 bp of the tuf genes for *Enterococcus avium, E. faecalis, E. faecium* and *E. gallinarum*. All other tuf sequences used in the alignment were either sequenced by us or selected from databases. The analysis of this sequence alignment led to the selection of a primer pair specific and ubiquitous for *Enterococcus* spp. (Table 7). All of the 11 enterococcal species tested were efficiently amplified and there was no amplification with genomic DNA from bacterial species of other genera.

For the selection of primers specific for *Staphylococcus* spp. (Annex III), we have also sequenced a portion of approximately 890 bp of the tuf genes for *Staphylococcus aureus, S. epidermidis, S. saprophyticus* and *S. simulans*. All other tuf sequences used in the alignment were either sequenced by us or selected from databases. The analysis of this sequence alignment led to the selection of two primer pairs specific and ubiquitous for *Staphylococcus* spp. (Table 7). Annex III shows the strategy used to select one of these two PCR primer pairs. The same strategy was used to select the other primer pair. Of the 14 staphylococcal species tested, one (*S. sciuri*) could not be amplified by the *Staphylococcus*-specific PCR assays using either one of these two primer pairs. For PCR assays using either one of these two primer pairs, there was no amplification with DNA from species of other bacterial genera.

Example 3

Selection from Tuf Sequences of PCR Primers Specific for *Candida albicans*

As shown in Annex IV, the comparison of tuf sequences from a variety of bacterial and eukaryotic species allowed the selection of PCR primers specific for *Candida albicans*. The strategy used to design the PCR primers was based on the analysis of a multiple sequence alignment of various tuf sequences. This multiple sequence alignment includes tuf sequences of five representative fungal species selected from the genus *Candida* which were determined by our group (i.e. *C. albicans, C. glabrata, C. krusei, C. parapsilosis* and *C. tropicalis*) as well as tuf sequences from other closely related fungal species. tuf sequences from various bacterial species were also included. A careful analysis of this sequence alignment allowed the selection of primers from the *C. albicans* tuf sequence; these primers discriminate sequences from other closely related *Candida* species and other fungal species, thereby permitting the species-specific and ubiquitous detection and identification of *C. albicans* (Table 7). All of 88 *Candida albicans* strains tested were efficiently amplified and there was no amplification with genomic DNA from other fungal or bacterial species.

Example 4

Selection of PCR Primers Specific for *Streptococcus* from recA

As shown in Annex V, the comparison of the various bacterial recA gene sequences available from databases (GenBank and EMBL) was used as a basis for the selection of PCR primers which are specific and ubiquitous for the bacterial genus *Streptococcus*. Since sequences of the recA gene are available for many bacterial species including five species of streptococci, it was possible to choose sequences well conserved within the genus *Streptococcus* but distinct from the recA sequences for other bacterial genera. When there were mismatches between the recA gene sequences from the five *Streptococcus* species, an inosine residue was incorporated into the primer (Annex V). The selected primers, each containing one inosine and no degenerescence, were specific and ubiquitous for *Streptococcus* species (Table 7). This PCR assay amplified all of the 22 *streptococcal* species tested. However, the *Streptococcus*-specific assay did not amplify DNA from 3 out of 9 strains of *S. mutans* and 1 out of 3 strains of *S. salivarius*. There was no amplification with genomic DNA from other bacterial genera (Table 7).

Example 5

Nucleotide Sequencing of DNA Fragments

The nucleotide sequence of a portion of the tuf genes from a variety of bacterial or fungal species was determined by using the dideoxynucleotide chain termination sequencing method (Sanger et al., 1977, Proc. Natl. Acad. Sci. USA. 74:5463-5467). The sequencing was performed by using an Applied Biosystems automated DNA sequencer (model 373A) with their PRISM™ Sequenase® Terminator Double-stranded DNA Sequencing Kit (Perkin-Elmer Corp., Applied Biosystems Division, Foster City, Calif.). The sequencing strategy does not discriminate tufA and tufB genes because the sequencing primers hybridize efficiently to both bacterial tuf genes. These DNA sequences are shown in the sequence listing (SEQ ID Nos: 118 to 146). The presence of several degenerated nucleotides in the various tuf sequences determined by our group (Table 13) corresponds to sequence variations between tufA and tufB.

Oligonucleotide Primers and Probes Selection.

Oligonucleotide probes and amplification primers were selected from the given proprietary DNA fragments or database sequences using the Oligo™ program and were synthesized with an automated ABI DNA synthesizer (Model 391, Perkin-Elmer Corp., Applied Biosystems Division) using phosphoramidite chemistry.

Example 6

Labeling of Oligonucleotides for Hybridization Assays

Each oligonucleotide was 5' end-labeled with γ-32P (dATP) by the T4 polynucleotide kinase (Pharmacia) as described earlier. The label could also be non-radioactive.

Specificity Test for Oligonucleotide Probes.

All labeled oligonucleotide probes were tested for their specificity by hybridization to DNAs from a variety of bacterial and fungal species selected from Tables 4, 5 and 6 as described earlier. Species-specific or genus-specific probes were those hybridizing only to DNA from the microbial species or genus from which it was isolated. Oligonucleotide probes found to be specific were submitted to ubiquity tests as follows.

Ubiquity Test for Oligonucleotide Probes.

Specific oligonucleotide probes were then used in ubiquity tests with strains of the target species or genus including reference strains and other strains obtained from various countries and which are representative of the diversity within each target species or genus. Chromosomal DNAs from the isolates were transferred onto nylon membranes and hybridized with labeled oligonucleotide probes as described for specificity tests. The batteries of isolates constructed for each target species or genus contain reference ATCC strains as well as a variety of clinical isolates obtained from various sources. Ubiquitous probes were those hybridizing to at least 80% of DNAs from the battery of clinical isolates of the target species or genus.

Example 7

Same as example 6 except that a pool of specific oligonucleotide probes is used for microbial identification (i) to increase sensitivity and assure 100% ubiquity or (ii) to identify simultaneously more than one microbial species and/or genus. Microbial identification could be performed from microbial cultures or directly from any clinical specimen.

Example 8

Same as example 6 except that bacteria or fungi were detected directly from clinical samples. Any biological sample was loaded directly onto a dot blot apparatus and cells were lysed in situ for bacterial or fungal detection and identification. Blood samples should be heparizined in order to avoid coagulation interfering with their convenient loading on a dot blot apparatus.

Example 9

PCR Amplification

The technique of PCR was used to increase the sensitivity and the rapidity of the assays. The sets of primers were tested in PCR assays performed directly from bacterial colonies or from a standardized bacterial suspension (see Example 10) to determine their specificity and ubiquity (Table 7). Examples of specific and ubiquitous PCR primer pairs are listed in Annex VI.

Specificity and Ubiquity Tests for Amplification Primers.

The specificity of all selected PCR primer pairs was tested against DNAs from a variety of bacterial and fungal species selected from Tables 4, 5 and 6 as described earlier. Primer pairs found specific for each species or genus were then tested for their ubiquity to ensure that each set of primers could amplify at least 90% of DNAs from a battery of isolates of the target species or genus. The batteries of isolates constructed for each species contain reference ATCC strains and various clinical isolates from around the world which are representative of the diversity within each species or genus.

Standard precautions to avoid false positive PCR results should be taken (Kwok and Higuchi, 1989, Nature, 239:237-238). Methods to inactivate PCR amplification products such as the inactivation by uracil-N-glycosylase may be used to control PCR carryover.

Example 10

Amplification Directly from Bacterial or Yeast Cultures

PCR assays were performed either directly from a bacterial colony or from a bacterial suspension, the latter being adjusted to a standard McFarland 0.5 (corresponds to approximately $1.5\times10^8$ bacteria/mL). In the case of direct amplification from a colony, a portion of a colony was transferred using a plastic rod directly into a 20 μL PCR reaction mixture containing 50 mM KCl, 10 mM Tris-HCl (pH 9.0), 0.1% Triton X-100, 2.5 mM $MgCl_2$, 0.4 μM of each primer, 200 μM of each of the four dNTPs and 0.5 unit of Taq DNA polymerase (Promega) combined with the TaqStart™ antibody (Clontech Laboratories Inc.). For the bacterial suspension, 1 μL of the cell suspension was added to 19 μL of the same PCR reaction mixture. For the identification from yeast cultures, 1 μL of a standard McFarland 1.0 (corresponds to approximately $3.0\times10^8$ bacteria/mL) concentrated 100 times by centrifugation was added directly to the PCR reaction. This concentration step for yeast cells was performed because a McFarland 0.5 for yeast cells has approximately 200 times fewer cells than a McFarland 0.5 for bacterial cells.

PCR reactions were then subjected to thermal cycling (3 min at 95° C. followed by 30 cycles of 1 second at 95° C. for the denaturation step and 30 seconds at 55° C. for the annealing-extension step) using a PTC-200 thermal cycler. PCR amplification products were then analyzed by standard agarose gel (2%) electrophoresis. Amplification products were visualized in agarose gels containing 0.25 μg/mL of ethidium bromide under UV at 254 nm. The entire PCR assay can be completed in approximately one hour.

Primer sequences derived from highly conserved regions of the bacterial 16S ribosomal RNA gene were used to provide an internal control for all PCR reactions. Alternatively, the internal control was derived from sequences not found in microorganisms or in the human genome. The internal control was integrated into all amplification reactions to verify the efficiency of the PCR assays and to ensure that significant PCR inhibition was absent. The internal control derived from rRNA was also useful to monitor the efficiency of the bacterial lysis protocols. The internal control and the species-specific or genus-specific amplifications were performed simultaneously in multiplex PCR assays.

Example 11

Amplification Directly from Urine Specimens

For PCR amplification performed directly from urine specimens, 1 μL of urine was mixed with 4 μL of a lysis solution containing 500 mM KCl, 100 mM tris-HCl (pH 9.0), 1% triton X-100. After incubation for at least 15 minutes at room temperature, 1 μL of the treated urine specimen was added directly to 19 μL of the PCR reaction mixture. The final concentration of the PCR reagents was 50 mM KCl, 10 mM Tris (pH 9.0), 0.1% Triton X-100, 2.5 mM $MgCl_2$, 0.4 μM of each primer, 200 μM of each of the four dNTPs. In addition, each 20 μL reaction contained 0.5 unit of Taq DNA polymerase (Promega) combined with the TaqStart™ antibody (Clontech Laboratories Inc.).

Strategies for the internal control, PCR amplification and agarose gel detection of the amplicons are as previously described in example 10.

Example 12

Detection of Antibiotic Resistance Genes

The presence of specific antibiotic resistance genes which are frequently encountered and clinically relevant is identified using the PCR amplification or hybridization protocols described previously. Specific oligonucleotides used as a basis for the DNA-based tests are selected from the antibiotic resistance gene sequences. These tests, which allow the rapid evaluation of bacterial resistance to antimicrobial agents, can be performed either directly from clinical specimens, from a standardized bacterial suspension or from a bacterial colony and should complement diagnostic tests for the universal detection of bacteria as well as for the species-specific and genus-specific microbial detection and identification.

Example 13

Same as examples 10 and 11 except that assays were performed by multiplex PCR (i.e. using several pairs of primers in a single PCR reaction) to reach an ubiquity of 100% for the specific targeted pathogen(s). For more heterogeneous microbial species or genus, a combination of PCR primer pairs may be required to detect and identify all representatives of the target species or genus.

Multiplex PCR assays could also be used to (i) detect simultaneously several microbial species and/or genera or, alternatively, (ii) to simultaneously detect and identify bacterial and/or fungal pathogens and detect specific antibiotic resistance genes either directly from a clinical specimen or from bacterial cultures.

For these applications, amplicon detection methods should be adapted to differentiate the various amplicons produced. Standard agarose gel electrophoresis could be used because it discriminates the amplicons based on their sizes. Another useful strategy for this purpose would be detection using a variety of fluorescent dyes emitting at different wavelengths. The fluorescent dyes can be each coupled with a specific oligonucleotide linked to a fluorescence quencher which is degraded during amplification to release the fluorescent dyes (e.g. TaqMan™, Perkin Elmer).

Example 14

Detection of Amplification Products

The person skilled in the art will appreciate that alternatives other than standard agarose gel electrophoresis (Example 10) may be used for the revelation of amplification products. Such methods may be based on fluorescence polarization or on the detection of fluorescence after amplification (e.g. Amplisensor™, Biotronics; TaqMan™, Perkin-Elmer Corp.) or other labels such as biotin (SHARP Signal™ system, Digene Diagnostics). These methods are quantitative and may be automated. One of the amplification primers or an internal oligonucleotide probe specific to the amplicon(s) derived from the species-specific, genus-specific or universal DNA fragments is coupled with the fluorescent dyes or with any other label. Methods based on the detection of fluorescence are particularly suitable for diagnostic tests since they are rapid and flexible as fluorescent dyes emitting at different wavelengths are available.

Example 15

Species-specific, genus-specific, universal and antibiotic resistance gene amplification primers can be used in other rapid amplification procedures such as the ligase chain reaction (LCR), transcription-mediated amplification (TMA), self-sustained sequence replication (3SR), nucleic acid sequence-based amplification (NASBA), strand displacement amplification (SDA), cycling probe technology (CPT) and branched DNA (bDNA) or any other methods to increase the sensitivity of the test. Amplifications can be performed from isolated bacterial cultures or directly from any clinical specimen. The scope of this invention is therefore not limited to the use of the DNA sequences from the enclosed Sequence Listing for PCR only but rather includes the use of any procedures to specifically detect bacterial DNA and which may be used to increase rapidity and sensitivity of the tests.

Example 16

A test kit would contain sets of probes specific for each microbial species or genus as well as a set of universal probes. The kit is provided in the form of test components, consisting of the set of universal probes labeled with non-radioactive labels as well as labeled species- or genus-specific probes for the detection of each pathogen of interest in specific types of clinical samples. The kit will also include test reagents necessary to perform the pre-hybridization, hybridization, washing steps and hybrid detection. Finally, test components for the detection of known antibiotic resistance genes (or derivatives therefrom) will be included. Of course, the kit will include standard samples to be used as negative and positive controls for each hybridization test.

Components to be included in the kits will be adapted to each specimen type and to detect pathogens commonly encountered in that type of specimen. Reagents for the universal detection of bacteria will also be included. Based on the sites of infection, the following kits for the specific detection of pathogens may be developed:

- A kit for the universal detection of bacterial or fungal pathogens from all clinical specimens which contains sets of probes specific for highly conserved regions of the microbial genomes.
- A kit for the detection of microbial pathogens retrieved from urine samples, which contains 5 specific test components (sets of probes for the detection of *Enterococcus faecium, Enteroccus* species, *Staphylococcus saprophyticus, Staphylococcus* species and *Candida albicans*).
- A kit for the detection of respiratory pathogens which contains 3 specific test components (sets of probes for the detection of *Staphylococcus* species, *Enterococcus* species and *Candida albicans*).
- A kit for the detection of pathogens retrieved from blood samples, which contains 10 specific test components (sets of probes for the detection of *Streptococcus* species, *Streptococcus agalactiae, Staphylococcus* species, *Staphylococcus saprophylicus, Enterococcus* species, *Enterococcus faecium, Neisseria* species, *Neisseria meningitidis, Listeria monocytogenes* and *Candida albicans*). This kit can also be applied for direct detection and identification from blood cultures.
- A kit for the detection of pathogens causing meningitis, which contains 5 specific test components (sets of probes for the detection of *Streptococcus* species, *Listeria monocytogenes, Neisseria meningitidis, Neisseria* species and *Staphylococcus* species).
- A kit for the detection of clinically important antibiotic resistance genes which contains sets of probes for the specific detection of at least one of the 26 following genes associated with antibiotic resistance: $bla_{tem}$, $bla_{rob}$, $bla_{shv}$, $bla_{oxa}$, blaZ, aadB, aacC1, aacC2, aacC3, aacA4, aac6'-IIa, ermA, ermB, ermC, mecA, vanA, vanB, vanC, satA, aac(6')-aph(2'), aad(6'), vat, vga, msrA, sul and int.
- Other kits adapted for the detection of pathogens from skin, abdominal wound or any other clinically relevant infections may also be developed.

Example 17

Same as example 16 except that the test kits contain all reagents and controls to perform DNA amplification assays. Diagnostic kits will be adapted for amplification by PCR (or other amplification methods) performed directly either from clinical specimens or from microbial cultures. Components required for (i) universal bacterial detection, (ii) species-specific and genus-specific bacterial and/or fungal detection and identification and (iii) detection of antibiotic resistance genes will be included.

Amplification assays could be performed either in tubes or in microtitration plates having multiple wells. For assays in plates, the wells will contain the specific amplification primers and control DNAs and the detection of amplification products will be automated. Reagents and amplification primers for universal bacterial detection will be included in kits for tests performed directly from clinical specimens. Components required for species-specific and genus-specific bacterial and/or fungal detection and identification as well as for the simultaneous antibiotic resistance genes detection will be included in kits for testing directly from bacterial or fungal cultures as well as in kits for testing directly from any type of clinical specimen.

The kits will be adapted for use with each type of specimen as described in example 16 for hybridization-based diagnostic kits.

Example 18

It is understood that the use of the probes and amplification primers described in this invention for bacterial and/or fungal detection and identification is not limited to clinical microbiology applications. In fact, we feel that other sectors could also benefit from these new technologies. For example, these tests could be used by industries for quality control of food, water, air, pharmaceutical products or other products requiring microbiological control. These tests could also be applied to detect and identify bacteria or fungi in biological samples from organisms other than humans (e.g. other primates, birds, plants, mammals, farm animals, livestock and others). These diagnostic tools could also be very useful for research purposes including clinical trials and epidemiological studies.

This invention has been described herein above, and it is readily apparent that modifications can be made thereto without departing from the spirit of this invention. These modifications are under the scope of this invention, as defined in the appended claims.

TABLE 1

Distribution (%) of nosocomial pathogens for various human infections in USA (1990-1992)[1].

| Pathogen | UTI[2] | SSI[3] | BSI[4] | Pneumonia | CSF[5] |
|---|---|---|---|---|---|
| *Escherichia coli* | 27 | 9 | 5 | 4 | 2 |
| *Staphylococcus aureus* | 2 | 21 | 17 | 21 | 2 |
| *Staphylococcus epidermidis* | 2 | 6 | 20 | 0 | 1 |
| *Enterococcus faecalis* | 16 | 12 | 9 | 2 | 0 |
| *Enterococcus faecium* | 1 | 1 | 0 | 0 | 0 |

TABLE 1-continued

Distribution (%) of nosocomial pathogens for various human infections in USA (1990-1992)[1].

| Pathogen | UTI[2] | SSI[3] | BSI[4] | Pneumonia | CSF[5] |
|---|---|---|---|---|---|
| *Pseudomonas aeruginosa* | 12 | 9 | 3 | 18 | 0 |
| *Klebsiella pneumoniae* | 7 | 3 | 4 | 9 | 0 |
| *Proteus mirabilis* | 5 | 3 | 1 | 2 | 0 |
| *Streptococcus pneumoniae* | 0 | 0 | 3 | 1 | 18 |
| Group B *Streptococci* | 1 | 1 | 2 | 1 | 6 |
| Other *Streptococci* | 3 | 5 | 2 | 1 | 3 |
| *Haemophilus influenzae* | 0 | 0 | 0 | 6 | 45 |
| *Neisseria meningitidis* | 0 | 0 | 0 | 0 | 14 |
| *Listeria monocytogenes* | 0 | 0 | 0 | 0 | 3 |
| Other *Enterococci* | 1 | 1 | 0 | 0 | 0 |
| Other *Staphylococci* | 2 | | 8 | 13 | 20 |
| *Candida albicans* | 9 | 3 | 5 | 5 | 0 |
| Other *Candida* | 2 | | 1 | 3 | 10 |
| *Enterobacter* spp. | 5 | 7 | 4 | 12 | 2 |
| *Acinetobacter* spp. | 1 | 1 | 2 | 4 | 2 |
| *Citrobacter* spp. | 2 | 1 | 1 | 1 | 0 |
| *Serratia marcescens* | 1 | 1 | 1 | 3 | 1 |
| Other *Klebsiella* | 1 | 1 | 1 | 2 | 1 |
| Others | 0 | 6 | 4 | 5 | 0 |

[1]Data recorded by the National Nosocomial Infections Surveillance (NNIS) from 80 hospitals (Emori and Gaynes, 1993, Clin. Microbiol. Rev., 6: 428-442).
[2]Urinary tract infection.
[3]Surgical site infection.
[4]Bloodstream infection.
[5]Cerebrospinal fluid.

TABLE 2

Distribution (%) of bloodstream infection pathogens in Quebec (1995), Canada (1992), UK (1969-1988) and USA (1990-1992).

| | | | UK[3] | | USA[4] |
|---|---|---|---|---|---|
| Organism | Quebec[1] | Canada[2] | Community-acquired | Hospital-acquired | Hospital-acquired |
| *E. coli* | 15.6 | 53.8 | 24.8 | 20.3 | 5.0 |
| *S. epidermidis* and other CoNS[5] | 25.8 | NI[6] | 0.5 | 7.2 | 31.0 |
| *S. aureus* | 9.6 | NI | 9.7 | 19.4 | 16.0 |
| *S. pneumoniae* | 6.3 | NI | 22.5 | 2.2 | NR[7] |
| *E. faecalis* | 3.0 | NI | 1.0 | 4.2 | NR |
| *E. faecium* | 2.6 | NI | 0.2 | 0.5 | NR |
| *Enterococcus* spp. | NR | NI | NR | NR | 9.0 |
| *H. influenzae* | 1.5 | NR | 3.4 | 0.4 | NR |
| *P. aeruginosa* | 1.5 | 8.2 | 1.0 | 8.2 | 3.0 |
| *K. pneumoniae* | 3.0 | 11.2 | 3.0 | 9.2 | 4.0 |
| *P. mirabilis* | NR | 3.9 | 2.8 | 5.3 | 1.0 |
| *S. pyogenes* | NR | NI | 1.9 | 0.9 | NR |
| *Enterobacter* spp. | 4.1 | 5.5 | 0.5 | 2.3 | 4.0 |
| *Candida* spp. | 8.5 | NI | NR | 1.0 | 8.0 |
| Others | 18.5 | 17.4[8] | 28.7 | 18.9 | 19.0 |

[1]Data obtained for 270 isolates collected at the Centre Hospitalier de l'Université Laval (CHUL) during a 5 month period (May to October 1995).
[2]Data from 10 hospitals throughout Canada representing 941 gram-negative bacterial isolates. (Chamberland et al., 1992, Clin. Infect. Dis., 15: 615-628).
[3]Data from a 20-year study (1969-1988) for nearly 4000 isolates (Eykyn et al., 1990, J. Antimicrob. Chemother., Suppl. C, 25: 41-58).
[4]Data recorded by the National Nosocomial Infections Surveillance (NNIS) from 80 hospitals (Emori and Gaynes, 1993, Clin. Microbiol. Rev., 6: 428-442).
[5]Coagulase-negative *staphylococci*.
[6]NI, not included. This survey included only gram-negative species.
[7]NR, incidence not reported for these species or genera.
[8]In this case, 17.4 stands for other gram-negative bacterial species.

TABLE 3

Distribution of positive and negative clinical specimens tested at the microbiology laboratory of the CHUL (February 1994-January 1995).

| Clinical specimens and/or sites | No. of samples tested (%) | % of positive specimens | % of negative specimens |
|---|---|---|---|
| Urine | 17,981 (54.5) | 19.4 | 80.6 |
| Blood culture/marrow | 10,010 (30.4) | 6.9 | 93.1 |
| Sputum | 1,266 (3.8) | 68.4 | 31.6 |
| Superficial pus | 1,136 (3.5) | 72.3 | 27.7 |
| Cerebrospinal fluid | 553 (1.7) | 1.0 | 99.0 |
| Synovial fluid | 523 (1.6) | 2.7 | 97.3 |
| Respiratory tract | 502 (1.5) | 56.6 | 43.4 |
| Deep pus | 473 (1.4) | 56.8 | 43.2 |
| Ears | 289 (0.9) | 47.1 | 52.9 |
| Pleural and pericardial fluid | 132 (0.4) | 1.0 | 99.0 |
| Peritoneal fluid | 101 (0.3) | 28.6 | 71.4 |
| Total: | 32,966 (100.0) | 20.0 | 80.0 |

TABLE 4

Gram-negative bacterial species (90) used to test the specificity of PCR primers and DNA probes (continues on next page).

| Bacterial species | Number of reference strains tested[a] |
|---|---|
| *Acinetobacter baumannii* | 1 |
| *Acinetobacter lwoffii* | 3 |
| *Actinobacillus lignieresii* | 1 |
| *Alcaligenes faecalis* | 1 |
| *Alcaligenes odorans* | 1 |
| *Alcaligenes xylosoxydans* subsp. *denitrificans* | 1 |
| *Bacteroides distasonis* | 1 |
| *Bacteroides fragilis* | 1 |
| *Bacteroides ovatus* | 1 |
| *Bacteroides thetaiotaomicron* | 1 |
| *Bacteroides vulgatus* | 1 |
| *Bordetella bronchiseptica* | 1 |
| *Bordetella parapertussis* | 1 |
| *Bordetella pertussis* | 2 |
| *Burkholderia cepacia* | 1 |
| *Citrobacter amalonaticus* | 1 |
| *Citrobacter diversus* subsp. *koseri* | 2 |
| *Citrobacter freundii* | 1 |
| *Comamonas acidovorans* | 1 |
| *Enterobacter aerogenes* | 1 |
| *Enterobacter agglomerans* | 1 |
| *Enterobacter cloacae* | 1 |
| *Escherichia coli* | 9 |
| *Escherichia fergusonii* | 1 |
| *Escherichia hermannii* | 1 |
| *Escherichia vulneris* | 1 |
| *Flavobacterium meningosepticum* | 1 |
| *Flavobacterium indologenes* | 1 |
| *Flavobacterium odoratum* | 1 |
| *Fusobacterium necrophorum* | 2 |
| *Gardnerella vaginalis* | 1 |
| *Haemophilus haemolyticus* | 1 |
| *Haemophilus influenzae* | 12 |
| *Haemophilus parahaemolyticus* | 1 |
| *Haemophilus parainfluenzae* | 2 |
| *Hafnia alvei* | 1 |
| *Kingella indologenes subsp. suttonella* | 1 |

TABLE 4-continued

Gram-negative bacterial species (90) used to test the specificity of PCR primers and DNA probes (continues on next page).

| Bacterial species | Number of reference strains tested[a] |
|---|---|
| *Kingella kingae* | 1 |
| *Klebsiella ornithinolytica* | 1 |
| *Klebsiella oxytoca* | 1 |
| *Klebsiella pneumoniae* | 8 |
| *Moraxella atlantae* | 1 |
| *Moraxella catarrhalis* | 5 |
| *Moraxella lacunata* | 1 |
| *Moraxella osloensis* | 1 |
| *Moraxella phenylpyruvica* | 1 |
| *Morganella morganii* | 1 |
| *Neisseria animalis* | 1 |
| *Neisseria canis* | 1 |
| *Neisseria caviae* | 1 |
| *Neisseria cinerea* | 1 |
| *Neisseria cuniculi* | 1 |
| *Neisseria elongata* subsp. *elongata* | 1 |
| *Neisseria elongata* subsp. *glycoytica* | 1 |
| *Neisseria flavescens* | 1 |
| *Neisseria flavescens Branham* | 1 |
| *Neisseria gonorrhoeae* | 18 |
| *Neisseria lactamica* | 1 |
| *Neisseria meningitidis* | 4 |
| *Neisseria mucosa* | 2 |
| *Neisseria polysaccharea* | 1 |
| *Neisseria sicca* | 3 |
| *Neisseria subflava* | 3 |
| *Neisseria weaveri* | 1 |
| *Ochrobactrum antropi* | 1 |
| *Pasteurella aerogenes* | 1 |
| *Pasteurella multocida* | 1 |
| *Prevotella melaninogenica* | 1 |
| *Proteus mirabilis* | 3 |
| *Proteus vulgaris* | 1 |
| *Providencia alcalifaciens* | 1 |
| *Providencia rettgeri* | 1 |
| *Providencia rustigianii* | 1 |
| *Providencia stuartii* | 1 |
| *Pseudomonas aeruginosa* | 14 |
| *Pseudomonas fluorescens* | 2 |
| *Pseudomonas stutzeri* | 1 |
| *Salmonella arizonae* | 1 |
| *Salmonella choleraesuis* | 1 |
| *Salmonella gallinarum* | 1 |
| *Salmonella typhimurium* | 3 |
| *Serratia liquefaciens* | 1 |
| *Serratia marcescens* | 1 |
| *Shewanella putida* | 1 |
| *Shigella boydii* | 1 |
| *Shigella dysenteriae* | 1 |
| *Shigella flexneri* | 1 |
| *Shigella sonnei* | 1 |
| *Stenotrophomonas maltophilia* | 1 |
| *Yersinia enterocolitica* | 1 |

[a]Most reference strains were obtained from the American Type Culture Collection (ATCC). The other reference strains were obtained from (i) the Laboratoire de Santé Publique du Québec (LSPQ), (ii) the Center for Disease Control and Prevention (CDC) and (iii) the National Culture Type Collection (NCTC).

TABLE 5

Gram-positive bacterial species (97) used to test the specificity of PCR primers and DNA probes (continues on next page).

| Bacterial species | Number of reference strains tested[a] |
|---|---|
| *Abiotrophia adiacens* | 1 |
| *Abiotrophia defectiva* | 1 |
| *Actinomyces israelii* | 1 |
| *Clostridium perfringens* | 1 |
| *Corynebacterium accolens* | 1 |
| *Corynebacterium aquaticum* | 1 |
| *Corynebacterium bovis* | 1 |
| *Corynebacterium cervicis* | 1 |
| *Corynebacterium diphteriae* | 6 |
| *Corynebacterium flavescens* | 1 |
| *Corynebacterium genitalium* | 6 |
| *Corynebacterium jeikeium* | 1 |
| *Corynebacterium kutcheri* | 1 |
| *Corynebacterium matruchotii* | 1 |
| *Corynebacterium minutissimum* | 1 |
| *Corynebacterium mycetoides* | 1 |
| *Corynebacterium pseudodiphtheriticum* | 1 |
| *Corynebacterium pseudogenitalium* | 6 |
| *Corynebacterium renale* | 1 |
| *Corynebacterium striatum* | 1 |
| *Corynebacterium ulcerans* | 1 |
| *Corynebacterium urealyticum* | 1 |
| *Corynebacterium xerosis* | 1 |
| *Enterococcus avium* | 1 |
| *Enterococcus casseliflavus* | 1 |
| *Enterococcus cecorum* | 1 |
| *Enterococcus dispar* | 1 |
| *Enterococcus durans* | 1 |
| *Enterococcus faecalis* | 6 |
| *Enterococcus faecium* | 3 |
| *Enterococcus flavescens* | 1 |
| *Enterococcus gallinarum* | 3 |
| *Enterococcus hirae* | 1 |
| *Enterococcus mundtii* | 1 |
| *Enterococcus pseudoavium* | 1 |
| *Enterococcus raffinosus* | 1 |
| *Enterococcus saccharolyticus* | 1 |
| *Enterococcus solitarius* | 1 |
| *Eubacterium lentum* | 1 |
| *Gemella haemolysans* | 1 |
| *Gemella morbillorum* | 1 |
| *Lacto bacillus acidophilus* | 1 |
| *Listeria innocua* | 1 |
| *Listeria ivanovii* | 1 |
| *Listeria grayi* | 1 |
| *Listeria monocyto genes* | 3 |
| *Listeria murrayi* | 1 |
| *Listeria seeligeri* | 1 |
| *Listeria weishimeri* | 1 |
| *Micrococcus kristinae* | 1 |
| *Micrococcus luteus* | 1 |
| *Micrococcus lylae* | 1 |
| *Micrococcus roseus* | 1 |
| *Micrococcus varians* | 1 |
| *Peptococcus niger* | 1 |
| *Peptostreptococcus anaerobius* | 1 |
| *Peptostreptococcus asaccharolyticus* | 1 |
| *Staphylococcus aureus* | 10 |
| *Staphylococcus auricularis* | 1 |
| *Staphylococcus capitis* subsp. *urealyticus* | 1 |
| *Staphylococcus cohnii* | 1 |

TABLE 5-continued

Gram-positive bacterial species (97) used to test the specificity of PCR primers and DNA probes (continues on next page).

| Bacterial species | Number of reference strains tested[a] |
|---|---|
| *Staphylococcus epidermidis* | 2 |
| *Staphylococcus haemolyticus* | 2 |
| *Staphylococcus hominis* | 2 |
| *Staphylococcus lugdunensis* | 1 |
| *Staphylococcus saprophyticus* | 3 |
| *Staphylococcus schleiferi* | 1 |
| *Staphylococcus sciuri* | 1 |
| *Staphylococcus simulans* | 1 |
| *Staphylococcus warneri* | 1 |
| *Staphylococcus xylosus* | 1 |
| *Streptococcus agalactiae* | 6 |
| *Streptococcus anginosus* | 2 |
| *Streptococcus bovis* | 2 |
| *Streptococcus constellatus* | 1 |
| *Streptococcus crista* | 1 |
| *Streptococcus dysgalactiae* | 1 |
| *Streptococcus equi* | 1 |
| *Streptococcus gordonii* | 1 |
| Group C *Streptococci* | 1 |
| Group D *Streptococci* | 1 |
| Group E *Streptococci* | 1 |
| Group F *Streptococci* | 1 |
| Group G *Streptococci* | 1 |
| *Streptococcus intermedius* | 1 |
| *Streptococcus mitis* | 2 |
| *Streptococcus mutans* | 1 |
| *Streptococcus oralis* | 1 |
| *Streptococcus parasanguis* | 1 |
| *Streptococcus pneumoniae* | 6 |
| *Streptococcus pyogenes* | 3 |
| *Streptococcus salivarius* | 2 |
| *Streptococcus sanguis* | 2 |
| *Streptococcus sobrinus* | 1 |
| *Streptococcus suis* | 1 |
| *Streptococcus uberis* | 1 |
| *Streptococcus vestibularis* | 1 |

[a]Most reference strains were obtained from the American Type Culture Collection (ATCC). The other reference strains were obtained from (i) the Laboratoire de Santé Publique du Qu ébec (LSPQ), (ii) the Center for Disease Control and Prevention (CDC) and (iii) the National Culture Type Collection (NCTC).

TABLE 6

Fungal species (12) used to test the specificity of PCR primers and DNA probes.

| Fungal species | Number of reference strains tested[a] |
|---|---|
| *Candida albicans* | 12 |
| *Candida glabrata* | 1 |
| *Candida guilliermondii* | 1 |
| *Candida kefyr* | 3 |
| *Candida krusei* | 2 |
| *Candida lusitaniae* | 1 |
| *Candida parapsilosis* | 2 |
| *Candida tropicalis* | 3 |
| *Rhodotorula glutinis* | 1 |
| *Rhodotorula minuta* | 1 |
| *Rhodotorula rubra* | 1 |
| *Saccharomyces cerevisiae* | 1 |

[a]Most reference strains were obtained from (i) the American Type Culture Collection (ATCC) and (ii) the Laboratoire de Santé Publique du Québec (LSPQ).

TABLE 7

PCR assays developed for several clinically important bacterial and fungal pathogens (continues on next page).

| Organism | Primer Pair[a] SEQ ID NO | Amplicon size (bp) | Ubiquity[b] | DNA amplification from culture[c] | DNA amplification from specimens[d] |
|---|---|---|---|---|---|
| *Enterococcus faecium* | 1-2 | 216 | 79/80 | + | + |
| *Listeria monocytogenes* | 3-4 | 130 | 164/168[e] | + | + |
| *Neisseria meningitidis* | 5-6 | 177 | 258/258 | + | + |
| *Staphylococcus saprophyticus* | 7-8 | 149 | 245/260 | + | NT |
| *Streptococcus agalactiae* | 9-10 | 154 | 29/29 | + | + |
| *Candida albicans* | 11-12 | 149 | 88/88 | + | NT |
| *Enterococcus* spp. (11 species)[f] | 13-14 | 112 | 87/87 | + | NT |
| *Neisseria* spp. (12 species)[f] | 15-16 | 103 | 321/321 | + | + |
| *Staphylococcus* spp. | 17-18 | 192 | 13/14 | + | NT |
| (14 species) | 19-20 | 221 | 13/14 | + | NT |
| *Streptococcus* spp. (22 species)[f] | 21-22 | 153 | 210/214[g] | + | + |
| Universal detection[h] (95 species)[i] | 23-24 | 309 | 104/116[i] | + | + |

[a]All primer pairs are specific in PCR assays since no amplification was observed with DNA from the bacterial and fungal species other than the species of interest listed in Tables 4, 5 and 6.
[b]Ubiquity was tested by using reference strains as well as strains from throughout the world, which are representatite of the diversity within each target species or genus.
[c]For all primer pairs, PCR amplifications performed directly from a standardized microbial suspension (MacFarland) or from a colony were all specific and ubiquitous.
[d]PCR assays performed directly from blood cultures, urine specimens or cerebrospinal fluid. NT, not tested.
[e]The four *L. monocytogenes* strains undetected are not clinical isolates. These strains were isolated from food and are not associated with a human infection.
[f]The bacterial species tested include all those clinically relevant for each genus (Tables 4 and 5). All of these species were efficiently amplified by their respective genus-specific PCR assay, except for the *Staphylococcus*-specific assay, which does not amplify *S. sciuri*.
[g] The *Streptococcus*-specific PCR assay did not amplify 3 out of 9 strains of *S. mutans* and 1 out of 3 strains of *S. salivarius*.
[h] The primers selected for universal bacterial detection do not amplify DNA of non-bacterial origin, including human and other types of eukaryotic genomic DNA.
[i] For the universal amplification, the 95 bacterial species tested represent the most clinically important bacterial species listed in Tables 4 and 5. The 12 strains not amplified are representatives of genera *Corynebacterium* (11 species) and *Stenotrophomonas* (1 species).

TABLE 8

Target genes for the various genus-specific, species-specific and universal amplification assays.

| Microorganisms | Gene | Protein encoded |
|---|---|---|
| *Candida albicans* | tuf | translation elongation factor EF-Tu |
| *Enterococcus faecium* | ddl | D-alanine: D-alanine ligase |
| *Listeria monocytogenes* | actA | actin-assembly inducing protein |
| *Neisseria meningitidis* | omp | outer membrane protein |
| *Streptococcus agalactiae* | cAMP | cAMP factor |
| *Staphylococcus saprophyticus* | unknown | unknown |
| *Enterococcus* spp. | tuf | translation elongation factor EF-Tu |
| *Neisseria* spp. | asd | ASA-dehydrogenase |
| *Staphylococcus* spp. | tuf | translation elongation factor EF-Tu |
| *Streptococcus* spp. | recA | RecA protein |
| Universal detection | tuf | translation elongation factor EF-Tu |

TABLE 9

Antibiotic resistance genes selected for diagnostic purposes.

| Genes | SEQ ID NOs selected primers | SEQ ID NOs originating fragment | Antibiotics | Bacteria[a] |
|---|---|---|---|---|
| $bla_{oxa}$ | 49-50 | 110 | β-lactams | *Enterobacteriaceae*, *Pseudomonadaceae* |
| blaZ | 51-52 | 111 | β-lactams | *Enterococcus* spp. |
| aac6'-IIa | 61-64 | 112 | Aminoglycosides | *Pseudomonadaceae* |
| ermA | 91-92 | 113 | Macrolides | *Staphylococcus* spp. |

TABLE 9-continued

Antibiotic resistance genes selected for diagnostic purposes.

| Genes | SEQ ID NOs selected primers | SEQ ID NOs originating fragment | Antibiotics | Bacteria[a] |
|---|---|---|---|---|
| ermB | 93-94 | 114 | Macrolides | *Staphylococcus* spp. |
| ermC | 95-96 | 115 | Macrolides | *Staphylococcus* spp. |
| vanB | 71-74 | 116 | Vancomycin | *Enterococcus* spp. |
| vanC | 75-76 | 117 | Vancomycin | *Enterococcus* spp. |
| aad(6') | 173-174 | — | Streptomycin | *Enterococcus* spp. |

[a]Bacteria having high incidence for the specified antibiotic resistance genes. The presence of these antibiotic resistance genes in other bacteria is not excluded.

TABLE 10

Antibiotic resistance genes from our co-pending US (N.S. 08/526840) and PCT (PCT/CA/95/00528) patent applications for which we have selected PCR primer pairs.

| Genes | SEQ ID NOs of selected primers | Antibiotics | Bacteria[a] |
|---|---|---|---|
| $bla_{tem}$ | 37-40 | β-lactams | *Enterobacteriaceae*, *Pseudomonadaceae*, *Haemophilus* spp., *Neisseria* spp. |
| $bla_{rob}$ | 45-48 | β-lactams | *Haemophilus* spp., *Pasteurella* spp. |
| $bla_{shv}$ | 41-44 | β-lactams | *Klebsiella* spp. and other *Enterobacteriaceae* |

TABLE 10-continued

Antibiotic resistance genes from our co-pending US (N.S. 08/526840) and PCT (PCT/CA/95/00528) patent applications for which we have selected PCR primer pairs.

| Genes | SEQ ID NOs of selected primers | Antibiotics | Bacteria[a] |
|---|---|---|---|
| aadB | 53-54 | Aminoglycosides | *Enterobacteriaceae*, |
| aacC1 | 55-56 | | *Pseudomonadaceae* |
| aacC2 | 57-58 | | |
| aacC3 | 59-60 | | |
| aacA4 | 65-66 | | |
| mecA | 97-98 | β-lactams | *Staphylococcus* spp. |
| vanA | 67-70 | Vancomycin | *Enterococcus* spp. |
| satA | 81-82 | Macrolides | *Enterococcus* spp. |
| aac(6')-aph(2") | 83-86 | Aminoglycosides | *Enterococcus* spp., *Staphylococcus* spp. |
| vat | 87-88 | Macrolides | *Staphylococcus* spp. |
| vga | 89-90 | Macrolides | *Staphylococcus* spp. |
| msrA | 77-80 | Erythromycin | *Staphylococcus* spp. |
| int | 99-102 | β-lactams, trimethoprim, | *Enterobacteriaceae*, |
| sul | 103-106 | aminoglycosides, antiseptic, chloramphenicol | *Pseudomonadaceae* |

[a]Bacteria having high incidence for the specified antibiotic resistance genes. The presence of these antibiotic resistance genes in other bacteria is not excluded.

TABLE 11

Correlation between disk diffusion and PCR amplification of antibiotic resistance genes in *Staphylococcus* species[a].

| | | | Disk diffusion (Kirby-Bauer)[b] | | |
|---|---|---|---|---|---|
| Antibiotic | Phenotype | PCR | Resistant | Inter-mediate | Sensitive |
| Penicillin | blaZ | + | 165 | 0 | 0 |
| | | − | 0 | 0 | 31 |
| Oxacillin | mecA | + | 51 | 11 | 4 |
| | | − | 2 | 0 | 128 |
| Gentamycin | aac(6')aph(2") | + | 24 | 18 | 6 |
| | | − | 0 | 0 | 148 |
| Erythromycin | ermA | + | 15 | 0 | 0 |
| | ermB | + | 0 | 0 | 0 |
| | ermC | + | 43 | 0 | 0 |
| | msrA | + | 4 | 0 | 0 |
| | | − | 0 | 1 | 136 |

[a]The Staphylococcus strains studied include *S. aureus* (82 strains), *S. epidermidis* (83 strains), *S. hominis* (2 strains), *S. capitis* (3 strains), *S. haemolyticus* (9 strains), *S. simulans* (12 strains) and *S. warneri* (5 strains), for a total of 196 strains.
[b]Susceptibility testing was performed by the method of Kirby-Bauer according to the protocol reccommended by the National Committee of Clinical Laboratory Standards (NCCLS).

TABLE 12

Correlation between disk diffusion profiles and PCR amplification of antibiotic resistance genes in *Enterococcus* species[a].

| | | | Disk diffusion (Kirby-Bauer)[b] | |
|---|---|---|---|---|
| Antibiotic | Phenotype | PCR | Resistant | Sensitive |
| Ampicillin | blaZ | + | 0 | 2 |
| | | − | 1 | 30 |
| Gentamycin | aac(6')aph(2") | + | 51 | 1 |
| | | − | 3 | 38 |
| Streptomycin | aad(6') | + | 26 | 15 |
| | | − | 6 | 27 |
| Vancomycin | vanA | + | 36 | 0 |
| | vanB | + | 26 | 0 |
| | | − | 0 | 40 |

[a]The Enterococcus strains studied include *E. faecalis* (33 strains) and *E. faecium* (69 strains), for a total of 102 strains.
[b]Susceptibility testing was performed by the method of Kirby-Bauer according to the protocol reccommended by the National Committee of Clinical Laboratory Standards (NCCLS).

TABLE 13

Origin of tuf sequences in the Sequence Listing (continues on next page).

| SEQ ID NO | *Bacterial or fungal species* | Source |
|---|---|---|
| 118 | *Abiotrophia adiacens* | This patent |
| 119 | *Abiotrophia defectiva* | This patent |
| 120 | *Candida albicans* | This patent |
| 121 | *Candida glabrata* | This patent |
| 122 | *Candida krusei* | This patent |
| 123 | *Candida parapsilosis* | This patent |
| 124 | *Candida tropicalis* | This patent |
| 125 | *Corynebacterium accolens* | This patent |
| 126 | *Corynebacterium diphteriae* | This patent |
| 127 | *Corynebacterium genitalium* | This patent |
| 128 | *Corynebacterium jeikeium* | This patent |
| 129 | *Corynebacterium pseudotuberculosis* | This patent |
| 130 | *Corynebacterium striatum* | This patent |
| 131 | *Enterococcus avium* | This patent |
| 132 | *Enterococcus faecalis* | This patent |
| 133 | *Enterococcus faecium* | This patent |
| 134 | *Enterococcus gallinarum* | This patent |
| 135 | *Gardnerella vaginalis* | This patent |
| 136 | *Listeria innocua* | This patent |
| 137 | *Listeria ivanovii* | This patent |
| 138 | *Listeria monocytogenes* | This patent |
| 139 | *Listeria seeligeri* | This patent |
| 140 | *Staphylococcus aureus* | This patent |
| 141 | *Staphylococcus epidermidis* | This patent |
| 142 | *Staphylococcus saprophyticus* | This patent |
| 143 | *Staphylococcus simulans* | This patent |
| 144 | *Streptococcus agalactiae* | This patent |
| 145 | *Streptococcus pneumoniae* | This patent |
| 146 | *Streptococcus salivarius* | This patent |
| 147 | *Agrobacterium tumefaciens* | Database |
| 148 | *Bacillus subtilis* | Database |
| 149 | *Bacteroides fragilis* | Database |
| 150 | *Borrelia burgdorferi* | Database |
| 151 | *Brevibacterium linens* | Database |
| 152 | *Burkholderia cepacia* | Database |
| 153 | *Chlamydia trachomatis* | Database |
| 154 | *Escherichia coli* | Database |
| 155 | *Fibrobacter succinogenes* | Database |
| 156 | *Flavobacterium ferrugineum* | Database |
| 157 | *Haemophilus influenzae* | Database |
| 158 | *Helicobacter pylori* | Database |
| 159 | *Micrococcus luteus* | Database |
| 160 | *Mycobacterium tuberculosis* | Database |
| 161 | *Mycoplasma genitalium* | Database |
| 162 | *Neisseria gonorrhoeae* | Database |
| 163 | *Rickettsia prowazekii* | Database |
| 164 | *Salmonella typhimurium* | Database |
| 165 | *Shewanella putida* | Database |
| 166 | *Stigmatella aurantiaca* | Database |
| 167 | *Streptococcus pyogenes* | Database |
| 168 | *Thiobacillus cuprinus* | Database |
| 169 | *Treponema pallidum* | Database |
| 170 | *Ureaplasma urealyticum* | Database |
| 171 | *Wolinella succinogenes* | Database |

ANNEX I
Strategy for the selection from tuf sequences of the universal amplification primers

| Organism | 491 517 | | 776 802 | SEQ ID NO: |
|---|---|---|---|---|
| *Abiotrophia adiacens* | CAACTGTAAC TGGTGTTGAA ATGTTCC | . . . | AAATGGT AATGCCTGGT GATAACGTAA | 118 |
| *Abiotrophia defective* | CTACCGTTAC CGGTGTTGAA ATGTTCC | . . . | AAATGGT TATGCCAGGC GACAACGTAC | 119 |
| *Agrobacterium tumefaciens* | CGACTGTTAC CGGCGTTGAA ATGTTCC | . . . | AAATGGT TATGCCTGGC GACAACGTCA | 175 |
| *Bacillus subtilis* | CAACTGTTAC AGGTGTTGAA ATGTTCC | . . . | AAATGGT TATGCCTGGA GATAACACTG | 176 |
| *Bacteroides fragiles* | CAGTTGTAAC AGGTGTTGAA ATGTTCC | . . . | AAATGGT AATGCCGGGT GATAACGTAA | 177 |
| *Borrelia burgdorferi* | CTACTGTTAC TGGTGTTGAA ATGTTCC | . . . | AAATGGT TATGCCTGGT GATAATGTTG | 178 |
| *Brevibacterium linens* | CGACTGTCAC CGCTATCGAG ATGTTCC | . . . | AGATGGT CATGCCCGGC GACACCACCG | 179 |
| *Burkholderia cepacia* | CGACCTGCAC GGGCGTTGAA ATGTTCC | . . . | AAATGGT CATGCCGGGC GACAACGTGT | 180 |
| *Chlamydia trachomatis* | CGATTGTTAC TGGGGTTGAA ATGTTCA | . . . | AGATGGT CATGCCTGGG GATAACGTTG | 181 |
| *Corynebacterium diphteriae* | CCACCGTTAC CGGTATCGAG ATGTTCC | . . . | AGATGGT CATGCCTGGC GACAACGTCG | 126 |
| *Corynebacterium genitalium* | CCACCGTTAC CTCCATCGAG ATGTTCA | . . . | AGATGGT TATGCCGGGC GACAACGTTG | 127 |
| *Corynebacterium jeikeium* | CCACCGTTAC CTCCATCGAG ATGTTCA | . . . | AGATGGT TATGCCGGGC GACAACGTTG | 128 |
| *Enterococcus faecalis* | CAACYGTTAC AGGTGTTGAA ATGTTCC | . . . | AAATGGT AATGCCTGGT GATAACGTTG | 132 |
| *Enterococcus faecium* | CAACAGTTAC TGGTGTTGAA ATGTTCC | . . . | AAATGGT CATGCCCGGT GACAACGT.. | 133 |
| *Escherichia coli* | CTACCTGTAC TGGCGTTGAA ATGTTCC | . . . | ATATGGT AATGCCGGGC GACAACATCA | 182 |
| *Fibrobacter succinogenes* | ACGTCATCAC CGGTGTTGAA ATGTTCC | . . . | AAATGGT TACTCCGGGT GACACGGTCA | 183 |
| *Flavobacterium ferrugineum* | CTACCGTTAC AGGTGTTGAG ATGTTCC | . . . | AAATGGT TATGCCTGGT GATAACACCA | 184 |
| *Gardnerella vaginalis* | CCACCGTCAC CTCTATCGAG ACCTTCC | . . . | AAATGGT TCAGCCAGGC GATCACGCAA | 135 |
| *Haemophilus influenzae* | CTACTGTAAC GGGTGTTGAA ATGTTCC | . . . | AAATGGT AATGCCAGGC GATAACATCA | 185 |
| *Helicobacter pylori* | CGACTGTAAC CGGTGTAGAA ATGTTTA | . . . | AAATGGT TATGCCTGGC GATAATGTCA | 186 |
| *Listeria moncytogenes* | TAGTAGTAAC TGGAGTAGAA ATGTTCC | . . . | AAATGGT AAYGCCTGGT GATAACATTG | 138 |
| *Micrococcus luteus* | CCACTGTCAC CGGCATCGAG ATGTTCC | . . . | AGATGGT CATGCCCGGC GACAACACCG | 187 |
| *Myocbacterium tuberculosis* | CCACCGTCAC CGGTGTGGAG ATGTTCC | . . . | AGATGGT GATGCCCGGT GACAACACCA | 188 |
| *Mycoplasma genitalium* | CAGTTGTTAC TGGAATTGAA ATGTTCA | . . . | AAATGGT TCTACCTGGT GATAATGCTT | 189 |

-continued

ANNEX I
Strategy for the selection from tuf sequences of the universal amplification primers

| Organism | 491 517 | | 776 802 | SEQ ID NO: |
|---|---|---|---|---|
| *Neisseria gonorrhoeae* | CCACCTGTAC CGGCGTTGAA ATGTTCC | . . . | AAATGGT AATGCCGGGT GAGAACGTAA | 190 |
| *Rickettsia prowazekii* | CGACTTGTAC AGGTGTAGAA ATGTTCA | . . . | AGATGGT TATGCCTGGA GATAATGCTA | 191 |
| *Salmonella typhrimurium* | CGACTTGTAC AGGTGTAGAA ATGTTCA | . . . | AGATGGT TATGCCTGGA GACAACATCA | 192 |
| *Shewanella putida* | CAACGTGTCA TGGTGTAGAA ATGTTCC | . . . | AGATGGT AATGCCAGGC GATAACATCA | 193 |
| *Stigmatella aurantiaca* | CGGTCATCAC GGGGGTGGAG ATGTTCC | . . . | AGATGGT GATGCCGGGA GACAACATCG | 194 |
| *Staphylococcus aureus* | CAACTGTTAC AGGTGTTGAA ATGTTCC | . . . | AAATGGT AATGCCTGGT GATAACGTTG | 140 |
| *Staphylococcus epidermidis* | CAACTGTTAC TGGTGTAGAA ATGTTCC | . . . | AAATGGT TATGCCTGGC GACAACGTTG | 141 |
| *Streptococcus agalacitae* | CAGTTGTTAC TGGTGTTGAA ATGTTCC | . . . | AAATGGT TATGCCTGGT GATAACGTTA | 144 |
| *Streptococcus pneumoniae* | CAGTTGTTAC TGGTGTTGAA ATGTTCC | . . . | AAATGGT AATGCCTGGT GATAACGTGA | 145 |
| *Streptococcus pyogenes* | CTGTTGTTAC TGGTGTTGAA ATGTTCC | . . . | AAATGGT TATGCCTGGT GATAACGTGA | 196 |
| *Thiobacillus cuprinus* | CCACCTGCAC CGGCGTGGAA ATGTTCA | . . . | AAATGGT CATGCCCGGC GATAATGTGA | 197 |
| *Treponema pallidum* | CAGTGGTTAC TGGCATTGAG ATGTTTA | . . . | ACATGGT GAAGCCGGGG GATAACACCA | 198 |
| *Ureaplasma urealyticum* | CTGTTGTTAC AGGAATTGAA ATGTTTA | . . . | ATTTGGT TATGCCAGGT GATGACGTTG | 199 |
| *Wolniella succinogenes* | CAACCGTAAC TGGCGTTGAG ATGTTCC | . . . | AGATGGT TATGCCTGGT GACAACGTTA | 200 |
| *Candida albicans* | GTGTTACCAC TGAAGTCAAR TCCGTTG | . . . | AGRAATT GGAAGAAAAT CCAAAATTCG | 120 |
| *Schizo-saccharomyces pombe* | GTGTCACTAC CGAAGTCAAG TCTGTTG | . . . | AGAAGAT TGAGGAGTCC CCTAAGTTTG | 200 |
| Human selected sequences | TGACAGGCAT TGAGATGTTC CACAAGA<br>ACIKKIAC IGGIGTIGAR ATGTT<br>SEQ IN NO: 23 | . . . | AGAAGGA GCTTGCCATG CCCGGGGAGG<br>ATGGT IATGCCIGGI GAIAAYRT<br>SEQ ID NO: 24[b] | 201 |
| Selected universal sequences[a] | ACIKKIAC IGGIGTIGAR ATGTT<br>SEQ ID NO: 225 | | AYRTT ITCICCIGGC ATIACCAT<br>SEQ ID NO: 226 | |

The sequence numbering refers to the *E. coli* tuf gene fragment. Underlined nucleotides are identical to the selected sequence or match that sequence.

[a]"I" stands for inosine which is a nucleotide analog that can bind to any of the four nucleotides A, C, G, or T. "K", "R" and "Y" designate nucleotide positions which are degenerate. "K" stands for T or G; "R" stands for A or G; "Y" stands for C or T.

[b]This sequence is the reverse complement of the above tuf sequence.

ANNEX II

Strategy for the selection from tuf sequences of the amplification primers specific for the genus *Enterococcus*

| Organism | 314 348 | | 401 435 | SEQ ID NO: |
|---|---|---|---|---|
| *Bacillus subtilis* | CGCGACACTG AAAAACCATT CATGATGCCA GTTGA | . . . | CGCGG ACAAGTTAAA GTCGGTGACG AAGTTGAAT | 148 |
| *Bacteroides fragilis* | CGCGATGTTG ATAAACCTTT CTTGATGCCG GTAGA | . . . | ACTGG TGTTATCCAT GTAGGTGATG AAATCGAAAT | 149 |
| *Burkholderia cepacia* | CGTGCAGTTG ACGGCGCGTT CCTGATGCCG GTGGA | . . . | CGCGG CATCGTGAAG GTCGGCGAAG AAATCGAAAT | 152 |
| *Chlamydia trachomatis* | AGAGAAATTG ACAAGCCTTT CTTAATGCCT ATTGA | . . . | CGTGG AATTGTTAAA GTTTCCGATA AAGTTCAGTT | 153 |
| *Corynebacterium diphteriae* | CGTGAGACCG ACAAGCCATT CCTCATGCCT ATCGA | . . . | CGTGG CTCCCTGAAG GTCAACGAGG ACGTCGAGAT | 126 |
| *Enterococcus avium* | CGTGATACTG ACAAACCATT CATGATGCCA GTCGA | . . . | CGTGG ACAAGTTCGC GTTGGTGACG AAGTTGAAAT | 131 |
| *Enterococcus faecalis* | CGTGATACTG ACAAACCATT CATGATGCCA GTCGA | . . . | CGTGG TGAAGTTCGC GTTGGTGACG AAGTTGAAAT | 132 |
| *Enterococcus faecium* | CGTGACAACG ACAAACCATT CATGATGCCA GTTGA | . . . | CGTGG ACAAGTTCGC GTTGGTGACC AAGTTGAAGT | 133 |
| *Enterococcus gallinarum* | CGTGATACTG ACAAACCATT CATGATGCCA GTCGA | . . . | CGTGG ACAAGTTCGC GTTGGTGATG AAGTAGAAAT | 134 |
| *Escherichia coli* | CGTGCGATTG ACAAGCCGTT CCTGCTGCCG ATCGA | . . . | CGCGG TATCATCAAA GTTGGTGAAG AAGTTGAAAT | 154 |
| *Gardnerella vaginalis* | CACGATCTTG ACAAGCCATT CTTGATGCCA ATCGA | . . . | CGTGG TAAGCTCCCA ATCAACACCC CAGTTGAGAT | 135 |
| *Haemophilus influenzae* | CGTGCGATTG ACCAACCGTT CCTTCTTCCA ATCGA | . . . | CGAGG TATTATCCGT ACAGGTGATG AAGTAGAAAT | 157 |
| *Helicobacter pylori* | AGAGACACTG AAAAAACTTT CTTGATGCCG GTTGA | . . . | AGAGG CGTGGTGAAA GTAGCCGATG AAGTGGAAAT | 158 |
| *Listeria monocytogenes* | CGTGATACTG ACAAACCATT CATGATGCCA GTTGA | . . . | CGTGG ACAAGTTAAA GTTGGTGACG AAGTAGAAGT | 138 |
| *Micrococcus* luteus | CGCGACAAGG ACAAGCCGTT CCTGATGCCG ATCGA | . . . | CGCGG CACCCTGAAG ATCAACTCCG AGGTCGAGAT | 159 |
| *Mycobacterium tuberculosis* | CGCGAGACCG ACAAGCCGTT CCTGATGCCG GTCGA | . . . | CGCGG CGTGATCAAC GTGAACGAGG AAGTTGAGAT | 160 |
| *Mycoplasma genitalium* | CGTGAAGTAG ATAAACCTTT CTTATTAGCA ATTGA | . . . | AGAGG TGAACTCAAA GTAGGTCAAG AAGTTGAAAT | 161 |
| *Neisseria gonorrhoeae* | CGTGCCGTGG ACAAACCATT CCTGCTGCCT ATCGA | . . . | CGAGG TATCATCCAC GTTGGTGACG AGATTGAAAT | 162 |
| *Salmonella typhimurium* | CGTGCGATTG ACAAGCCGTT CCTGCTGCCG ATCGA | . . . | CGCGG TATCATCAAA GTGGGCGAAG AAGTTGAAAT | 164 |
| *Shewanella putida* | CGTGACATCG ATAAGCCGTT CCTACTGCCA ATCGA | . . . | CGTGG TATTGTACGC GTAGGCGACG AAGTTGAAAT | 165 |
| *Staphylococcus aureus* | CGTGATTCTG ACAAACCATT CATGATGCCA GTTGA | . . . | CGTGG TCAAATCAAA GTTGGTGAAG AAGTTGAAAT | 140 |
| *Staphylococcus epidermidis* | CGTGATTCTG ACAAACCATT CATGATGCCA GTTGA | . . . | CGTGG TCAAATCAAA GTWGGTGAAG AAGTTGAAAT | 141 |
| *Staphylococcus saprophyticus* | CGTGATTCTG ACAAACCATT CATGATGCCA GTTGA | . . . | CGTGG TCAAATCAAA GTCGGTGAAG AAATCGARAT | 142 |
| *Streptococcus agalacticae* | CGTGATACTG ACAAACCTTT ACTTCTTCCA GTTGA | . . . | CGTGG TACTGTTCGT GTCAACGACG AAGTTGAAAT | 144 |

-continued

ANNEX II
Strategy for the selection from tuf sequences of the amplification primers specific for the genus *Enterococcus*

| Organism | 314 . . . 348 | 401 . . . 435 | SEQ ID NO: |
|---|---|---|---|
| *Streptococcus pneumoniae* | CGTGACACTG ACAAACCATT GCTTCTTCCA GTCGA . . . | CGTGG TATCGTTAAA GTCAACGACG AAATCGAAAT | 145 |
| *Streptococcus pyogenes* | CGCGACACTG ACAAACCATT GCTTCTTCCA GTCGA . . . | CGTGG TACTGTTCGT GTCAACGACG AAATCGAAAT | 167 |
| *Ureaplasma urealyticum* | CGTAGTACTG ACAAACCATT CTTATTAGCA ATTGA . . . | CGTGG TGTATTAAAA GTTAATGATG AGGTTGAAAT | 170 |
| Selected sequences | TACTG ACAAACCATT CATGATG<br>SEQ ID NO: 13 | GTTCGC GTTGGTGACG AAGTT<br>SEQ ID NO: 14[a] | |
| Selected genus-specific primer sequences | TACTG ACAAACCATT CATGATG | AACTTC GTCACCAACG CGAAC | |

The sequence numbering refers to the *E. faecalis* tuf gene fragment. Underlined nucleotides are identical to the selected sequence or match that sequence.
[a]This sequence is the reverse complement of the tuf sequence.
NOTE:
The above primers also amplify tuf sequences from *Abiotrophia* species; this genus has recently been related to the *Enterococcus* genus by 16S rRNA analysis.

ANNEX III
Strategy for the selection from tuf sequences of the amplification primers specific for the genus *Staphylococcus*

| Organism | 385 . . . 420 | 579 . . . 611 | SEQ ID NO: |
|---|---|---|---|
| *Bacillus subtilis* | TGGCCGTGTA GAACGCGGAC AAGTTAAAGT CGG . . . | TTG CTAAACCAGG TACAATCACT CCACACAGCA | 148 |
| *Bacteroides fragilis* | AGGTCGTATC GAAACTGGTG TTATCCATGT AGG . . . | TTT GTAAACCGGG TCAGATTAAA CCTCACTCTA | 149 |
| *Burkholderia cepacia* | GGGTCGTGTC GAGCGCGGCA TCGTGAAGGT CGG . . . | TGG CGAAGCCGGG TTCGATCACG CCGCACACGC | 152 |
| *Chlamydia trachomatis* | TGGACGTATT GAGCGTGGAA TTGTTAAAGT TTC . . . | TTT GCTTGCCAAA CAGTGTTAAA CCTCATACAC | 153 |
| *Corynebacterium diphteriae* | CGGCCGTGTT GAGCGTGGCT CCCTGAAGGT CAA . . . | TTG TTAAGCCAGG CGCTTACACC CCTCACACCG | 126 |
| *Enterococcus faecalis* | AGGACGTGTT GAACGTGGTG AAGTTCGCGT TGG . . . | TAG CTAAACCAGC TACAATCACT CCACACACAA | 132 |
| *Enterococcus faecium* | AGGTCGTGTT GAACGTGGAC AAGTTCGCGT TGG . . . | TAG CTAAACCAGG TACAATCACA CCTCRTACAA | 133 |
| *Escherichia coli* | CGGTCGTGTA GAACGCGGTA TCATCAAAGT TGG . . . | TGG CTAAGCCGGG CACCATCAAG CCGCACACCA | 154 |
| *Gardnerella vaginalis* | CGGTCGTGTT GAGCGTGGTA AGCTCCCAAT CAA . . . | TGG CTGCTCCAGG TTCTGTGACT CCACACACCA | 135 |
| *Haemophilus influenzae* | AGGTCGTGTA GAACGAGGTA TTATCCGTAC AGG . . . | TAG CGAAACCAGG TTCAATCACA CCACACACTG | 157 |
| *Helicobacter pylori* | AGGTAGGATT GAAAGAGGCG TGGTGAAAGT AGG . . . | TAT GCAAACCAGG TTCTATCACT CCGCACAAGA | 158 |
| *Listeria monocytogenes* | TGGACGTGTT GAACGTGGAC AAGTTAAAGT TGG . . . | TAG CTAAACCAGG TTCGATTACT CCACACACTA | 138 |
| *Micrococcus luteus* | CGGTCGCGCC GAGCGCGGCA CCCTGAAGAT CAA . . . | TGG TGGAGCCGGG CTCCATCACC CCGCACACCA | 159 |

-continued

ANNEX III
Strategy for the selection from tuf sequences of the amplification primers specific for the genus *Staphylococcus*

| Organism | 385 420 | 579 611 | SEQ ID NO: |
|---|---|---|---|
| *Mycobacterium tuberculosis* | CGGACGTGTG GAGCGCGGCG TGATCAACGT GAA . . . | TCA CCAAGCCCGG CACCACCACG CCGCACACCG | 160 |
| *Mycoplasma genitalium* | AGGAAGAGTT GAAAGAGGTG AACTCAAAGT AGG . . . | TAG CAAAACCAGG CTCTATTAAA CCGCACAAGA | 161 |
| *Neisseria gonorrhoeae* | CGGCCGTGTA GAGCGAGGTA TCATCCACGT TGG . . . | TGG CCAAACGGGG TACTATCACT CCTCACACCA | 162 |
| *Salmonella typhimurium* | CGGTCGTGTA GAGCGCGGTA TCATCAAAGT GGG . . . | TGG CTAAGCCGGG CACCATCAAG CCGCACACCA | 164 |
| *Shewanella putida* | AGGTCGTGTT GAGCGTGGTA TTGTACGCGT AGG . . . | TAG CGAAGCCAGG TTCAATCAAC CCACACACTA | 165 |
| *Staphylococcus aureus* | AGGCCGTGTT GAACGTGGTC AAATCAAAGT TGG . . . | TAG CTGCTCCTGG TTCAATTACA CCACATACTG | 140 |
| *Staphylococcus epidermidis* | AGGCCGTGTT GAACGTGGTC AAATCAAAGT WGG . . . | TAG CTGCTCCTGG TTCTATTACA CCACACACAA | 141 |
| *Staphylococcus saprophyticus* | AGGCCGTGTT GAACGTGGTC AAATCAAAGT CGG . . . | TAG CTGCTCCTGG TACTATCACA CCACATACAA | 142 |
| *Stapylococcus simulans* | AGGCCGTGTT GAACGTGGTC AAATCAAAGT CGG . . . | TAG CAGCTCCTGG CTCTATTACT CCACACACAA | 141 |
| *Streptococcus agalacticae* | AGGACGTATC GACCGTGGTA CTGTTCGTGT CAA . . . | TTG CTAAACCAGG TTCAATCAAC CCACACACTA | 144 |
| *Streptococcus pneumoniae* | AGGACGTATC GACCGTGGTA TCGTTAAAGT CAA . . . | TCG CTAAACCAGG TTCAATCAAC CCACACACTA | 145 |
| *Ureaplasma urealyticum* | TGGACGTGTT GAACGTGGTG TATTAAAAGT TAA . . . | TTG TAAAACCAGG ATCAATTAAA CCTCACCGTA | 170 |
| Selected sequences | CCGTGTT GAACGTGGTC AAATCAAA SEQ ID NO: 17 | GCTCCTGG YWCWATYACA CCACAYA SEQ ID NO: 18[b] | |
| Selected genus-specific primer sequences[a] | CCGTGTT GAACGTGGTC AAATCAAA | TRTGTGGT GTRATWGWRC CAGGAGC | |

The sequence numbering refers to the *S. aureus* tuf gene fragment. Underlined nucleotides are identical to the selected sequence or match that sequence.
[a]"R", "W", and "Y" designate nucleotide positions which are degenerate. "R" stands for A or G; "W", for A or T; "Y", for C or T.
[b]This sequence is the reverse complement of the above tuf sequence.

ANNEX IV
Strategy for the selection from eut sequences of the amplification primers specific for the species *Candida albicans*

| Organism | 58 90 | 181 213 | SEQ ID NO: |
|---|---|---|---|
| *Candida albicans* | CGTCAAGAAG GTTGGTTACA ACCCAAAGAC TGT . . . | CAA ATCCGCTAAA GTTACTGGTA AGACCTTGTT | 120 |
| *Candida glabrata* | CATCAAGAAG GTCGGTTACA ACCCAAAGAC TGT . . . | CAA GGCTGGTGTC GTCAAGGGTA AGAYCTTGTT | 121 |
| *Candida krusei* | CATCAAGAAG GTTGGTTACA ACCCAAAGAC TGT . . . | CAA GGCAGGTGTT GTTAAGGGTA AGACCTTATT | 122 |
| *Candida parapsilosis* | CGTCAAGAAG GTTGGTTACA ACCCTAAAGC TGT . . . | TAA AGCTGGTAAG GTTACCGGTA AGACCTTGTT | 123 |

-continued

ANNEX IV
Strategy for the selection from eut sequences of the amplification primers specific for the species *Candida albicans*

| Organism | 58 90 | 181 213 | SEQ ID NO: |
|---|---|---|---|
| *Candida tropicalis* | CGTCAAGAAG GTTGGTTACA ACCCTAAGGC TGT . . . | CAA GGCTGGTAAG GTTACCGGTA AGACTTTGTT | 124 |
| *Schizo-saccharomyces pombe* | CATCAAGAAG GTCGGTTTCA ACCCCAAGAC CGT . . . | CAA GGCTGGTGTC GTCAAGGGTA AGACTCTTTT | |
| Human | GGAGATCCGG GAGCTGCTCA CCGAGTTTGG CTA . . . | GTT AGGCCTGAAG TCTGTGCAGA AGCTACTGGA | |
| *Chlamydia trachomatis* | GGAGCTGCGC GAGCTGCTCA GCAAGTACGG TTA . . . | CAA ATG....... ..TATTCTGG AGCTGATGAA | 153 |
| *Corynebacterium diphteriae* | GGAGATCCRT GAGCTGCTCG CTGAGCAGGA TTA . . . | GAA GTGGACCCAG TCCATCATCG ACCTCATGCA | 126 |
| *Enterococcus faecalis* | GGAAGTTCGT GACTTATTAT CAGAATACGA TTT . . . | ... ...TGAAGAA AAAATCTTAG AATTAATGGC | 132 |
| *Escherichia coli* | GGAAGTTCGT GAACTTCTGT CTCAGTACGA CTT . . . | ... ..GGGAAGCG AAAATCCTGG AACTGGCTGG | 154 |
| *Flavobacterium ferrugineum* | CGAGGTTCGC GAAGAACTGA CTAAACGCGG TTT . . . | ... ..GGGTTAAA GAAATTGAAA ACCTGATGGA | 156 |
| *Gardnerella vaginalis* | AGAGGTCCGT GACCTCCTCG AAGAAAACGG CTT . . . | CAA GTGGGTAGAG ACCGTCAAGG AACTCATGAA | 135 |
| *Haemophilus influenzae* | GGAAGTTCGT GAACTTCTAT CTCAATATGA CTT . . . | ..GGGAAGAA AAAATCCTTG AGTTAGCAAA | 157 |
| *Listeria monocytogenes* | GGAAATTCGT GATCTATTAA CTGAATATGA ATT . . . | ... ..GGGAAGCT AAAATTGACG AGTTAATGGA | 138 |
| *Micrococcus luteus* | GGAAGTCCGT GAGTTGCTGG CTGCCCAGGA ATT . . . | CAA GTGGGTCGAG TCTGTCACAC AGTTGATGGA | 159 |
| *Neisseria gonorrhoeae* | GGAAATCCGC GACCTGCTGT CCAGCTACGA CTT . . . | ... ..ACGAAGAA AAAATCTTCG AACTGGCTAC | 162 |
| *Salmonella typhimurium* | GGAAGTTCGC GAACTGCTGT CTCAGTACGA CTT . . . | ... ..GGGAACGC AAAATCATCG AACTGGCTGG | 164 |
| *Staphylococcus aureus* | GGAAGTTCGT GACTTATTAA GCGAATATGA CTT . . . | ... ...CGAAGAA AAAATCTTAG AATTAATGGA | 140 |
| *Streptococcus pneumoniae* | GGAAATCCGT GACCTATTGT CAGAATACGA CTT . . . | ... ...CGAAGAC ATCGTTATGG AATTGATGAA | 145 |
| *Treponema pallidum* | AGAGGTGCGT GATGCGCTTG CTGGATATGG GTT . . . | GGA GGATGCAGCT TGTATTGAGG AACTGCTTGC | 169 |
| Selected sequence | CAAGAAG GTTGGTTACA ACCCAAAGA SEQ ID NO: 11 | ATCCGGTAAA GTTACTGGTA AGACCCT SEQ ID NO: 12[a] | |
| Selected species-specific primer sequences | CAAGAAG GTTGGTTACA ACCCAAAGA | AGGTCTTACC AGTAACTTTAC CGGAT | |

The sequence numbering refers to the *Candida albicans* tuf gene fragment. Underlined nucleotides are identical to the selected sequence or match that sequence.
[a]This sequence is the reverse complement of the above tuf sequence ANNEX V
Strategy for the selection from the recA gene of the amplification primers specific for the genus *Streptococcus*

| Organism | | SEQ ID NO: |
|---|---|---|
| *Bordetella pertussis* | CTCGAGATCA CCGACGCGCT GGTGCGCTCG GGCTC . . . GGCCC GCCTGATGAG CCAGGCGCTG CGCAAGCTGA | 203 |
| *Burholderia cepacia* | CTCGAAATCA CCGATGCGCT GGTGCGCTCG GGCTC . . . GGCCC GCCTGATGTC GCAGGCGCTG CGCAAGCTGA | 204 |
| *Campylobacter jejuni* | TTAGAAATTG TAGAAACTAT AGCAAGAAGT GGCGC . . . AGCAA GACTTATGTC TCAAGCTCTA AGAAAACTTA | 205 |
| *Chamydia trachomatis* | TTGAGTATTG CAGAGCTCTT AGCGCGTTCT GGACG . . . AGCTC GCATGATGTC GCAGGCTCTA CGCAAATTAA | 206 |
| *Clostridium perfringens* | TTAGAAATAA CAGAAGCTTT AGTTAGATCA GGAGC . . . AGCTA GATTAATGTC ACAAGCCTTA AGAAAGTTAA | 207 |
| *Corynebacterium pseudo-tuberculosis* | CTGGAGATTG CAGATATGCT TGTTCGCTCT GGAGC . . . AGCGC GTTTGATGAG TCAGGCGCTG CGTAAGCTTG | 208 |
| *Enterobacterium agglomerans* | CTGGAAATCT GTGATGCGCT GACCCGTTCA GGCGC . . . AGCTC GTATGATGAG CCAGGCGATG CGTAAGCTTG | 209 |
| *Enterococcus faecium* | TTAGAGATTG CCGATGCCTT AGTTTCAAGT GGTGC . . . AGCTC GACTAATGTC TCAAGCACTA CGTAAATTAT | 210 |
| *Escherichia coli* | CTGGAAATCT GTGACGCCCT GGCGCGTTCT GGCGC . . . GGCAC GTATGATGAG CCAGGCGATG CGTAAGCTGG | 211 |
| *Haemophilus influenzae* | GCGAACAGAA GAATAGAATT TTAATGCATT ACCGC . . . GACCT GTGAGTTTAC GCAAAGCTTG AGACATTAAA | 212 |
| *Helicobacter pylori* | TTAGAAATTT TAGAAACGAT CACCAGAAGC GGAGG . . . AGCAA GGCTTATGAG CCATGCGTTA AGAAAAATCA | 213 |
| *Lactococcus lactis* | CTTCAAATTG CTGAAAAATT GATTACTTCT GGAGC . . . AGCAC GTATGATGTC ACAAGCCATG CGTAAACTTG | 214 |
| *Legionella pneumophila* | CTGGAAATTA CTGATATGCT GGTGCGTTCT GCAGC . . . GGCAA GATTGATGTC GCAAGCCCTG CGTAAATTGA | 215 |
| *Mycoplasma gentalium* | TTTGCTCTTA TCGAATCATT AATTAAAACA AACAA . . . TGCAA GAATGATGTC AAAAGGTTTG CGAAGAATAC | 216 |
| *Proteus mirabilis* | CTGGAAATTT GTGATGCATT ATCTCGCTCT GGTGC . . . CGCAC GTATGATGAG CCAAGCTATG CGTAAACTAG | 217 |
| *Pseudomonas aeruginosa* | CTGGAAATCA CCGACATGCT GGTGCGCTCC AACGC . . . GGCAC GCCTGATGTC CCAGGCGCTG CGCAAGATCA | 218 |
| *Serratia Marcescens* | CTGGAAATCT GTGATGCGCT GACCCGCTCC GGCGC . . . GGCGC GCATGATGAG CCAGGCGATG CGTAAGCTGG | 219 |
| *Shigella flexneri* | CTGGAAATCT GTGACGCCCT GGCGCGTTCT GGCGC . . . GGCAC GTATGATGAG CCAGGCGATG CGTAAGCTGG | 220 |
| *Staphylococcus aureus* | CTTGAAATCG CCGAAGCATT TGTTAGAAGT GGTGC . . . AGCTC GTTTAATGTC ACAAGCGTTA CGTAAACTTT | 221 |
| *Streptococcus gordonii* | TTAGAAATTG CAGGAAAATT GATTGACTCT GGGGC . . . ..... .......... .......... .......... | 32 |
| *Streptococcus mutans* | CTTGAAATTG CAGGGAAATT GATTGATTCT GGCGC . . . AGCAC GCATGATGAG TCAAGCGATG CGTAAATTAT | 33 |
| *Streptococcus pneumoniae* | CTTGAGATTG CGGGAAAATT GATTGACTCA GGTGC . . . GGCTC GTATGATGAG CCAGGCCATG CGTAAACTTG | 34 |
| *Steptococcus pyogenes* | CTTGAAATTG CAGGTAAATT GATTGATTCT GGTGC . . . AGCAC GTATGATGAG TCAGGCCATG CGTAAATTAT | 35 |
| *Streptococcus salivarius* | CTCGAAATTG CAGGTAAGCT GATTGACTCT GGTGC . . . AGCGC GTATGATGAG TCAAGCCATG CGTAAACTTT | 36 |

-continued

ANNEX V
Strategy for the selection from the recA gene of the amplification primers specific for the genus *Streptococcus*

| Organism | | | SEQ ID NO: |
|---|---|---|---|
| *Vibrio cholerae* | CTGGAAATTT GTGATGCACT GGCTCGCTCT GGTGC . . . | AGCGC GTATGTTGTC GCAAGCAATG CGTAAACTGA | 222 |
| *Yersinia pestis* | CTGGAAATTT GTGATGCGCT GACTCGCTCT GGTGC . . . | CGCGC GTATGATGAG CCAGGCTATG CGTAAGCTGG | 223 |
| Selected sequence[a] | GAAATTG CAGGIAAATT GATTGA SEQ ID NO: 21 | ATGATGAG TCAIGCCATG CGTAA SED ID NO: 22[b] | 224 |
| Selected genus-specific primer sequences[b] | GAAATTG CAGGIAAATT GATTGA | TTACGCAT GGCITGACTC ATCAT | |

The sequence numbering refer to the *S. pneumoniae* recA sequence. Underlined nucleotides are identical to the selected sequence or match that sequence.
[a]"I" stands for inosine which is a nucleotide analog that can bind to any of the four nucleotides A, C, G, or T.
[b]This sequence is the reverse complement of the above recA sequence.

Annex VI:
Specific and ubiquitous primers for DNA amplification

| SEQ ID NO | Nucleotide sequence | Originating DNA fragment: SEQ ID NO | Originating DNA fragment: Nucleotide position |
|---|---|---|---|
| Bacterial species: *Enterococcus faecium* | | | |
| 1 | 5'-TGC TTT AGC AAC AGC CTA TCA G | 26[a] | 273-294 |
| 2[b] | 5'-TAA ACT TCT TCC GGC ACT TCG | 26[a] | 468-488 |
| Bacterial species: *Listeria monocytogenes* | | | |
| 3 | 5'-TGC GGC TAT AAA TGA AGA GGC | 27[a] | 339-359 |
| 4[b] | 5'-ATC CGA TGA TGC TAT GGC TTT | 27[a] | 448-468 |
| Bacterial species: *Neisseria meningitidis* | | | |
| 5 | 5'-CCA GCG GTA TTG TTT GGT GGT | 28[a] | 56-76 |
| 6[b] | 5'-CAG GCG GCC TTT AAT AAT TTC | 28[a] | 212-232 |
| Bacterial species: *Staphylococcus saprophyticus* | | | |
| 7 | 5'-AGA TCG AAT TCC ACA TGA AGG TTA TTA TGA | 29[c] | 290-319 |
| 8[b] | 5'-TCG CTT CTC CCT CAA CAA TCA AAC TAT CCT | 29[c] | 409-438 |
| Bacterial species: *Streptococcus agalactiae* | | | |
| 9 | 5'-TTT CAC CAG CTG TAT TAG AAG TA | 30[a] | 59-81 |
| 10[b] | 5'-GTT CCC TGA ACA TTA TCT TTG AT | 30[a] | 190-212 |
| Fungal species: *Candida albicans* | | | |
| 11 | 5'-CAA GAA GGT TGG TTA CAA CCC AAA GA | 120[c] | 61-86 |
| 12[b] | 5'-AGG TCT TAC CAG TAA CTT TAC CGG AT | 120[c] | 184-209 |

-continued

Annex VI:
Specific and ubiquitous primers for DNA amplification

| SEQ ID NO | Nucleotide sequence | Originating DNA fragment: SEQ ID NO | Originating DNA fragment: Nucleotide position |
|---|---|---|---|

[a]Sequences from databases.
[b]These sequences are from the opposite DNA strand of the sequence of the originating fragment given in the Sequence Listing.
[c]Sequences determined by our group.

Annex VI:
Specific and ubiquitous primers for DNA amplification (continues on next page)

| SEQ ID NO | Nucleotide sequence | Originating DNA fragment: SEQ ID NO | Originating DNA fragment: Nucleotide position |
|---|---|---|---|
| Bacterial genus: *Enterococcus* | | | |
| 13 | 5'-TAC TGA CAA ACC ATT CAT GAT G | 131-134[a,b] | 319-340[c] |
| 14[d] | 5'-AAC TTC GTC ACC AAC GCG AAC | 131-134 | 410-430[c] |
| Bacterial genus: *Neisseria* | | | |
| 15 | 5'-CTG GCG CGG TAT GGT CGG TT | 31[e] | 21-40[f] |
| 16[d] | 5'-GCC GAC GTT GGA AGT GGT AAA G | 31[e] | 102-123[f] |
| Bacterial genus: *Staphylococcus* | | | |
| 17 | 5'-CCG TGT TGA ACG TGG TCA AAT CAA A | 140-143[a,b] | 391-415[g] |
| 18[d] | 5'-TRT GTG GTG TRA TWG WRC CAG GAG C | 140-143[a,b] | 584-608[g] |
| 19 | 5'-ACA ACG TGG WCA AGT WTT AGC WGC T | 140-143[a,b] | 562-583[g] |
| 20[d] | 5'-ACC ATT TCW GTA CCT TCT GGT AAG T | 140-143[a,b] | 729-753[g] |

-continued

Annex VI: Specific and ubiquitous primers for DNA amplification (continues on next page)

| SEQ ID NO | Nucleotide sequence | Originating DNA fragment SEQ ID NO | Originating DNA fragment Nucleotide position |
|---|---|---|---|
| Bacterial genus: *Streptococcus* | | | |
| 21 | 5'-GAA ATT GCA GGI AAA TTG ATT GA | 32-36[e] | 418-440[h] |
| 22[d] | 5'-TTA CGC ATG GCI TGA CTC ATC AT | 32-36[e] | 547-569[h] |
| Universal primers | | | |
| 23 | 5'-ACI KKI ACI GGI GTI GAR ARG TT | 118-146[a,b] 147-171[a,e] | 493-515[i] |
| 24[d] | 5'-AYR TTI TCI CCI GGC ATI ACC AT | 118-146[a,b] 147-171[a,e] | 778-800[i] |

[a]These sequences were aligned to derive the corresponding primer.
[b]tuf sequences determined by our group.
[c]The nucleotide positions refer to the *E. faecalis* tuf gene fragment (SEQ ID NO: 132).
[d]These sequences are from the opposite DNA strand of the sequence of the originating fragment given in the Sequence Listing.
[e]Sequences from databases.
[f]The nucleotide positions refer to the *N. meningitidis* asd gene fragment (SEQ ID NO: 31).
[g]The nucleotide positions refer to the *S. aureus* tuf gene fragment (SEQ ID NO: 140).
[h]The nucleotide positions refer to the *S. pneumoniae* recA gene (SEQ ID NO: 34).
[i]The nucleotide positions refer to the *E. coli* tuf gene fragment (SEQ ID NO: 154).

Annex VI: Specific and ubiquitous primers for DNA amplification

| SEQ ID NO | Nucleotide sequence | Originating DNA fragment SEQ ID NO | Originating DNA fragment Nucleotide position |
|---|---|---|---|
| Antibiotic resistance gene: $bla_{tem}$ | | | |
| 37 | 5'-CTA TGT GGC GCG GTA TTA TC | — | — |
| 38 | 5'-CGC AGT GTT ATC ACT CAT GG | — | — |
| 39 | 5'-CTG AAT GAA GCC ATA CCA AA | — | — |
| 40 | 5'-ATC AGC AAT AAA CCA GCC AG | — | — |
| Antibiotic resistance gene: $bla_{shv}$ | | | |
| 41 | 5'-TTA CCA TGA GCG ATA ACA GC | — | — |
| 42 | 5'-CTC ATT CAG TTC CGT TTC CC | — | — |
| 43 | 5'-CAG CTG CTG GAG TGG ATG GT | — | — |
| 44 | 5'-CGG TCT GCT TTG TTA TTC GG | — | — |
| Antibiotic resistance gene: $bla_{rob}$ | | | |
| 45 | 5'-TAC GCC AAC ATC GTG GAA AG | — | — |
| 46 | 5'-TTG AAT TTG GCT TCT TCG GT | — | — |
| 47 | 5'-GGG ATA CAG AAA CGG GAC AT | — | — |
| 48 | 5'-TAA ATC TTT TTC AGG CAG CG | — | — |

-continued

Annex VI: Specific and ubiquitous primers for DNA amplification

| SEQ ID NO | Nucleotide sequence | Originating DNA fragment SEQ ID NO | Originating DNA fragment Nucleotide position |
|---|---|---|---|
| Antibiotic resistance gene: $bla_{oxa}$ | | | |
| 49 | 5'-GAT GGT TTG AAG GGT TTA TTA TAA G | 110[a] | 686-710 |
| 50[b] | 5'-AAT TTA GTG TGT TTA GAA TGG TGA T | 110[a] | 802-826 |
| Antibiotic resistance gene: blaZ | | | |
| 51 | 5'-ACT TCA ACA CCT GCT GCT TTC | 111[a] | 511-531 |
| 52[b] | 5'-TGA CCA CTT TTA TCA GCA ACC | 111[a] | 663-683 |
| Antibiotic resistance gene: aadB | | | |
| 53 | 5'-GGC AAT AGT TGA AAT GCT CG | — | — |
| 54 | 5'-CAG CTG TTA CAA CGG ACT GG | — | — |
| Antibiotic resistance gene: aacC1 | | | |
| 55 | 5'-TCT ATG ATC TCG CAG TCT CC | — | — |
| 56 | 5'-ATC GTC ACC GTA ATC TGC TT | — | — |

[a]Sequences from databases.
[b]These sequences are from the opposite DNA strand of the sequence of the originating fragment given in the Sequence Listing.

Annex VI: Specific and ubiquitous primers for DNA amplification

| SEQ ID NO | Nucleotide sequence | Originating DNA fragment SEQ ID NO | Originating DNA fragment Nucleotide position |
|---|---|---|---|
| Antibiotic resistance gene: aacC2 | | | |
| 57 | 5'-CAT TCT CGA TTG CTT TGC TA | — | — |
| 58 | 5'-CCG AAA TGC TTC TCA AGA TA | — | — |
| Antibiotic resistance gene: aacC3 | | | |
| 59 | 5'-CTG GAT TAT GGC TAC GGA GT | — | — |
| 60 | 5'-AGC AGT GTG ATG GTA TCC AG | — | — |
| Antibiotic resistance gene: aac6'-IIa | | | |
| 61 | 5'-GAC TCT TGA TGA AGT GCT GG | 112[a] | 123-142 |
| 62[b] | 5'-CTG GTC TAT TCC TCG CAC TC | 112[a] | 284-303 |
| 63 | 5'-TAT GAG AAG GCA GGA TTC GT | 112[a] | 445-464 |
| 64[b] | 5'-GCT TTC TCT CGA AGG CTT GT | 112[a] | 522-541 |
| Antibiotic resistance gene: aacA4 | | | |
| 65 | 5'-GAG TTG CTG TTC AAT GAT CC | — | — |
| 66 | 5'-GTG TTT GAA CCA TGT ACA CG | — | — |

-continued

Annex VI: Specific and ubiquitous primers for DNA amplification

| SEQ ID NO | Nucleotide sequence | Originating DNA fragment SEQ ID NO | Originating DNA fragment Nucleotide position |
|---|---|---|---|
| Antibiotic resistance gene: aad(6') | | | |
| 173 | 5'-TCT TTA GCA GAA CAG GAT GAA | — | — |
| 174 | 5'-GAA TAA TTC ATA TCC TCC G | — | — |
| Antibiotic resistance gene: vanA | | | |
| 67 | 5'-TGT AGA GGT CTA GCC CGT GT | — | — |
| 68 | 5'-ACG GGG ATA ACG ACT GTA TG | — | — |
| 69 | 5'-ATA AAG ATG ATA GGC CGG TG | — | — |
| 70 | 5'-TGC TGT CAT ATT GTC TTG CC | — | — |
| Antibiotic resistance gene: vanB | | | |
| 71 | 5'-ATT ATC TTC GGC GGT TGC TC | 116[a] | 22-41 |
| 72[b] | 5'-GAC TAT CGG CTT CCC ATT CC | 116[a] | 171-190 |
| 73 | 5'-CGA TAG AAG CAG CAG GAC AA | 116[a] | 575-594 |
| 74 | 5'-CTG ATG GAT GCG GAA GAT AC | 116[a] | 713-732 |

[a]Sequences from databases.

[b]These sequences are from the opposite DNA strand of the sequence of the originating fragment given in the Sequence Listing.

Annex VI: Specific and ubiquitous primers for DNA amplification

| SEQ ID NO | Nucleotide sequence | Originating DNA fragment SEQ ID NO | Originating DNA fragment Nucleotide position |
|---|---|---|---|
| Antibiotic resistance gene: vanC | | | |
| 75 | 5'-GCC TTA TGT ATG AAC AAA TGG | 117[a] | 373-393 |
| 76[b] | 5'-GTG ACT TTW GTG ATC CCT TTT GA | 117[a] | 541-563 |
| Antibiotic resistance gene: msrA | | | |
| 77 | 5'-TCC AAT CAT TGC ACA AAA TC | — | — |
| 78 | 5'-AAT TCC CTC TAT TTG GTG GT | — | — |
| 79 | 5'-TCC CAA GCC AGT AAA GCT AA | — | — |
| 80 | 5'-TGG TTT TTC AAC TTC TTC CA | — | — |
| Antibiotic resistance gene: satA | | | |
| 81 | 5'-TCA TAG AAT GGA TGG CTC AA | — | — |
| 82 | 5'-AGC TAC TAT TGC ACC ATC CC | — | — |
| Antibiotic resistance gene: aac(6')-aph(2") | | | |
| 83 | 5'-CAA TAA GGG CAT ACC AAA AAT C | — | — |

-continued

Annex VI: Specific and ubiquitous primers for DNA amplification

| SEQ ID NO | Nucleotide sequence | Originating DNA fragment SEQ ID NO | Originating DNA fragment Nucleotide position |
|---|---|---|---|
| 84 | 5'-CCT TAA CAT TTG TGG CAT TAT C | — | — |
| 85 | 5'-TTG GGA AGA TGA AGT TTT TAG A | — | — |
| 86 | 5'-CCT TTA CTC CAA TAA TTT GGC T | — | — |
| Antibiotic resistance gene: vat | | | |
| 87 | 5'-TTT CAT CTA TTC AGG ATG GG | — | — |
| 88 | 5'-GGA GCA ACA TTC TTT GTG AC | — | — |
| Antibiotic resistance gene: vga | | | |
| 89 | 5'-TGT GCC TGA AGA AGG TAT TG | — | — |
| 90 | 5'-CGT GTT ACT TCA CCA CCA CT | — | — |
| Antibiotic resistance gene: ermA | | | |
| 91 | 5'-TAT CTT ATC GTT GAG AAG GGA TT | 113[a] | 370-392 |
| 92[b] | 5'-CTA CAC TTG GCT TAG GAT GAA A | 113[a] | 487-508 |

[a]Sequences from databases.

[b]These sequences are from the opposite DNA strand of the sequence of the originating fragment given in the Sequence Listing.

Annex VI: Specific and ubiquitous primers for DNA amplification

| SEQ ID NO | Nucleotide sequence | Originating DNA fragment SEQ ID NO | Originating DNA fragment Nucleotide position |
|---|---|---|---|
| Antibiotic resistance gene: ermB | | | |
| 93 | 5'-CTA TCT GAT TGT TGA AGA AGG ATT | 114[a] | 366-389 |
| 94[b] | 5'-GTT TAC TCT TGG TTT AGG ATG AAA | 114[a] | 484-507 |
| Antibiotic resistance gene: ermC | | | |
| 95 | 5'-CTT GTT GAT CAC GAT AAT TTC C | 115[a] | 214-235 |
| 96[b] | 5'-ATC TTT TAG CAA ACC CGT ATT C | 115[a] | 382-403 |
| Antibiotic resistance gene: mecA | | | |
| 97 | 5'-AAC AGG TGA ATT ATT AGC ACT TGT AAG | — | — |
| 98 | 5'-ATT GCT GTT AAT ATT TTT TGA GTT GAA | — | — |
| Antibiotic resistance gene: int | | | |
| 99 | 5'-GTG ATC GAA ATC CAG ATC C | — | — |
| 100 | 5'-ATC CTC GGT TTT CTG GAA G | — | — |
| 101 | 5'-CTG GTC ATA CAT GTG ATG G | — | — |
| 102 | 5'-GAT GTT ACC CGA GAG CTT G | — | — |

-continued

Annex VI:
Specific and ubiquitous primers for DNA amplification

| SEQ ID NO | Nucleotide sequence | Originating DNA fragment SEQ ID NO | Originating DNA fragment Nucleotide position |
|---|---|---|---|
| Antibiotic resistance gene: sul | | | |
| 103 | 5'-TTA AGC GTG CAT AAT AAG CC | — | — |
| 104 | 5'-TTG CGA TTA CTT CGC CAA CT | — | — |
| 105 | 5'-TTT ACT AAG CTT GCC CCT TC | — | — |
| 106 | 5'-AAA AGG CAG CAA TTA TGA GC | — | — |

[a]Sequences from databases.
[b]These sequences are from the opposite DNA strand of the sequence of the originating fragment given in the Sequence Listing.

What is claimed is:

1. A method of simultaneously assaying for the presence and identity or identities of more than one target bacterial or fungal species selected from the group consisting of *Enterococcus faecium, Listeria monocytogenes, Neisseria meningitidis, Streptococcus agalactiae*, and *Candida albicans*, and at least one target bacterial antibiotic resistance gene selected from the group consisting of $bla_{tem}$, $bla_{shv}$, $bla_{rob}$, $bla_{oxa}$, blaZ, aadB, aacC1, aacC2, aacC3, aac6'-IIa, aacA4, aad(6'), vanA, vanB, vanC, msrA, sarA, aac(6') aph(2"), vat, vga, ermA, ermB, ermC, mecA, int and sul, in a sample comprising:

simultaneously contacting the sample with a plurality of species-specific primer pairs, wherein each pair of said species-specific primer pairs specifically hybridizes to and amplifies nucleic acids from only one target bacterial or fungal species selected from the group consisting of *Enterococcus faecium, Listeria monocFtogenes, Neisseria meningitidis, Streptococcus agalactiae*, and *Candida albicans*; and one or more antibiotic resistance gene primer pairs, wherein each pair of said one or more antibiotic resistance gene primer pairs specifically hybridizes to and amplifies only one antibiotic resistance gene selected from the group consisting of $bla_{tem}$, $bla_{shv}$, $bla_{rob}$, $bla_{oxa}$, blaZ, aadB, aacC1, aacC2, aacC3, aac6'-IIa, aacA4, aad (6'), vanA, vanB, vanC, msrA, satA, aac(6')-aph(2"), vat, vga, ermA, ermB, ermC, mecA, int and sul;

amplifying target nucleic acids from the sample under a single amplification protocol; and detecting various amplified products produced by the single amplification protocol, wherein the detecting step is adapted to differentiate said amplification products such that the presence and identity or identities of said more than one target bacterial or fungal species and said at least one target bacterial antibiotic resistance gene are simultaneously assayed.

2. The method of claim 1, the amplification protocol comprises an amplification method selected from the group consisting of:

(a) polymerase chain reaction (PCR),
(b) ligase chain reaction,
(c) nucleic acid sequence-based amplification,
(d) self-sustained sequence replication,
(e) strand displacement amplification,
(f) branched DNA signal amplification,
(g) nested PCR, and
(h) multiplex PCR.

3. The method of claim 2 wherein the amplification method is PCR.

4. The method of claim 3, wherein the amplification method is multiplex PCR.

5. The method of claim 3, wherein, in each amplification cycle of said PCR, an annealing step is 30 seconds at 45-55° C. and a denaturation step is only one second at 95° C. without any time for an elongation step.

6. The method of claim 1, wherein the detecting step comprises hybridizing said amplification products with a probe.

7. The method of claim 1, wherein said sample consists of one or more bacterial colonies.

8. The method of claim 1, wherein said detecting step comprises resolving said amplification products by gel electrophoresis.

9. The method of claim 1, wherein said detecting step comprises contacting said amplification products with one or more probes, wherein each of the one or more probes only specifically hybridizes to one of the amplification products amplified from the nucleic acids from only one of said more than one target bacterial or fungal species and wherein each of the one or more probes is coupled to a fluorescent dye.

10. The method of claim 9, further comprising measuring the amount of fluorescence produced by said fluorescent dye.

* * * * *

SEQUENCE LISTING

<160> NUMBER OF SEQ ID NOS: 226

<210> SEQ ID NO 1
<211> LENGTH: 22
<212> TYPE: DNA
<213> ORGANISM: Enterococcus faecium

<400> SEQUENCE: 1
tgctttagca acagcctatc ag 22

<210> SEQ ID NO 2
<211> LENGTH: 21
<212> TYPE: DNA
<213> ORGANISM: Enterococcus faecium

<400> SEQUENCE: 2
taaacttctt ccggcacttc g 21

<210> SEQ ID NO 3
<211> LENGTH: 21
<212> TYPE: DNA
<213> ORGANISM: Listeria monocytogenes

<400> SEQUENCE: 3
tgcggctata aatgaagagg c 21

<210> SEQ ID NO 4
<211> LENGTH: 21
<212> TYPE: DNA
<213> ORGANISM: Listeria monocytogenes

<400> SEQUENCE: 4
atccgatgat gctatggctt t 21

<210> SEQ ID NO 5
<211> LENGTH: 21
<212> TYPE: DNA
<213> ORGANISM: Neisseria meningitidis

<400> SEQUENCE: 5
ccagcggtat tgtttggtgg t 21

<210> SEQ ID NO 6
<211> LENGTH: 21
<212> TYPE: DNA

-continued

<213> ORGANISM: Neisseria meningitidis

<400> SEQUENCE: 6
caggcggcct ttaataattt c 21

<210> SEQ ID NO 7
<211> LENGTH: 30
<212> TYPE: DNA
<213> ORGANISM: Staphylococcus saprophyticus

<400> SEQUENCE: 7
agatcgaatt ccacatgaag gttattatga 30

<210> SEQ ID NO 8
<211> LENGTH: 30
<212> TYPE: DNA
<213> ORGANISM: Staphylococcus saprophyticus

<400> SEQUENCE: 8
tcgcttctcc ctcaacaatc aaactatcct 30

<210> SEQ ID NO 9
<211> LENGTH: 23
<212> TYPE: DNA
<213> ORGANISM: Streptococcus agalactiae

<400> SEQUENCE: 9
tttcaccagc tgtattagaa gta 23

<210> SEQ ID NO 10
<211> LENGTH: 23
<212> TYPE: DNA
<213> ORGANISM: Streptococcus agalactiae

<400> SEQUENCE: 10
gttccctgaa cattatcttt gat 23

<210> SEQ ID NO 11
<211> LENGTH: 26
<212> TYPE: DNA
<213> ORGANISM: Candida albicans

<400> SEQUENCE: 11
caagaaggtt ggttacaacc caaaga 26

<210> SEQ ID NO 12
<211> LENGTH: 26
<212> TYPE: DNA
<213> ORGANISM: Candida albicans

<400> SEQUENCE: 12
aggtcttacc agtaacttta ccggat 26

<210> SEQ ID NO 13
<211> LENGTH: 22
<212> TYPE: DNA
<213> ORGANISM: Enterococcus sp.

<400> SEQUENCE: 13
tactgacaaa ccattcatga tg 22

<210> SEQ ID NO 14
<211> LENGTH: 21
<212> TYPE: DNA

-continued

<213> ORGANISM: Enterococcus sp.

<400> SEQUENCE: 14
aacttcgtca ccaacgcgaa c 21

<210> SEQ ID NO 15
<211> LENGTH: 20
<212> TYPE: DNA
<213> ORGANISM: Artificial Sequence
<220> FEATURE:
<223> OTHER INFORMATION: synthetic DNA

<400> SEQUENCE: 15
ctggcgcggt atggtcggtt 20

<210> SEQ ID NO 16
<211> LENGTH: 22
<212> TYPE: DNA
<213> ORGANISM: Artificial Sequence
<220> FEATURE:
<223> OTHER INFORMATION: synthetic DNA

<400> SEQUENCE: 16
gccgacgttg gaagtggtaa ag 22

<210> SEQ ID NO 17
<211> LENGTH: 25
<212> TYPE: DNA
<213> ORGANISM: Staphylococcus sp.

<400> SEQUENCE: 17
ccgtgttgaa cgtggtcaaa tcaaa 25

<210> SEQ ID NO 18
<211> LENGTH: 25
<212> TYPE: DNA
<213> ORGANISM: Artificial Sequence
<220> FEATURE:
<223> OTHER INFORMATION: synthetic DNA

<400> SEQUENCE: 18
trtgtggtgt ratwgwrcca ggagc 25

<210> SEQ ID NO 19
<211> LENGTH: 25
<212> TYPE: DNA
<213> ORGANISM: Artificial Sequence
<220> FEATURE:
<223> OTHER INFORMATION: synthetic DNA

<400> SEQUENCE: 19
acaacgtggw caagtwttag cwgct 25

<210> SEQ ID NO 20
<211> LENGTH: 25
<212> TYPE: DNA
<213> ORGANISM: Artificial Sequence
<220> FEATURE:
<223> OTHER INFORMATION: synthetic DNA

<400> SEQUENCE: 20
accatttcwg taccttctgg taagt 25

<210> SEQ ID NO 21
<211> LENGTH: 23
<212> TYPE: DNA

-continued

<213> ORGANISM: Artificial Sequence
<220> FEATURE:
<223> OTHER INFORMATION: synthetic DNA
<220> FEATURE:
<221> NAME/KEY: modified_base
<222> LOCATION: (12)
<223> OTHER INFORMATION: i

<400> SEQUENCE: 21
gaaattgcag gnaaattgat tga 23

<210> SEQ ID NO 22
<211> LENGTH: 23
<212> TYPE: DNA
<213> ORGANISM: Artificial Sequence
<220> FEATURE:
<223> OTHER INFORMATION: synthetic DNA
<220> FEATURE:
<221> NAME/KEY: modified_base
<222> LOCATION: (12)
<223> OTHER INFORMATION: i

<400> SEQUENCE: 22
ttacgcatgg cntgactcat cat 23

<210> SEQ ID NO 23
<211> LENGTH: 23
<212> TYPE: DNA
<213> ORGANISM: Artificial Sequence
<220> FEATURE:
<223> OTHER INFORMATION: synthetic DNA
<220> FEATURE:
<221> NAME/KEY: modified_base
<222> LOCATION: (3)
<223> OTHER INFORMATION: i
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i

<400> SEQUENCE: 23
acnkknacng gngtngarat gtt 23

<210> SEQ ID NO 24
<211> LENGTH: 23
<212> TYPE: DNA
<213> ORGANISM: Artificial Sequence
<220> FEATURE:
<223> OTHER INFORMATION: synthetic DNA
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:

<221> NAME/KEY: modified_base
<222> LOCATION: (18)
<223> OTHER INFORMATION: i

<400> SEQUENCE: 24
ayrttntcnc cnggcatnac cat 23

<210> SEQ ID NO 25
<211> LENGTH: 10
<212> TYPE: DNA
<213> ORGANISM: Artificial Sequence
<220> FEATURE:
<223> OTHER INFORMATION: synthetic DNA

<400> SEQUENCE: 25
tcgcttctcc 10

<210> SEQ ID NO 26
<211> LENGTH: 600
<212> TYPE: DNA
<213> ORGANISM: Enterococcus faecium

<400> SEQUENCE: 26
ttcttagaga cattgaatat gccttatgtc ggcgcaggcg tattgaccag tgcatgtgcc 60
atggataaaa tcatgaccaa gtatatttta caagctgctg gtgtgccgca agttccttat 120
gtaccagtac ttaagaatca atggaaagaa aatcctaaaa aagtatttga tcaatgtgaa 180
ggttctttgc tttatccgat gtttgtcaaa cctgcgaata tgggttctag tgtcggcatt 240
acaaaggcag aaaaccgaga agagctgcaa aatgctttag caacagccta tcagtatgat 300
tctcgagcaa tcgttgaaca aggaattgaa gcgcgcgaaa tcgaagttgc tgtattagga 360
aatgaagatg ttcggacgac tttgcctggc gaagtcgtaa aagacgtagc attctatgat 420
tatgaagcca aatatatcaa taataaaatc gaaatgcaga ttccagccga agtgccggaa 480
gaagtttatc aaaaagcgca agagtacgcg aagttagctt acacgatgtt aggtggaagc 540
ggattgagcc ggtgcgattt ctttttgaca aataaaaatg aattattcct gaatgaatta 600

<210> SEQ ID NO 27
<211> LENGTH: 1920
<212> TYPE: DNA
<213> ORGANISM: Listeria monocytogenes

<400> SEQUENCE: 27
gtgggattaa acagatttat gcgtgcgatg atggtggttt tcattactgc caattgcatt 60
acgattaacc ccgacataat atttgcagcg acagatagcg aagattctag tctaaacaca 120
gatgaatggg aagaagaaaa aacagaagag caaccaagcg aggtaaatac gggaccaaga 180
tacgaaactg cacgtgaagt aagttcacgt gatattaaag aactagaaaa atcgaataaa 240
gtgagaaata cgaacaaagc agacctaata gcaatgttga aagaaaaagc agaaaaaggt 300
ccaaatatca ataataacaa cagtgaacaa actgagaatg cggctataaa tgaagaggct 360
tcaggagccg accgaccagc tatacaagtg gagcgtcgtc atccaggatt gccatcggat 420
agcgcagcgg aaattaaaaa aagaaggaaa gccatagcat catcggatag tgagcttgaa 480
agccttactt atccggataa accaacaaaa gtaaataaga aaaaagtggc gaaagagtca 540
gttgcggatg cttctgaaag tgacttagat tctagcatgc agtcagcaga tgagtcttca 600
ccacaacctt taaaagcaaa ccaacaacca tttttcccta aagtatttaa aaaaataaaa 660
gatgcgggga aatgggtacg tgataaaatc gacgaaaatc ctgaagtaaa gaaagcgatt 720

-continued

```
gttgataaaa gtgcagggtt aattgaccaa ttattaacca aaaagaaaag tgaagaggta    780
aatgcttcgg acttcccgcc accacctacg gatgaagagt taagacttgc tttgccagag    840
acaccaatgc ttcttggttt taatgctcct gctacatcag aaccgagctc attcgaattt    900
ccaccaccac ctacggatga agagttaaga cttgctttgc cagagacgcc aatgcttctt    960
ggttttaatg ctcctgctac atcggaaccg agctcgttcg aatttccacc gcctccaaca   1020
gaagatgaac tagaaatcat ccgggaaaca gcatcctcgc tagattctag ttttacaaga   1080
ggggatttag ctagtttgag aaatgctatt aatcgccata gtcaaaattt ctctgatttc   1140
ccaccaatcc caacagaaga agagttgaac gggagaggcg gtagaccaac atctgaagaa   1200
tttagttcgc tgaatagtgg tgattttaca gatgacgaaa acagcgagac aacagaagaa   1260
gaaattgatc gcctagctga tttaagagat agaggaacag gaaaacactc aagaaatgcg   1320
ggtttttttac cattaaatcc gtttgctagc agcccggttc cttcgttaag tccaaaggta   1380
tcgaaaataa gcgaccgggc tctgataagt gacataacta aaaaaacgcc atttaagaat   1440
ccatcacagc cattaaatgt gtttaataaa aaaactacaa cgaaaacagt gactaaaaaa   1500
ccaacccctg taaagaccgc accaaagcta gcagaacttc ctgccacaaa accacaagaa   1560
accgtactta gggaaaataa aacacccttt atagaaaaac aagcagaaac aaacaagcag   1620
tcaattaata tgccgagcct accagtaatc caaaaagaag ctacagagag cgataaagag   1680
gaaatgaaac cacaaaccga ggaaaaaatg gtagaggaaa gcgaatcagc taataacgca   1740
aacggaaaaa atcgttctgc tggcattgaa gaaggaaaac taattgctaa aagtgcagaa   1800
gacgaaaaag cgaaggaaga accagggaac catacgacgt taattcttgc aatgttagct   1860
attggcgtgt tctctttagg ggcgtttatc aaaattattc aattaagaaa aaataattaa   1920
```

<210> SEQ ID NO 28
<211> LENGTH: 415
<212> TYPE: DNA
<213> ORGANISM: Neisseria meningitidis

<400> SEQUENCE: 28

```
taccggtacg ctaaatattg gtgatgtatt ggatattatg atttgggaag cgccgccagc     60
ggtattgttt ggtggtggcc tttcttcgat gggctcgggt agtgcgcaac aaaccaagtt    120
gccggagcaa ctggtgacgg cacgtggtac ggtttctgtg ccgtttgttg gcgatatttc    180
ggtggtcggt aaaacgcctg gtcaggttca ggaaattatt aaaggccgcc tgaaaaaaat    240
ggccaatcag ccgcaagtga tggtgcgctt ggtgcagaat aatgcggcaa atgtatcggt    300
gattcgcgca ggcaatagtg tgcgtatgcc gttgacggca gccggtgagc gtgtgttgga    360
tgcggtggct gcggtaggtg gttcaacggc aaatgtgcag gatacgaatg tgcag         415
```

<210> SEQ ID NO 29
<211> LENGTH: 438
<212> TYPE: DNA
<213> ORGANISM: Staphylococcus saprophyticus

<400> SEQUENCE: 29

```
tcgcttctcc agaagaaatt ttagaaacat atctagaaaa tcccaaatta gataaaccgt     60
ttatattatg tgaatacgca catgcaatgg gaaattcacc aggagatctt aatgcatatc    120
aaacattaat tgaaaaatat gatagtttta ttggcggttt tgtttgggaa tggtgtgatc    180
atagcattca ggttgggata aaggaaggta aaccaatttt tagatatggt ggagattttg    240
gtgaggcctt acatgacggt aatttttgtg ttgatggtat tgtttcgcca gatcgaattc    300
```

-continued

```
cacatgaagg ttattatgag tttaaacatg aacatagacc tttgagattg gttaacgaag    360

aggattatcg gtttacattg aagaatcaat ttgattttac aaatgcggag gatagtttga    420

ttgttgaggg agaagcga                                                  438
```

<210> SEQ ID NO 30
<211> LENGTH: 768
<212> TYPE: DNA
<213> ORGANISM: Streptococcus agalactiae

<400> SEQUENCE: 30

```
atgaacgtta cacatatgat gtatctatct ggaactctag tggctggtgc attgttattt     60

tcaccagctg tattagaagt acatgctgat caagtgacaa ctccacaagt ggtaaatcat    120

gtaaatagta ataatcaagc ccagcaaatg gctcaaaagc ttgatcaaga tagcattcag    180

ttgagaaata tcaaagataa tgttcaggga acagattatg aaaaaccggt taatgaggct    240

attactagcg tggaaaaatt aaagacttca ttgcgtgcca accctgagac agtttatgat    300

ttgaattcta ttggtagtcg tgtagaagcc ttaacagatg tgattgaagc aatcactttt    360

tcaactcaac atttaacaaa taaggttagt caagcaaata ttgatatggg atttgggata    420

actaagctag ttattcgcat tttagatcca tttgcttcag ttgattcaat taaagctcaa    480

gttaacgatg taaaggcatt agaacaaaaa gttttaactt atcctgattt aaaaccaact    540

gatagagcta ccatctatac aaaatcaaaa cttgataagg aaatctggaa tacacgcttt    600

actagagata aaaaagtact taacgtcaaa gaatttaaag tttacaatac tttaaataaa    660

gcaatcacac atgctgttgg agttcagttg aatccaaatg ttacggtaca acaagttgat    720

caagagattg taacattaca agcagcactt caaacagcat taaaataa                 768
```

<210> SEQ ID NO 31
<211> LENGTH: 421
<212> TYPE: DNA
<213> ORGANISM: Neisseria meningitidis

<400> SEQUENCE: 31

```
atgaaagtag gtttcgtcgg ctggcgcggt atggtcggtt cggttttgat gcagcgtatg     60

aaagaagaaa acgacttcgc ccacattccc gaagcgtttt tctttaccac ttccaacgtc    120

ggcggcgcac gccctgattt cggtcaggcg gctaaaacat tattggacgc gaacaacgtt    180

gccgagctgg caaaaatgga catcatcgtt acctgccaag gcggcgacta caccaaatcc    240

gtcttccaag ccctgcgcga cagcggctgg aacggctact ggattgacgc ggcatcctcg    300

ctgcgtatga aagacgacgc gattatcgtc ctcgaccccg tcaaccgcaa cgtcatcgac    360

aacggcctca aaaacggcgt gaaaaactac atcggcggca actgtaccgt ttccctgatg    420

c                                                                    421
```

<210> SEQ ID NO 32
<211> LENGTH: 213
<212> TYPE: DNA
<213> ORGANISM: Streptococcus gordonii

<400> SEQUENCE: 32

```
ttcatagacg ctgagcacgc tttggatcca tcttacgcgg ctgctctagg tgtaaatatt     60

gatgagctgt tgctatctca accagattct ggtgagcaag gtttagaaat tgcaggaaaa    120

ttgattgact ctggggcagt tgatttagtt gtcatcgact ctgttgcagc tcttgtacca    180

cgtgcggaaa tcgatggaga tatcggtgat agc                                 213
```

<210> SEQ ID NO 33
<211> LENGTH: 692
<212> TYPE: DNA
<213> ORGANISM: Streptococcus mutans

<400> SEQUENCE: 33
gggccggaat cttctggtaa gacaactgtc gctcttcatg ctgctgctca ggcgcaaaaa 60
gatggcggta ttgccgcttt cattgatgca gaacatgccc ttgatccagc ctatgctgct 120
gctcttggcg ttaatattga tgagcttttg ctttcacaac cagattcagg agaacagggt 180
cttgaaattg cagggaaatt gattgattct ggcgctgttg atttagttgt tgttgactca 240
gtggcagctt tagtaccacg tgcggagatt gacggagata ttggtaatag tcatgttggc 300
ttacaagcac gcatgatgag tcaagcgatg cgtaaattat cagcttcaat caataaaaca 360
aaaaccattg ctatttttat taatcaattg cgggaaaaag ttggtattat gtttggtaat 420
ccagaaacaa cccctggcgg gcgtgccttg aagttttatt cttctgtgcg tcttgatgtc 480
cgcggcaata ctcaaattaa aggaaccggg gaacaaaaag acagcaatat tggtaaagag 540
accaaaatta aagttgttaa aaataaagtt gctccaccat ttaaggaagc ttttgtagaa 600
attatatatg gtgaaggcat ttctcgtaca ggtgaattag ttaagattgc cagtgatttg 660
ggaattatcc aaaaagctgg agcttggtac tc 692

<210> SEQ ID NO 34
<211> LENGTH: 1204
<212> TYPE: DNA
<213> ORGANISM: Streptococcus pneumoniae

<400> SEQUENCE: 34
atggcgaaaa aaccaaaaaa attagaagaa atttcaaaaa aatttggggc agaacgtgaa 60
aaggccttga atgacgctct taaattgatt gagaaagact ttggtaaagg atcaatcatg 120
cgtttgggtg aacgtgcgga gcaaaaggtg caagtgatga gctcaggttc tttagctctt 180
gacattgccc ttggctcagg tggttatcct aagggacgta tcatcgaaat ctatggccca 240
gagtcatctg gtaagacaac ggttgccctt catgcagttg cacaagcgca aaaagaaggt 300
gggattgctg cctttatcga tgcggaacat gcccttgatc cagcttatgc tgcggccctt 360
ggtgtcaata ttgacgaatt gctcttgtct caaccagact caggagagca aggtcttgag 420
attgcgggaa aattgattga ctcaggtgca gttgatcttg tcgtagtcga ctcagttgct 480
gcccttgttc ctcgtgcgga aattgatgga gatatcggag atagccatgt tggtttgcag 540
gctcgtatga tgagccaggc catgcgtaaa cttggcgcct ctatcaataa aaccaaaaca 600
attgccattt ttatcaacca attgcgtgaa aaagttggag tgatgtttgg aaatccagaa 660
acaacaccgg gcggacgtgc tttgaaattc tatgcttcag tccgcttgga tgttcgtggt 720
aatacacaaa ttaagggaac tggtgatcaa aaagaaacca atgtcggtaa agaaactaag 780
attaaggttg taaaaaataa ggtagctcca ccgtttaagg aagccgtagt tgaaattatg 840
tacggagaag gaatttctaa gactggtgag cttttgaaga ttgcaagcga tttggatatt 900
atcaaaaaag caggggcttg gtattcttac aaagatgaaa aaattgggca aggttctgag 960
aatgctaaga aatacttggc agagcaccca gaaatctttg atgaaattga taagcaagtc 1020
cgttctaaat ttggcttgat tgatggagaa gaagtttcag aacaagatac tgaaaacaaa 1080
aaagatgagc caaagaaaga agaagcagtg aatgaagaag ttccgcttga cttaggcgat 1140
gaacttgaaa tcgaaattga agaataagct gttaaagcag tggagaaatc cgctactttt 1200

-continued tcga 1204

<210> SEQ ID NO 35
<211> LENGTH: 981
<212> TYPE: DNA
<213> ORGANISM: Streptococcus pyogenes

<400> SEQUENCE: 35
atgcgttcag gaagtctagc tcttgatatt gcttggatag ctggtggtta tcctaaagga 60
cgtatcatcg aaatctatgg tccagagtct tccggtaaaa cgactgtggc tttacatgct 120
gtagcacaag ctcaaaaaga aggtggaatc gcagccttta tcgatgccga gcatgcgctt 180
gatccagctt atgctgctgc gcttggggtt aatattgatg aacttctctt gtctcaacca 240
gattctggag aacaaggact tgaaattgca ggtaaattga ttgattctgg tgcggttgac 300
ctggttgttg tcgattcagt agcagcttta gtgccacgtg ctgaaattga tggtgatatt 360
ggcgatagcc atgtcggatt gcaagcacgt atgatgagtc aggccatgcg taaattatca 420
gcttctatta ataaaacaaa aactatcgca atctttatca accaattgcg tgaaaaagtt 480
ggtgtgatgt ttggaaatcc tgaaacaaca ccaggtggtc gagctttgaa attctatgct 540
tctgttcggc tggatgtgcg tggaaacaac caaattaaag gaactggtga ccaaaagata 600
gccagcattg gtaaggagac caaaatcaag gttgttaaaa acaaggtcgc tccgccattt 660
aaggtagcag aagttgaaat catgtatggg gaaggtattt ctcgtacagg ggagcttgtg 720
aaaattgctt ctgatttgga cattatccaa aaagcaggtg cttggttctc ttataatggt 780
gagaagattg gccaaggttc tgaaaatgct aagcgttatt tggccgatca tccacaattg 840
tttgatgaaa tcgaccgtaa agtacgtgtt aaatttggtt tgcttgaaga aagcgaagaa 900
gaatctgcta tggcagtagc atcagaagaa accgatgatc ttgctttaga tttagataat 960
ggtattgaaa ttgaagatta a 981

<210> SEQ ID NO 36
<211> LENGTH: 312
<212> TYPE: DNA
<213> ORGANISM: Streptococcus salivarius

<400> SEQUENCE: 36
gcgtatgcac gagctctagg tgttaatatc gatgagcttc ttttgtcgca gcctgattct 60
ggtgagcaag gtctcgaaat tgcaggtaag ctgattgact ctggtgcagt ggatttagtt 120
gttgttgact cagttgcggc cttcgtacca cgtgcagaaa ttgatggaga tagtggtgac 180
agtcatgtag gacttcaagc gcgtatgatg agtcaagcca tgcgtaaact ttctgcatct 240
attaataaaa caaaaacgat tgctatcttt attaaccagt tgcgtgaaaa agttggtatc 300
atgtttggta ac 312

<210> SEQ ID NO 37
<211> LENGTH: 20
<212> TYPE: DNA
<213> ORGANISM: Artificial Sequence
<220> FEATURE:
<223> OTHER INFORMATION: synthetic DNA

<400> SEQUENCE: 37
ctatgtggcg cggtattatc 20

<210> SEQ ID NO 38
<211> LENGTH: 20
<212> TYPE: DNA

<213> ORGANISM: Artificial Sequence
<220> FEATURE:
<223> OTHER INFORMATION: synthetic DNA

<400> SEQUENCE: 38
cgcagtgtta tcactcatgg 20

<210> SEQ ID NO 39
<211> LENGTH: 20
<212> TYPE: DNA
<213> ORGANISM: Artificial Sequence
<220> FEATURE:
<223> OTHER INFORMATION: synthetic DNA

<400> SEQUENCE: 39
ctgaatgaag ccataccaaa 20

<210> SEQ ID NO 40
<211> LENGTH: 20
<212> TYPE: DNA
<213> ORGANISM: Artificial Sequence
<220> FEATURE:
<223> OTHER INFORMATION: synthetic DNA

<400> SEQUENCE: 40
atcagcaata aaccagccag 20

<210> SEQ ID NO 41
<211> LENGTH: 20
<212> TYPE: DNA
<213> ORGANISM: Artificial Sequence
<220> FEATURE:
<223> OTHER INFORMATION: synthetic DNA

<400> SEQUENCE: 41
ttaccatgag cgataacagc 20

<210> SEQ ID NO 42
<211> LENGTH: 20
<212> TYPE: DNA
<213> ORGANISM: Artificial Sequence
<220> FEATURE:
<223> OTHER INFORMATION: synthetic DNA

<400> SEQUENCE: 42
ctcattcagt tccgtttccc 20

<210> SEQ ID NO 43
<211> LENGTH: 20
<212> TYPE: DNA
<213> ORGANISM: Artificial Sequence
<220> FEATURE:
<223> OTHER INFORMATION: synthetic DNA

<400> SEQUENCE: 43
cagctgctgc agtggatggt 20

<210> SEQ ID NO 44
<211> LENGTH: 20
<212> TYPE: DNA
<213> ORGANISM: Artificial Sequence
<220> FEATURE:
<223> OTHER INFORMATION: synthetic DNA

<400> SEQUENCE: 44
cgctctgctt tgttattcgg 20

-continued

<210> SEQ ID NO 45
<211> LENGTH: 20
<212> TYPE: DNA
<213> ORGANISM: Artificial Sequence
<220> FEATURE:
<223> OTHER INFORMATION: synthetic DNA

<400> SEQUENCE: 45
tacgccaaca tcgtggaaag 20

<210> SEQ ID NO 46
<211> LENGTH: 20
<212> TYPE: DNA
<213> ORGANISM: Artificial Sequence
<220> FEATURE:
<223> OTHER INFORMATION: synthetic DNA

<400> SEQUENCE: 46
ttgaatttgg cttcttcggt 20

<210> SEQ ID NO 47
<211> LENGTH: 20
<212> TYPE: DNA
<213> ORGANISM: Artificial Sequence
<220> FEATURE:
<223> OTHER INFORMATION: synthetic DNA

<400> SEQUENCE: 47
gggatacaga aacgggacat 20

<210> SEQ ID NO 48
<211> LENGTH: 20
<212> TYPE: DNA
<213> ORGANISM: Artificial Sequence
<220> FEATURE:
<223> OTHER INFORMATION: synthetic DNA

<400> SEQUENCE: 48
taaatctttt tcaggcagcg 20

<210> SEQ ID NO 49
<211> LENGTH: 25
<212> TYPE: DNA
<213> ORGANISM: Escherichia coli

<400> SEQUENCE: 49
gatggtttga agggtttatt ataag 25

<210> SEQ ID NO 50
<211> LENGTH: 25
<212> TYPE: DNA
<213> ORGANISM: Escherichia coli

<400> SEQUENCE: 50
aatttagtgt gtttagaatg gtgat 25

<210> SEQ ID NO 51
<211> LENGTH: 21
<212> TYPE: DNA
<213> ORGANISM: Enterococcus faecalis

<400> SEQUENCE: 51
acttcaacac ctgctgcttt c 21

<210> SEQ ID NO 52

-continued

<211> LENGTH: 21
<212> TYPE: DNA
<213> ORGANISM: Enterococcus faecalis

<400> SEQUENCE: 52
tgaccacttt tatcagcaac c 21

<210> SEQ ID NO 53
<211> LENGTH: 20
<212> TYPE: DNA
<213> ORGANISM: Artificial Sequence
<220> FEATURE:
<223> OTHER INFORMATION: synthetic DNA

<400> SEQUENCE: 53
ggcaatagtt gaaatgctcg 20

<210> SEQ ID NO 54
<211> LENGTH: 20
<212> TYPE: DNA
<213> ORGANISM: Artificial Sequence
<220> FEATURE:
<223> OTHER INFORMATION: synthetic DNA

<400> SEQUENCE: 54
cagctgttac aacggactgg 20

<210> SEQ ID NO 55
<211> LENGTH: 20
<212> TYPE: DNA
<213> ORGANISM: Artificial Sequence
<220> FEATURE:
<223> OTHER INFORMATION: synthetic DNA

<400> SEQUENCE: 55
tctatgatct cgcagtctcc 20

<210> SEQ ID NO 56
<211> LENGTH: 20
<212> TYPE: DNA
<213> ORGANISM: Artificial Sequence
<220> FEATURE:
<223> OTHER INFORMATION: synthetic DNA

<400> SEQUENCE: 56
atcgtcaccg taatctgctt 20

<210> SEQ ID NO 57
<211> LENGTH: 20
<212> TYPE: DNA
<213> ORGANISM: Artificial Sequence
<220> FEATURE:
<223> OTHER INFORMATION: synthetic DNA

<400> SEQUENCE: 57
cattctcgat tgctttgcta 20

<210> SEQ ID NO 58
<211> LENGTH: 20
<212> TYPE: DNA
<213> ORGANISM: Artificial Sequence
<220> FEATURE:
<223> OTHER INFORMATION: synthetic DNA

<400> SEQUENCE: 58
ccgaaatgct tctcaagata 20

<210> SEQ ID NO 59
<211> LENGTH: 20
<212> TYPE: DNA
<213> ORGANISM: Artificial Sequence
<220> FEATURE:
<223> OTHER INFORMATION: synthetic DNA

<400> SEQUENCE: 59
ctggattatg gctacggagt 20

<210> SEQ ID NO 60
<211> LENGTH: 20
<212> TYPE: DNA
<213> ORGANISM: Artificial Sequence
<220> FEATURE:
<223> OTHER INFORMATION: synthetic DNA

<400> SEQUENCE: 60
agcagtgtga tggtatccag 20

<210> SEQ ID NO 61
<211> LENGTH: 20
<212> TYPE: DNA
<213> ORGANISM: Pseudomonas aeruginosa

<400> SEQUENCE: 61
gactcttgat gaagtgctgg 20

<210> SEQ ID NO 62
<211> LENGTH: 20
<212> TYPE: DNA
<213> ORGANISM: Pseudomonas aeruginosa

<400> SEQUENCE: 62
ctggtctatt cctcgcactc 20

<210> SEQ ID NO 63
<211> LENGTH: 20
<212> TYPE: DNA
<213> ORGANISM: Pseudomonas aeruginosa

<400> SEQUENCE: 63
tatgagaagg caggattcgt 20

<210> SEQ ID NO 64
<211> LENGTH: 20
<212> TYPE: DNA
<213> ORGANISM: Pseudomonas aeruginosa

<400> SEQUENCE: 64
gctttctctc gaaggcttgt 20

<210> SEQ ID NO 65
<211> LENGTH: 20
<212> TYPE: DNA
<213> ORGANISM: Artificial Sequence
<220> FEATURE:
<223> OTHER INFORMATION: synthetic DNA

<400> SEQUENCE: 65
gagttgctgt tcaatgatcc 20

<210> SEQ ID NO 66
<211> LENGTH: 20
<212> TYPE: DNA

-continued

<213> ORGANISM: Artificial Sequence
<220> FEATURE:
<223> OTHER INFORMATION: synthetic DNA

<400> SEQUENCE: 66
gtgtttgaac catgtacacg 20

<210> SEQ ID NO 67
<211> LENGTH: 20
<212> TYPE: DNA
<213> ORGANISM: Artificial Sequence
<220> FEATURE:
<223> OTHER INFORMATION: synthetic DNA

<400> SEQUENCE: 67
tgtagaggtc tagcccgtgt 20

<210> SEQ ID NO 68
<211> LENGTH: 20
<212> TYPE: DNA
<213> ORGANISM: Artificial Sequence
<220> FEATURE:
<223> OTHER INFORMATION: synthetic DNA

<400> SEQUENCE: 68
acggggataa cgactgtatg 20

<210> SEQ ID NO 69
<211> LENGTH: 20
<212> TYPE: DNA
<213> ORGANISM: Artificial Sequence
<220> FEATURE:
<223> OTHER INFORMATION: synthetic DNA

<400> SEQUENCE: 69
ataaagatga taggccggtg 20

<210> SEQ ID NO 70
<211> LENGTH: 20
<212> TYPE: DNA
<213> ORGANISM: Artificial Sequence
<220> FEATURE:
<223> OTHER INFORMATION: synthetic DNA

<400> SEQUENCE: 70
tgctgtcata ttgtcttgcc 20

<210> SEQ ID NO 71
<211> LENGTH: 20
<212> TYPE: DNA
<213> ORGANISM: Enterococcus faecalis

<400> SEQUENCE: 71
attatcttcg gcggttgctc 20

<210> SEQ ID NO 72
<211> LENGTH: 20
<212> TYPE: DNA
<213> ORGANISM: Enterococcus faecalis

<400> SEQUENCE: 72
gactatcggc ttcccattcc 20

<210> SEQ ID NO 73
<211> LENGTH: 20
<212> TYPE: DNA

-continued

<213> ORGANISM: Enterococcus faecalis

<400> SEQUENCE: 73
cgatagaagc agcaggacaa 20

<210> SEQ ID NO 74
<211> LENGTH: 20
<212> TYPE: DNA
<213> ORGANISM: Enterococcus faecalis

<400> SEQUENCE: 74
ctgatggatg cggaagatac 20

<210> SEQ ID NO 75
<211> LENGTH: 21
<212> TYPE: DNA
<213> ORGANISM: Enterococcus gallinarum

<400> SEQUENCE: 75
gccttatgta tgaacaaatg g 21

<210> SEQ ID NO 76
<211> LENGTH: 23
<212> TYPE: DNA
<213> ORGANISM: Enterococcus gallinarum

<400> SEQUENCE: 76
gtgactttwg tgatcccttt tga 23

<210> SEQ ID NO 77
<211> LENGTH: 20
<212> TYPE: DNA
<213> ORGANISM: Artificial Sequence
<220> FEATURE:
<223> OTHER INFORMATION: synthetic DNA

<400> SEQUENCE: 77
tccaatcatt gcacaaaatc 20

<210> SEQ ID NO 78
<211> LENGTH: 20
<212> TYPE: DNA
<213> ORGANISM: Artificial Sequence
<220> FEATURE:
<223> OTHER INFORMATION: synthetic DNA

<400> SEQUENCE: 78
aattccctct atttggtggt 20

<210> SEQ ID NO 79
<211> LENGTH: 20
<212> TYPE: DNA
<213> ORGANISM: Artificial Sequence
<220> FEATURE:
<223> OTHER INFORMATION: synthetic DNA

<400> SEQUENCE: 79
tcccaagcca gtaaagctaa 20

<210> SEQ ID NO 80
<211> LENGTH: 20
<212> TYPE: DNA
<213> ORGANISM: Artificial Sequence
<220> FEATURE:
<223> OTHER INFORMATION: synthetic DNA

<400> SEQUENCE: 80
tggtttttca acttcttcca 20

<210> SEQ ID NO 81
<211> LENGTH: 20
<212> TYPE: DNA
<213> ORGANISM: Artificial Sequence
<220> FEATURE:
<223> OTHER INFORMATION: synthetic DNA

<400> SEQUENCE: 81
tcatagaatg gatggctcaa 20

<210> SEQ ID NO 82
<211> LENGTH: 20
<212> TYPE: DNA
<213> ORGANISM: Artificial Sequence
<220> FEATURE:
<223> OTHER INFORMATION: synthetic DNA

<400> SEQUENCE: 82
agctactatt gcaccatccc 20

<210> SEQ ID NO 83
<211> LENGTH: 22
<212> TYPE: DNA
<213> ORGANISM: Artificial Sequence
<220> FEATURE:
<223> OTHER INFORMATION: synthetic DNA

<400> SEQUENCE: 83
caataagggc ataccaaaaa tc 22

<210> SEQ ID NO 84
<211> LENGTH: 22
<212> TYPE: DNA
<213> ORGANISM: Artificial Sequence
<220> FEATURE:
<223> OTHER INFORMATION: synthetic DNA

<400> SEQUENCE: 84
ccttaacatt tgtggcatta tc 22

<210> SEQ ID NO 85
<211> LENGTH: 22
<212> TYPE: DNA
<213> ORGANISM: Artificial Sequence
<220> FEATURE:
<223> OTHER INFORMATION: synthetic DNA

<400> SEQUENCE: 85
ttgggaagat gaagttttta ga 22

<210> SEQ ID NO 86
<211> LENGTH: 22
<212> TYPE: DNA
<213> ORGANISM: Artificial Sequence
<220> FEATURE:
<223> OTHER INFORMATION: synthetic DNA

<400> SEQUENCE: 86
cctttactcc aataatttgg ct 22

<210> SEQ ID NO 87
<211> LENGTH: 20
<212> TYPE: DNA

<213> ORGANISM: Artificial Sequence
<220> FEATURE:
<223> OTHER INFORMATION: synthetic DNA

<400> SEQUENCE: 87
tttcatctat tcaggatggg 20

<210> SEQ ID NO 88
<211> LENGTH: 20
<212> TYPE: DNA
<213> ORGANISM: Artificial Sequence
<220> FEATURE:
<223> OTHER INFORMATION: synthetic DNA

<400> SEQUENCE: 88
ggagcaacat tctttgtgac 20

<210> SEQ ID NO 89
<211> LENGTH: 20
<212> TYPE: DNA
<213> ORGANISM: Artificial Sequence
<220> FEATURE:
<223> OTHER INFORMATION: synthetic DNA

<400> SEQUENCE: 89
tgtgcctgaa gaaggtattg 20

<210> SEQ ID NO 90
<211> LENGTH: 20
<212> TYPE: DNA
<213> ORGANISM: Artificial Sequence
<220> FEATURE:
<223> OTHER INFORMATION: synthetic DNA

<400> SEQUENCE: 90
cgtgttactt caccaccact 20

<210> SEQ ID NO 91
<211> LENGTH: 23
<212> TYPE: DNA
<213> ORGANISM: Staphylococcus aureus

<400> SEQUENCE: 91
tatcttatcg ttgagaaggg att 23

<210> SEQ ID NO 92
<211> LENGTH: 22
<212> TYPE: DNA
<213> ORGANISM: Staphylococcus aureus

<400> SEQUENCE: 92
ctacacttgg cttaggatga aa 22

<210> SEQ ID NO 93
<211> LENGTH: 24
<212> TYPE: DNA
<213> ORGANISM: Escherichia coli

<400> SEQUENCE: 93
ctatctgatt gttgaagaag gatt 24

<210> SEQ ID NO 94
<211> LENGTH: 24
<212> TYPE: DNA
<213> ORGANISM: Escherichia coli

```
<400> SEQUENCE: 94

gtttactctt ggtttaggat gaaa                                              24

<210> SEQ ID NO 95
<211> LENGTH: 22
<212> TYPE: DNA
<213> ORGANISM: Staphylococcus aureus

<400> SEQUENCE: 95

cttgttgatc acgataattt cc                                                22

<210> SEQ ID NO 96
<211> LENGTH: 22
<212> TYPE: DNA
<213> ORGANISM: Staphylococcus aureus

<400> SEQUENCE: 96

atcttttagc aaacccgtat tc                                                22

<210> SEQ ID NO 97
<211> LENGTH: 27
<212> TYPE: DNA
<213> ORGANISM: Artificial Sequence
<220> FEATURE:
<223> OTHER INFORMATION: synthetic DNA

<400> SEQUENCE: 97

aacaggtgaa ttattagcac ttgtaag                                           27

<210> SEQ ID NO 98
<211> LENGTH: 27
<212> TYPE: DNA
<213> ORGANISM: Artificial Sequence
<220> FEATURE:
<223> OTHER INFORMATION: synthetic DNA

<400> SEQUENCE: 98

attgctgtta atattttttg agttgaa                                           27

<210> SEQ ID NO 99
<211> LENGTH: 19
<212> TYPE: DNA
<213> ORGANISM: Artificial Sequence
<220> FEATURE:
<223> OTHER INFORMATION: synthetic DNA

<400> SEQUENCE: 99

gtgatcgaaa tccagatcc                                                    19

<210> SEQ ID NO 100
<211> LENGTH: 19
<212> TYPE: DNA
<213> ORGANISM: Artificial Sequence
<220> FEATURE:
<223> OTHER INFORMATION: synthetic DNA

<400> SEQUENCE: 100

atcctcggtt ttctggaag                                                    19

<210> SEQ ID NO 101
<211> LENGTH: 19
<212> TYPE: DNA
<213> ORGANISM: Artificial Sequence
<220> FEATURE:
<223> OTHER INFORMATION: synthetic DNA
```

<400> SEQUENCE: 101
ctggtcatac atgtgatgg 19

<210> SEQ ID NO 102
<211> LENGTH: 19
<212> TYPE: DNA
<213> ORGANISM: Artificial Sequence
<220> FEATURE:
<223> OTHER INFORMATION: synthetic DNA

<400> SEQUENCE: 102
gatgttaccc gagagcttg 19

<210> SEQ ID NO 103
<211> LENGTH: 20
<212> TYPE: DNA
<213> ORGANISM: Artificial Sequence
<220> FEATURE:
<223> OTHER INFORMATION: synthetic DNA

<400> SEQUENCE: 103
ttaagcgtgc ataataagcc 20

<210> SEQ ID NO 104
<211> LENGTH: 20
<212> TYPE: DNA
<213> ORGANISM: Artificial Sequence
<220> FEATURE:
<223> OTHER INFORMATION: synthetic DNA

<400> SEQUENCE: 104
ttgcgattac ttcgccaact 20

<210> SEQ ID NO 105
<211> LENGTH: 20
<212> TYPE: DNA
<213> ORGANISM: Artificial Sequence
<220> FEATURE:
<223> OTHER INFORMATION: synthetic DNA

<400> SEQUENCE: 105
tttactaagc ttgccccttc 20

<210> SEQ ID NO 106
<211> LENGTH: 20
<212> TYPE: DNA
<213> ORGANISM: Artificial Sequence
<220> FEATURE:
<223> OTHER INFORMATION: synthetic DNA

<400> SEQUENCE: 106
aaaaggcagc aattatgagc 20

<210> SEQ ID NO 107
<211> LENGTH: 29
<212> TYPE: DNA
<213> ORGANISM: Artificial Sequence
<220> FEATURE:
<223> OTHER INFORMATION: synthetic DNA
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:

<221> NAME/KEY: modified_base
<222> LOCATION: (15)
<223> OTHER INFORMATION: i
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (21)
<223> OTHER INFORMATION: i

<400> SEQUENCE: 107
aayatgatna cnggngcngc ncaratgga 29

<210> SEQ ID NO 108
<211> LENGTH: 23
<212> TYPE: DNA
<213> ORGANISM: Artificial Sequence
<220> FEATURE:
<223> OTHER INFORMATION: synthetic DNA
<220> FEATURE:
<221> NAME/KEY: modified_base
<222> LOCATION: (3)
<223> OTHER INFORMATION: i
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i

<400> SEQUENCE: 108
ccnacngtnc knccrccytc rcg 23

<210> SEQ ID NO 109
<211> LENGTH: 29
<212> TYPE: DNA
<213> ORGANISM: Artificial Sequence
<220> FEATURE:
<223> OTHER INFORMATION: synthetic DNA
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (18)
<223> OTHER INFORMATION: i

<400> SEQUENCE: 109
carytnathg tngcngtnaa yaaratgga 29

<210> SEQ ID NO 110
<211> LENGTH: 831
<212> TYPE: DNA
<213> ORGANISM: Escherichia coli

<400> SEQUENCE: 110

-continued

```
atgaaaaaca caatacatat caacttcgct attttttttaa taattgcaaa tattatctac     60

agcagcgcca gtgcatcaac agatatctct actgttgcat ctccattatt tgaaggaact    120

gaaggttgtt ttttacttta cgatgcatcc acaaacgctg aaattgctca attcaataaa    180

gcaaagtgtg caacgcaaat ggcaccagat tcaactttca agatcgcatt atcacttatg    240

gcatttgatg cggaaataat agatcagaaa accatattca aatgggataa aacccccaaa    300

ggaatggaga tctggaacag caatcataca ccaaagacgt ggatgcaatt ttctgttgtt    360

tgggtttcgc aagaaataac ccaaaaaatt agattaaata aaatcaagaa ttatctcaaa    420

gattttgatt atggaaatca agacttctct ggagataaag aaagaaacaa cggattaaca    480

gaagcatggc tcgaaagtag cttaaaaatt tcaccagaag aacaaattca attcctgcgt    540

aaaattatta atcacaatct cccagttaaa aactcagcca tagaaaacac catagagaac    600

atgtatctac aagatctgga taatagtaca aaactgtatg ggaaaactgg tgcaggattc    660

acagcaaata gaaccttaca aaacggatgg tttgaagggt ttattataag caaatcagga    720

cataaatatg tttttgtgtc cgcacttaca ggaaacttgg ggtcgaattt aacatcaagc    780

ataaaagcca agaaaaatgc gatcaccatt ctaaacacac taaatttata a             831
```

<210> SEQ ID NO 111
<211> LENGTH: 846
<212> TYPE: DNA
<213> ORGANISM: Enterococcus faecalis

<400> SEQUENCE: 111

```
ttgaaaaagt taatattttt aattgtaatt gctttagttt taagtgcatg taattcaaac     60

agttcacatg ccaaagagtt aaatgattta gaaaaaaaat ataatgctca tattggtgtt    120

tatgctttag atactaaaag tggtaaggaa gtaaaattta attcagataa gagatttgcc    180

tatgcttcaa cttcaaaagc gataaatagt gctattttgt tagaacaagt accttataat    240

aagttaaata aaaaagtaca tattaacaaa gatgatatag ttgcttattc tcctatttta    300

gaaaaatatg taggaaaaga tatcacttta aaagcactta ttgaggcttc aatgacatat    360

agtgataata cagcaaacaa taaaattata aaagaaatcg gtggaatcaa aaaagttaaa    420

caacgtctaa aagaactagg agataaagta acaaatccag ttagatatga gatagaatta    480

aattactatt caccaaagag caaaaaagat acttcaacac ctgctgcttt cggtaagact    540

ttaaataaac ttatcgcaaa tggaaaatta agcaaagaaa acaaaaaatt cttacttgat    600

ttaatgttaa ataataaaag cggagatact ttaattaaag acggtgttcc aaaagactat    660

aaggttgctg ataaaagtgg tcaagcaata acatatgctt ctagaaatga tgttgctttt    720

gtttatccta agggccaatc tgaacctatt gttttagtca tttttacgaa taaagacaat    780

aaaagtgata agccaaatga taagttgata agtgaaaccg ccaagagtgt aatgaaggaa    840

ttttaa                                                              846
```

<210> SEQ ID NO 112
<211> LENGTH: 555
<212> TYPE: DNA
<213> ORGANISM: Pseudomonas aeruginosa

<400> SEQUENCE: 112

```
atgtccgcga gcaccccccc cataactctt cgcctcatga ccgagcgcga cctgccgatg     60

ctccatgact ggctcaaccg gccgcacatc gttgagtggt ggggtggcga cgaagagcga    120

ccgactcttg atgaagtgct ggaacactac ctgcccagag cgatggcgga agagtccgta    180
```

```
acaccgtaca tcgcaatgct gggcgaggaa ccgatcggct atgctcagtc gtacgtcgcg    240

ctcggaagcg gtgatggctg gtgggaagat gaaactgatc caggagtgcg aggaatagac    300

cagtctctgg ctgacccgac acagttgaac aaaggcctag gaacaaggct tgtccgcgct    360

ctcgttgaac tactgttctc ggaccccacc gtgacgaaga ttcagaccga cccgactccg    420

aacaaccatc gagccatacg ctgctatgag aaggcaggat tcgtgcggga gaagatcatc    480

accacgcctg acgggccggc ggtttacatg gttcaaacac gacaagcctt cgagagaaag    540

cgcggtgttg cctaa                                                     555
```

<210> SEQ ID NO 113
<211> LENGTH: 732
<212> TYPE: DNA
<213> ORGANISM: Staphylococcus aureus

<400> SEQUENCE: 113

```
atgaaccaga aaaaccctaa agacacgcaa aattttatta cttctaaaaa gcatgtaaaa     60

gaaatattga atcacacgaa tatcagtaaa caagacaacg taatagaaat cggatcagga    120

aaaggacatt ttaccaaaga gctagtcaaa atgagtcgat cagttactgc tatagaaatt    180

gatggaggct tatgtcaagt gactaaagaa gcggtaaacc cctctgagaa tataaaagtg    240

attcaaacgg atattctaaa attttccttc ccaaaacata taaactataa gatatatggt    300

aatattcctt ataacatcag tacggatatt gtcaaaagaa ttacctttga aagtcaggct    360

aaatatagct atcttatcgt tgagaaggga tttgcgaaaa gattgcaaaa tctgcaacga    420

gctttgggtt tactattaat ggtggagatg gatataaaaa tgctcaaaaa agtaccacca    480

ctatattttc atcctaagcc aagtgtagac tctgtattga ttgttcttga acgacatcaa    540

ccattgattt caaagaagga ctacaaaaag tatcgatctt ttgtttataa gtgggtaaac    600

cgtgaatatc gtgttctttt cactaaaaac caattccgac aggctttgaa gcatgcaaat    660

gtcactaata ttaataaact atcgaaggaa caatttcttt ctattttcaa tagttacaaa    720

ttgtttcact aa                                                        732
```

<210> SEQ ID NO 114
<211> LENGTH: 738
<212> TYPE: DNA
<213> ORGANISM: Escherichia coli

<400> SEQUENCE: 114

```
atgaacaaaa atataaaata ttctcaaaac tttttaacga gtgaaaaagt actcaaccaa     60

ataataaaac aattgaattt aaaagaaacc gataccgttt acgaaattgg aacaggtaaa    120

gggcatttaa cgacgaaact ggctaaaata agtaaacagg taacgtctat tgaattagac    180

agtcatctat tcaacttatc gtcagaaaaa ttaaaatcga atactcgtgt cactttaatt    240

caccaagata ttctacagtt tcaattccct aacaaacaga ggtataaaat tgttgggaat    300

attccttacc atttaagcac acaaattatt aaaaaagtgg tttttgaaag ccatgcgtct    360

gacatctatc tgattgttga agaaggattc tacaagcgta ccttggatat tcaccgaaca    420

ctagggttgc tcttgcacac tcaagtctcg attcagcaat tgcttaagct gccagcggaa    480

tgctttcatc ctaaaccaag agtaaacagt gtcttaataa aacttacccg ccataccaca    540

gatgttccag ataaatattg gaagctatat acgtactttg tttcaaaatg ggtcaatcga    600

gaatatcgtc aactgtttac taaaaatcag tttcatcaag caatgaaaca cgccaaagta    660

aacaatttaa gtaccgttac ttatgagcaa gtattgtcta tttttaatag ttatctatta    720
```

-continued tttaacggga ggaaataa 738

<210> SEQ ID NO 115
<211> LENGTH: 735
<212> TYPE: DNA
<213> ORGANISM: Staphylococcus aureus

<400> SEQUENCE: 115
atgaacgaga aaaatataaa acacagtcaa aactttatta cttcaaaaca taatatagat 60
aaaataatga caaatataag attaaatgaa catgataata tctttgaaat cggctcagga 120
aaagggcatt ttacccttga attagtacag aggtgtaatt tcgtaactgc cattgaaata 180
gaccataaat tatgcaaaac tacagaaaat aaacttgttg atcacgataa tttccaagtt 240
ttaaacaagg atatattgca gtttaaattt cctaaaaacc aatcctataa aatatttggt 300
aatatacctt ataacataag tacggatata atacgcaaaa ttgtttttga tagtatagct 360
gatgagattt atttaatcgt ggaatacggg tttgctaaaa gattattaaa tacaaaacgc 420
tcattggcat tatttttaat ggcagaagtt gatatttcta tattaagtat ggttccaaga 480
gaatattttc atcctaaacc tagagtgaat agctcactta tcagattaaa tagaaaaaaa 540
tcaagaatat cacacaaaga taaacagaag tataattatt tcgttatgaa atgggttaac 600
aaagaataca agaaaatatt tacaaaaaat caatttaaca attccttaaa acatgcagga 660
attgacgatt taaacaatat tagctttgaa caattcttat ctcttttcaa tagctataaa 720
ttatttaata agtaa 735

<210> SEQ ID NO 116
<211> LENGTH: 1029
<212> TYPE: DNA
<213> ORGANISM: Enterococcus faecalis

<400> SEQUENCE: 116
atgaataaaa taaaagtcgc aattatcttc ggcggttgct cggaggaaca tgatgtgtcg 60
gtaaaatccg caatagaaat tgctgcgaac attaatactg aaaaattcga tccgcactac 120
atcggaatta caaaaaacgg cgtatggaag ctatgcaaga agccatgtac ggaatgggaa 180
gccgatagtc tccccgccat attctccccg gataggaaaa cgcatggtct gcttgtcatg 240
aaagaaagag aatacgaaac tcggcgtatt gacgtggctt tcccggtttt gcatggcaaa 300
tgcggggagg atggtgcgat acagggtctg tttgaattgt ctggtatccc ctatgtaggc 360
tgcgatattc aaagctccgc agcttgcatg gacaaatcac tggcctacat tcttacaaaa 420
aatgcgggca tcgccgtccc cgaatttcaa atgattgaaa aaggtgacaa accggaggcg 480
aggacgctta cctaccctgt ctttgtgaag ccggcacggt caggttcgtc ctttggcgta 540
accaaagtaa acagtacgga agaactaaac gctgcgatag aagcagcagg acaatatgat 600
ggaaaaatct taattgagca agcgatttcg ggctgtgagg tcggctgcgc ggtcatggga 660
aacgaggatg atttgattgt cggcgaagtg gatcaaatcc ggttgagcca cggtatcttc 720
cgcatccatc aggaaaacga gccggaaaaa ggctcagaga atgcgatgat tatcgttcca 780
gcagacattc cggtcgagga acgaaatcgg gtgcaagaaa cggcaaagaa agtatatcgg 840
gtgcttggat gcagagggct tgctcgtgtt gatctttttt tgcaggagga tggcggcatc 900
gttctaaacg aggtcaatac cctgcccggt tttacatcgt acagccgcta tccacgcatg 960
gcggctgccg caggaatcac gcttcccgca ctaattgaca gcctgattac attggcgata 1020
gagaggtga 1029

<210> SEQ ID NO 117
<211> LENGTH: 1031
<212> TYPE: DNA
<213> ORGANISM: Enterococcus gallinarum

<400> SEQUENCE: 117
atgaaaaaaa ttgccgtttt atttggaggg aattctccag aatactcagt gtcactaacc 60
tcagcagcaa gtgtgatcca agctattgac ccgctgaaat atgaagtaat gaccattggc 120
atcgcaccaa caatggattg gtattggtat caaggaaacc tcgcgaatgt tcgcaatgat 180
acttggctag aagatcacaa aaactgtcac cagctgactt tttctagcca aggatttata 240
ttaggagaaa aacgaatcgt ccctgatgtc ctctttccag tcttgcatgg gaagtatggc 300
gaggatggct gtatccaagg actgcttgaa ctaatgaacc tgccttatgt tggttgccat 360
gtcgctgcct ccgcattatg tatgaacaaa tggctcttgc atcaacttgc tgataccatg 420
ggaatcgcta gtgctcccac tttgctttta tcccgctatg aaaacgatcc tgccacaatc 480
gatcgtttta ttcaagacca tggattcccg atctttatca agccgaatga agccggttct 540
tcaaaaggga tcacaaaagt aactgacaaa acagcgctcc aatctgcatt aacgactgct 600
tttgcttacg gttctactgt gttgatccaa aaggcgatag cgggtattga aattggctgc 660
ggcatcttag gaaatgagca attgacgatt ggtgcttgtg atgcgatttc tcttgtcgac 720 ggttttttg attttgaaga gaaataccaa ttaatcagcg ccacgatcac tgtcccagca 780
ccattgcctc tcgcgcttga atcacagatc aaggagcagg cacagctgct ttatcgaaac 840
ttgggattga cgggtctggc tcgaatcgat tttttcgtca ccaatcaagg agcgatttat 900
ttaaacgaaa tcaacaccat gccgggattt actgggcact cccgctaccc agctatgatg 960
gcggaagtcg ggttatccta cgaaatatta gtagagcaat tgattgcact ggcagaggag 1020
gacaaacgat g 1031

<210> SEQ ID NO 118
<211> LENGTH: 809
<212> TYPE: DNA
<213> ORGANISM: Abiotrophia adiacens

<400> SEQUENCE: 118
tggtgctatc ttagtagtat ctgcagctga tggtccaatg cctcaaacac gtgaacacat 60
cttattatca cgtcaagtag gtgttcctta catcgttgta ttcttaaaca aagttgacat 120
ggttgacgat gaagaattat tagaattagt agaaatggaa gttcgtgact tattatcaga 180
atacgatttc ccaggcgatg acactccagt tgttgcaggt tctgctttac gcgctttaga 240
aggcgacgct tcatacraag aaaaaatctt agaattaatg gctgctgttg acgaatacat 300
tccaactcca gaacgygacg ttgacaaacc attcatgatg ccagttgaag acgtgttctc 360
aatcacaggt cgtggtactg ttgctacagg tcgtgttgaa cgtggacaag ttcgtgttgg 420
tgacgaagtt gaaatcgttg gtatttcaga agaaacttca aaaacaactg taactggtgt 480
tgaaatgttc cgtaaattgt tagactacgc tgaagcaggg gataacattg gtacattatt 540
acgtggtgtt acacgtgaca acatcgaacg tggacaagtt cttgctaaac caggaacaat 600
cactccacat actaaattca aagctgaagt ttacgtatta actaaagaag aaggtggacg 660
tcatactcca ttcttctcta actaccgtcc tcaattctac ttccgtacaa cagacatcac 720
tggtgtttgt gtgttaccag aaggcgttga aatggtaatg cctggtgata acgtaactat 780
ggaagttgaa ttaattcacc cagtagcga 809

<210> SEQ ID NO 119
<211> LENGTH: 817
<212> TYPE: DNA
<213> ORGANISM: Abiotrophia defectiva

<400> SEQUENCE: 119
cggcgcgatc ctcgttgtat ctgctgctga cggcccaatg ccacaaactc gtgaacacat 60
cctcttgtct cgtcaagttg gtgttcctta catcgtagta ttcttgaaca aagttgacat 120
ggttgacgac gaagaattgc tcgaattagt tgaaatggaa gttcgtgacc tcttgtctga 180
atacgacttc ccaggcgacg acactccagt tatcgctggt tcagctttga aagctttaga 240
aggcgacgct aactacgaag ctaaagtttt agaattgatg gaacaagttg atgcttacat 300
tccagaacca gaacgtgaca ctgacaagcc attcatgatg ccagtcgaag acgtattctc 360
tatcactggt cgtggtactg ttgcaactgg tcgtgttgaa cgtggtcaag ttcgcgttgg 420
tgacgaagtt gaaatcgttg gtatcgaaga agaaacttct aagactaccg ttaccggtgt 480
tgaaatgttc cgtaagttat tggattacgc tgaagctggg gacaacgttg gtaccttgtt 540
acgtggtgta actcgtgacc aaatccaacg tggtcaagta ttatctaaac caggttcaat 600
cactccgyac actaagttcg aagctgaagt gtacgtattg tctaaagaag aaggtggtcg 660
tcacactcca ttcttctcta actaccgtcc acaattctac ttccgtacaa ctgacgtaac 720
tggtgttgtt actttaccag aaggtactga aatggttatg ccaggcgaca acgtacaaat 780
ggttgttgaa ttgatccacc caatcgcgat cgaagaa 817

<210> SEQ ID NO 120
<211> LENGTH: 754
<212> TYPE: DNA
<213> ORGANISM: Candida albicans

<400> SEQUENCE: 120
ctctgtcaaa tgggacaaaa acagatttga agaaatcatc aaggaaacct ccaacttcgt 60
caagaaggtt ggttacaacc caaagactgt tccattcgtt ccaatctctg gttggaatgg 120
tgacaacwtg attgaascat ccaccaactg tccatggtac aagggttggg aaaaggaaac 180
caaatccggt aaagttactg gtaagacctt gttagaagct attgacgcta ttgaaccacc 240
aaccagacca accgacaaac cattgagatt gccattrcaa gatgtttaca agatcggtgg 300
tattggtact gtgccagtcg gtagagttga aactggtatc atcaaagccg gtatggtwgt 360
tactttcgcc ccagctggtg ttaccactga agtcaartcc gttgaaatgc atcacgaaca 420
attggctgaa ggtgttccag gtgacaatgt trgtttcaac gttaagaacr tttccgttaa 480
agaaattaga agaggtaacg tttgtggtga ctccaagaac gatccaccaa agggttgtga 540
ctctttcaat gcccaagtca ttgttttgaa ccatccaggt caaatctctg ctggttactc 600
tccagtcttg gattgtcacr ctgcccacat tgcttgtaaa ttcgacrctt tggttgaaaa 660
gattgacaga agaactggta agraattgga agaaaatcca aaattcgtca aatccggtga 720
tgctgctatc gtcaagatgg tcccaaccaa acca 754

<210> SEQ ID NO 121
<211> LENGTH: 753
<212> TYPE: DNA
<213> ORGANISM: Candida glabrata

<400> SEQUENCE: 121
tctgtcaagt gggatgaatc cagattcgct gaaatcgtta aggaaacctc caacttcatc 60

-continued

```
aagaaggtcg gttacaaccc aaagactgtt ccattcgtcc caatctctgg ttggaacggt    120

gacaacatga ttgaagccac caccaacgct tcctggtaca agggttggga aaaggaaacc    180

aaggctggtg tcgtcaaggg taagaccttg ttggaagcca ttgacgctat cgaaccacca    240

accagaccaa ctgacaagcc attgagattg ccattgcaag atgtctacaa gatcggtggt    300

atcggtacgg tgccagtcgg tagagtcgaa accggtgtca tcaagccagg tatggttgtt    360

accttcgccc cagctggtgt taccactgaa gtcaagtccg ttgaaatgca ccacgaacaa    420

ttgactgaag gtttgccagg tgacaacgtt ggtttcaacg ttaagaacgt ttccgttaag    480

gaaatcagaa gaggtaatgt ctgtggtgac tccaagaacg acccaccaaa ggctgctgct    540

tctttcaacg ctaccgtcat tgtcttgaac cacccaggtc aaatctctgc tggttactct    600

ccagttttgg actgtcacac cgcccacatt gcttgtaagt tcgaagaatt gttggaaaag    660

aacgacagaa gatccggtaa gaagttggaa gactctccaa agttcttgaa gtccggtgac    720

gctgctttgg ttaagttcgt tccatccaag cca                                 753
```

<210> SEQ ID NO 122
<211> LENGTH: 752
<212> TYPE: DNA
<213> ORGANISM: Candida kruisii

<400> SEQUENCE: 122

```
ccgttaagtg ggatgaaaac agatttgaag aaattgtcaa ggaaacccaa aacttcatca     60

agaaggttgg ttacaaccca aagactgttc cattcgttcc aatctctggt tggaatggtg    120

acaacatgat tgaagcatcc accaactgtc catggtacaa gggttggact aaggaaacca    180

aggcaggtgt tgttaagggt aagaccttat tagaagcaat cgatgctatt gaaccacctg    240

tcagaccaac cgaaaagcca ttaagattac cattacaaga tgtttacaag attggtggta    300

ttggtactgt gccagtcggt agagtcgaaa ccggtgtcat taagccaggt atggttgtca    360

cttttgctcc agcaggtgtc accaccgaag tcaaatccgt tgaaatgcac catgaacaat    420

tagaacaagg tgttccaggt gataacgttg gtttcaacgt taagaacgty tctgtcaagg    480

atatcaagag aggtaacgtt tgtggtgact ccaagaacga cccaccaatg ggtgcagctt    540

ctttcaatgc tcaagtcatt gtcttgaacc accctggtca aatttccgct ggttactctc    600

cagtcttgga ttgtcacact gcccacattg catgtaagtt cgacgaatta atcgaaaaga    660

ttgacagaag aactggtaag tctgttgaag accatccaaa gtcygtcaag tctggtgatg    720

cagctatcgt caagatggtc ccaaccaagc ca                                  752
```

<210> SEQ ID NO 123
<211> LENGTH: 754
<212> TYPE: DNA
<213> ORGANISM: Candida parapsilosis

<400> SEQUENCE: 123

```
ctcagtcaaa tgggacaaga rcagatacga agaaattgtc aaggaaactt ccaacttcgt     60

caagaaggtt ggttacaacc ctaaagctgt cccattcgtc ccaatctctg gttggaacgg    120

tgacaatatg attgaaccat caaccaactg tccatggtac aagggttggg aaaaggaaac    180

taaagctggt aaggttaccg gtaagacctt gttggaagct atcgatgcta tcgarccacc    240

aaccagacca actgacaagc cattgagatt gccattgcaa gatgtctaca agattggtgg    300

tattggaact gtgccagttg gtagagttga aaccggtatc atcaaggctg gtatggttgt    360

tacttttgcc ccagctggtg ttaccactga agtcaagtcc gttgaaatgc accacgaaca    420
```

-continued attgactgaa ggtgtcccag gtgacaatgt tggtttcaac gtcaagaacg tttcagttaa 480
ggaaatcaga agaggtaacg tytgtggtga ctccaagaac gatccaccaa agggatgtga 540
ytccttcaat gctcaagtta ttgtcttgaa ccacccaggt caaatctctg ctggttactc 600
accagtcttg gattgtcaca ctgcccacat tgcttgtaaa ttcgacactt tgattgaaaa 660
gattgacaga agaaccggta agaaattgga agwtgaacca aaattcatca agtccggtga 720
tgctgcyatc gtcaagatgg tcccaaccaa gcca 754

<210> SEQ ID NO 124
<211> LENGTH: 753
<212> TYPE: DNA
<213> ORGANISM: Candida tropicalis

<400> SEQUENCE: 124
tctgttaaat gggacaaraa cagatttgaa gaaattatca aggaaacytc taacttcgtc 60
aagaaggttg gttacaaccc taaggctgtt ccattcgttc caatctcwgg ttggaatggt 120
gacaacatga ttgaagcttc taccaactgt ccatggtaca agggttggga aaaagaaacc 180
aaggctggta aggttaccgg taagactttg ttggaagcca ttgatgctat tgaaccacct 240
tcaagaccaa ctgacaagcc attgagattg ccattgcaag atgtttacaa gattggtggt 300
attggtactg tgccagtcgg tagagttgaa actggtgtca tcaaagccgg tatggttgtt 360
actttygccc cagctggtgt taccactgaa gtcaaatccg tygaaatgca ccacgaacaa 420
ttggctgaag gtgtcccagg tgacaatgtt ggtttcaacg ttaagaacgt ttctgttaaa 480
gaaattagaa gaggtaacgt ttgtggtgac tccaagaacg atccaccaaa gggttgtgac 540
tctttcaacg ctcaagttat tgtcttgaac cacccaggtc aaatytctgc tggttactct 600
ccagtcttgg attgtcacac tgctcatatt gcttgtaaat tcgacacctt ggttgaaaag 660
attgacagaa gaactggtaa gaaattggaa gaaaatccaa aattcgtcaa atccggtgat 720
gctgctattg tcaagatggt tccaaccaaa cca 753

<210> SEQ ID NO 125
<211> LENGTH: 814
<212> TYPE: DNA
<213> ORGANISM: Corynebacterium accolens

<400> SEQUENCE: 125
cggcgctatc ctggttgttg ctgcaaccga tggcccgatg ccgcagaccc gcgagcacgt 60
tctgcttgct cgccaggttg gcgttcctta catcctcgtt gcactgaaca agtgcgacat 120
ggttgatgat gaggaaatca tcgagctcgt ggagatggag atctccgagc tgctcgcaga 180
gcaggactac gatgaggaag ctcctatcgt tcacatctcc gctctgaagg cactcgaggg 240
tgacgagaag tgggtacagt ccatcgttga cctgatggat gcctgcgaca actccatccc 300
tgatccggag cgcgctaccg atcagccgtt cttgatgcct atcgaggaca tcttcaccat 360
taccggccgc ggtaccgttg ttaccggccg tgttgagcgt ggtcgtctga acgtcaacga 420
ggacgttgag atcatcggta tccaggagaa gtcccagaac accaccgtta ccggtatcga 480
gatgttccgc aagatgatgg actacaccga ggctggcgac aactgtggtc tgcttctgcg 540
tggtaccaag cgtgaggacg ttgagcgtgg ccaggttgtt atcaagccgg gcgcttacac 600
ccctcacacc aagttcgagg gttccgtcta cgtcctgaag aaggaagagg gcggccgcca 660
caccccgytc atgaacaact accgtcctca gttctacttc cgcaccaccg acgttaccgg 720
tgttgtgaac ctgcctgagg gcaccgagat ggttatgcct ggcgacaacg ttgagatgtc 780
tgttgagctc atccagcctg ttgctatgga cgag 814

<210> SEQ ID NO 126
<211> LENGTH: 814
<212> TYPE: DNA
<213> ORGANISM: Corynebacterium diphtheriae

<400> SEQUENCE: 126
cggcgcaatc ctcgttgttg ctgccaccga cggcccaatg cctcagaccc gtgagcacgt 60
tctgctcgct cgccaggtcg gcgttcctta catcctcgtt gctctgaaca agtgcgacat 120
ggttgatgat gaggaaatca tcgagctcgt cgagatggag atccrtgagc tgctcgctga 180
gcaggattac gacgaagagg ctccaatcat ccacatctcc gcactgaagg ctcttgaggg 240
cgacgagaag tggacccagt ccatcatcga cctcatgcag gcttgckatg attccatccc 300
agacccagag cgtgagaccg acaagccatt cctcatgcct atcgaggaca tcttcaccat 360
caccggccgc ggtaccgttg ttaccggccg tgttgagcgt ggctccctga aggtcaacga 420
ggacgtcgag atcatcggta tccgcgagaa kgctaccacc accaccgtta ccggtatcga 480
gatgttccgt aagcttctcg actacaccga ggctggcgac aactgtggtc tgcttctccg 540
tggcgttaag cgcgaagacg ttgagcgtgg ccaggttgtt gttaagccag gcgcttacac 600
ccctcacacc gagttcgagg gctctgtcta cgttctgtcc aaggacgagg gtggccgcca 660
caccccattc ttcgacaact accgcccaca gttctacttc cgcaccaccg acgttaccgg 720
tgttgtgaag cttcctgagg gcaccgagat ggtcatgcct ggcgacaacg tcgacatgtc 780
cgtcaccctg atccagcctg tcgctatgga tgag 814

<210> SEQ ID NO 127
<211> LENGTH: 814
<212> TYPE: DNA
<213> ORGANISM: Corynebacterium genitalium

<400> SEQUENCE: 127
cggcgccatc ctggttgttg ctgcaaccga tggcccgatg ccgcagaccc gtgagcacgt 60
tctgctggct cgccaggttg gcgttccgta catcctagtt gcactgaaca agtgcgacat 120
ggttgatgat gaggagctgc tggagctcgt cgagatggag gtccgcgagc tgctggctga 180
gcaggacttc gacgaggaag cacctgttgt tcacatctcc gcactgaagg ccctggaggg 240
cgacgagaag tgggctaagc agatcctgga gctcatggag gcttgcgaca actccatccc 300
ggatccggag cgcgagaccg acaagccgtt cctgatgccg gttgrggaca tcttcaccat 360
taccggccgc ggtaccgttg ttaccggccg tgttgagcgt ggcgtcctga acctgaacga 420
cgaggtcgag atcctgggca tccgcgagaa gtccaccaag accaccgtta cctccatcga 480
gatgttcaac aagctgctgg acaccgcaga ggctggcgac aacgccgcac tgctgctgcg 540
tggcctgaag cgcgaagatg ttgagcgtgg tcagatcgtt gctaagccgg gcgagtacac 600
cccgcacacc gagttcgagg gctccgtcta cgttctgtcc aaggacgagg gtggccgcca 660
caccccgttc ttcgacaact accgtccgca gttctatttc cgcaccaccg acgttaccgg 720
tgttgtgaag ctgccggagg gcaccgagat ggttatgccg ggcgacaacg ttgacatgtc 780
cgtcaccctg atccagccgg ttgctatgga cgag 814

<210> SEQ ID NO 128
<211> LENGTH: 814
<212> TYPE: DNA
<213> ORGANISM: Corynebacterium jeikeium

<400> SEQUENCE: 128
cggcgccatc ctggttgttg ccgcaaccga tggcccgatg ccgcagaccc gcgagcacgt 60
tctgctggcy cgccaggttg gcgttccgta catcctggtt gcactgaaca agtgtgacat 120
ggttgacgat gaggagctgc tggagctcgt cgagatggag gtccgcgagc tgctggctga 180
gcaggacttc gacgaggaag ctccggttgt tcacatctcc gcactgaagg ccctggaggg 240
cgacgagaag tgggctaacc agattctcga gctgatgcag gcttgcgacg agtctatccc 300
ggatccggag cgcgagaccg acaagccgtt cctgatgccg gttgwggaca tcttcaccat 360
taccggtcgc ggtaccgttg ttaccggccg tgttgagcgt ggcatcctga acctgaacga 420
cgaggttgag atcctgggta tccgcgagaa gtcccagaag accaccgtta cctccatcga 480
gatgttcaac aagctgctgg acaccgcaga ggctggcrac aacgctgcac tgctgctgcg 540
tggtctgaag cgcgaggacg ttgagcgtgg ccagatcatc gctaagccgg gcgagtacac 600
cccgcacacc gagttcgagg gctccgtcta cgttctgtcc aaggacgagg gcggccgcca 660
caccccgttc ttcgacaact accgtccgca gttctacttc cgcaccaccg acgttaccgg 720
tgttgtgaag ctgcctgagg gcaccgagat ggttatgccg ggcgacaacg tygacatgtc 780
cgtcaccctg atccagccgg ttgctatgga cgag 814

<210> SEQ ID NO 129
<211> LENGTH: 748
<212> TYPE: DNA
<213> ORGANISM: Corynebacterium pseudodiphtheriticum

<400> SEQUENCE: 129
cggcgctatc ttggttgttg cagctaccga cggcccaatg ccacagactc gcgagcacgt 60
tctgctggct cgccaggttg gcgttcctta catcctggtt gcactaaaca agtgcgacat 120
ggttgacgac gaggaaatcc tcgagctcgt cgagatggag atccgcgaat tgctggctga 180
ccaggaattc gacgaagaag ctccaatcgt tcacatctcc gcagtcggcg ccttggaagg 240
cgaagagagg tgggttaacg ccatcgttga actgatggat gcttgtgacg agtcgatccc 300
tgatccagac cgtgctaccg acaagccatt cctgatgcct atcgaggaca tcttcaccat 360
taccggtcgt ggcaccgttg ttacgggtcg tgttgagcgt ggttccctga aggtcaacga 420
agaagtcgag atcatcggca tcaaggaaaa gtcccagaag accaccatca ccggtatcga 480
aatgttccgc aagatgctgg actacaccga ggccggcgac aacgctggtc tgctgcttcg 540
cggtaccaag cgtgaagacg ttgagcgtgg acaggttatc gttgctccag gtgcttacag 600
cacccacaag aagttcgaag gttccgtcta cgttctttcc aaggacgagg gcggccgcca 660
caccccgttc ttcgacaact accgtcctca gttctacttc cgcaccaccg acgttaccgg 720
tgttgttacc ctgcctgagg gcaccgag 748

<210> SEQ ID NO 130
<211> LENGTH: 813
<212> TYPE: DNA
<213> ORGANISM: Corynebacterium striatum

<400> SEQUENCE: 130
ggcgctatct tggttgttgc tgcaaccgat ggcccgrtgc cgcagacccg cgagcacgtt 60
cttctggctc gccaggttgg cgttccttac atcctcgttg cactgaacaa gtgcgacatg 120
gttgacgacg aggaaattat cgagctcgtc gagatggaga tccgcgaact gctcgcagag 180
caggactacg atgaggaagc tccgatcgtt cacatctctg ctctgaaggc tcttgagggc 240

-continued

```
grcgagaagt gggtacaggc tatcgttgac ctgatgcagg cttgcgatga ctccatcccg    300

gatccggagc gcgagctgga caagccgttc ctgatgccaa tcgaggacat cttcaccatc    360

accggccgcg gtaccgttgt tactggccgt gttgagcgtg gctccctgaa cgtcaacgag    420

gacgttgaga tcatcggtat ccaggacarg tccatctcca ccaccgttac cggtatcgag    480

atgytccgca agatgatgga ctacaccgag gctggcgaca actgtggtct gcttctgcgt    540

ggtaccaagc gtgaagaggt tgagcgcggc caggttgtta ttaagccggg cgcttacacc    600

cctcacaccc agttcgaggg ttccgtctac gtcctgaaga aggaagaggg cggccgccac    660

accccgttca tggacaacta ccgtccgcag ttctacttcc gcaccaccga cgttaccggc    720

gtcatcaagc tgcctgaggg caccgagatg gttatgcctg gcgacaacgt cgagatgtcy    780

gtcgagctga tccagccggt cgctatggac gag                                 813
```

<210> SEQ ID NO 131
<211> LENGTH: 817
<212> TYPE: DNA
<213> ORGANISM: Enterococcus avium

<400> SEQUENCE: 131

```
cggagctatc ttagtagtat ctgctgctga tggccctatg cctcaaactc gtgaacacat     60

cttgttatct cgtaacgttg gtgttcctta catcgttgta ttcttaaaca aaatggatat    120

ggttgacgat gaagaattac ttgaattagt tgaaatggaa gttcgtgact tattaactga    180

atacgacttc ccaggcgacg acactccagt tatcgcaggt tcagcgttga aagctttaga    240

aggcgacgct tcatacgaag aaaaaatctt agaattaatg gctgctgttg acgaatatat    300

cccaacacca gttcgtgata ctgacaaacc attcatgatg ccagtcgaag acgtattctc    360

aatcactggt cgtggtactg ttgcaactgg tcgtgttgaa cgtggacaag ttcgcgttgg    420

tgacgaagtt gaaatcgtag gtatcgctga cgaaactgct aaaacaactg ttacaggtgt    480

tgaaatgttc cgtaaattgt tagactacgc tgaagcaggt gacaacatcg gtgctttgtt    540

acgtggtgtt gcacgtgaag atatccaacg tggacaagta ttggctaaac cagcttcaat    600

cactccacat acaaaattct ctgcagaagt ttatgttcta actaaagaag aaggtggacg    660

tcatactcca ttcttcacta actaccgtcc tcagttctac ttccgtacaa ctgacgtaac    720

tggtgtagtt gatctaccag aaggtactga aatggtwatg cctggggata acgtaactat    780

ggaagttgaa ttgatycacc caatygcggt agaagac                             817
```

<210> SEQ ID NO 132
<211> LENGTH: 817
<212> TYPE: DNA
<213> ORGANISM: Enterococcus faecalis

<400> SEQUENCE: 132

```
cggagctatc ttagtagttt ctgctgctga tggtcctatg cctcaaacac gtgaacatat     60

cttattatca cgtaacgttg gtgtaccata catcgttgta ttcttaaaca aaatggatat    120

ggttgatgac gaagaattat tagaattagt agaaatggaa gttcgtgact tattatcaga    180

atacgatttc ccaggcgatg atgttccagt tatcgcaggt tctgctttga aagctttaga    240

aggcgacgag tcttatgaag aaaaaatctt agaattaatg gctgcagttg acgaatatat    300

cccaactcca gaacgtgata ctgacaaacc attcatgatg ccagtcgaag acgtattctc    360

aatcactgga cgtggtactg ttgctacagg acgtgttgaa cgtggtgaag ttcgcgttgg    420

tgacgaagtt gaaatcgttg gtattaaaga cgaaacatct aaaacaacyg ttacaggtgt    480
```

```
tgaaatgttc cgtaaattat tagactacgc tgaagcaggc gacaacmtcg gtgctttatt    540

acgtggtgta gcacgtgaag atatcgaacg tggacaagta ttagctaaac cagctacaat    600

cactccacac acaaaattca aagctgaagt atacgtatta tcaaaagaag aaggcggacg    660

tcacactcca ttcttcacta actaccgtcc tcaattctac ttccgtacaa cagacgttac    720

tggtgttgta gaattgccag aaggtactga aatggtaatg cctggtgata acgttgctat    780

ggacgttgaa ttaattcacc caatcgctat cgaagac                             817
```

<210> SEQ ID NO 133
<211> LENGTH: 774
<212> TYPE: DNA
<213> ORGANISM: Enterococcus faecium

<400> SEQUENCE: 133

```
cggagctatc ttggtagttt ctgctgctga cggcccaatg cctcaaactc gtgaacacat     60

cctattgtct cgtcaagttg gtgttcctta catcgttgta ttcttgaaca aagtagacat    120

ggttgatgac gaagaattac tagaattagt tgaaatggaa gttcgtgacc tattaacaga    180

atacraattc cctggtgrcg atgttcctgt agttgctgga tcagctttga aagctctaga    240

aggcgacgct tcatacgaag aaaaaattct tgaattaatg gctgcagttg acgaatacat    300

cccaactcca gaacgtgaca acgacaaacc attcatgatg ccagttgaag acgtgttctc    360

aattactgga cgtggtactg ttgctacagg tcgtgttgaa cgtggacaag ttcgcgttgg    420

tgacgaagtt gaagttgttg gtattgctga agaaacttca aaaacaacag ttactggtgt    480

tgaaatgttc cgtaaattgt tagacyacgc tgaagctgga gacracattg gtgctttact    540

acgtggtgtt gcacgtgaag acatccaacg tggacaagtt ttagctaaac caggtacaat    600

cacacctcrt acaaaattct ctgcagaagt atacgtgttg acaaaagaag aaggtggacg    660

tcatactcca ttcttcacta actaccgtcc acaattctac ttccgtacaa ctgacgtaac    720

aggtgttgtt gaattaccag aaggaactga aatggtcatg cccggtgaca acgt          774
```

<210> SEQ ID NO 134
<211> LENGTH: 809
<212> TYPE: DNA
<213> ORGANISM: Enterococcus gallinarum

<400> SEQUENCE: 134

```
cggtgcgatc ttagtagtat ctgctgctga cggtcctatg cctcaaactc gtgaacacat     60

cttgttatca cgtaacgttg gcgtaccata catcgttgtt ttcttgaaca aaatggatat    120

ggttgaygac gaagaattgc tagaattagt tgaaatggaa gttcgtgacc tattgtctga    180

atatgacttc ccaggcgacg atgttcctgt aatcgccggt tctgctttga aagctcttga    240

aggagatcct tcatacgaag aaaaaatcat ggaattgatg gctgcagttg acgaatacgt    300

tccaactcca gaacgtgata ctgacaaacc attcatgatg ccagtcgaag acgtattctc    360

aatcactgga cgtggtactg ttgctacagg ccgtgttgaa cgtggacaag ttcgcgttgg    420

tgatgaagta gaaatcgttg gtattgctga cgaaactgct aaaacaactg taacaggtgt    480

tgaaatgttc cgtaaattgt tagactatgc tgaagcaggg gataacattg gtgcattgct    540

acgtggggtt gctcgtgaag acatccaacg tggacaagta ttggctaaag ctggtacaat    600

cacacctcat acaaaattca aagctgaagt ttatgttttg acaaaagaag aaggtggacg    660

tcacactcca ttcttcacta actaccgtcc tcagttctac ttccgtacaa ctgacgtaac    720

tggtgttgtt gaattaccag aaggaactga aatggtgatg cctggcgaca acgtgaccat    780
```

cgacgttgaa ttgatrcacc caatcgctc 809

<210> SEQ ID NO 135
<211> LENGTH: 823
<212> TYPE: DNA
<213> ORGANISM: Gardnerella vaginalis

<400> SEQUENCE: 135
tggcgcaatc ctcgtggttg ctgctaccga cggtccaatg gctcagaccc gtgaacacgt 60
cttgcttgct aagcaggtcg gcgttccaaa aattcttgtt gctttgaaca agtgcgatat 120
ggttgacgac gaagagctta tcgatctcgt tgaagaagag gtccgtgacc tcctcgaaga 180
aaacggcttc gatcgcgatt gcccagtcyt ccgtacttcc gcttacggcg ctttgcatga 240
tgacgctcca gaccacgaca agtgggtaga gaccgtcaag gaactcatga aggctgttga 300
cgagtacatc ccaaccccaa ctcacgatct tgacaagcca ttcttgatgc caatcgaaga 360
tgtgttcacc atctccggtc gtggtyccgt tgtcaccggt cgtgttgagc gtggtaagct 420
cccaatcaac accccagttg agatcgttgg tttgcgcgat acccagacca ccaccgtcac 480
ctctatcgag accttccaca agcagatgga tgaggcagag gctggcgata acactggtct 540
tcttctccgc ggtatcaacc gtaccgacgt tgagcgtggt caggttgtgg ctgctccagg 600
ttctgtgact ccacacacca agttcgaagg cgaagtttac gtcttgacca aggacgaagg 660
tggccgtcac tcgccattct tctccaacta ccgtccacag ttctacttcc gtaccaccga 720
tgttactggc gttatcacct tgccagacgg catcgaaatg gttcagccag gcgatcacgc 780
aaccttcact gttgagttga tccaggctat cgcaatggaa gag 823

<210> SEQ ID NO 136
<211> LENGTH: 817
<212> TYPE: DNA
<213> ORGANISM: Listeria innocua

<400> SEQUENCE: 136
cggagctatc ttagtagtat ctgctgctga tggcccaatg ccacaaactc gtgaacatat 60
cttactttca cgtcaagttg gtgttccata catcgttgta ttcatgaaca aatgtgacat 120
ggttgacgat gaagaattac tagaattagt tgaaatggaa attcgtgatc tattaactga 180
atatgaattc cctggcgatg acattcctgt aatcaaaggt tcagctctta aagcacttca 240
aggtgaagct gactgggaag ctaaaattga cgagttaatg gaagctgtag attcttacat 300
tccaactcca gaacgtgata ctgacaaacc attcatgatg ccagttgagg atgtattctc 360
aatcactggt cgtggaacag ttgcaactgg acgtgttgaa cgtggacaag ttaaagttgg 420
tgacgaagta gaagttatcg gtattgaaga agaaagcaaa aaagtagtag taactggagt 480
agaaatgttc cgtaaattac tagactacgc tgaagctggc gacaacattg gcgcacttct 540
acgtggtgtt gctcgtgaag atatccaacg tggtcaagta ttagctaaac caggttcgat 600
tactccacac actaacttca aagctgaaac ttatgtttta actaaagaag aaggtggacg 660
tcacactcca ttcttcaaca actaccgccc acaattctat ttccgtacta ctgacgtaac 720
tggtattgtt acacttccag aaggtactga aatggtaatg cctggtgata acattgagct 780
tgcagttgaa ctaattgcac caatcgctat cgaagac 817

<210> SEQ ID NO 137
<211> LENGTH: 818
<212> TYPE: DNA
<213> ORGANISM: Listeria ivanovii

<400> SEQUENCE: 137
cggagctatc ttagtagtat ctgctgctga tggtccaatg ccacaaactc gtgaacatat 60
tcttactttc acgtcaagtt ggtgttccat acatcgttgt attcatgaac aaatgtgaca 120
tggttgacga tgaagaatta cttgaattag ttgaaatgga aattcgtgat ctattaactg 180
aatatgaatt ccctggcgac gacattcctg taatcaaagg ttcagctctt aaagcacttc 240
aaggtgaagc tgattgggaa gctaaaattg acgagttaat ggaagctgta gattcttaca 300
ttccaactcc agaacgtgat actgacaaac cattcatgat gccagttgag gatgtattct 360
caatcactgg tcgtggaaca gttgcaactg gacgtgttga acgtggacaa gttaaagttg 420
gtgacgaagt agaagttatc ggtattgaag aagaaagcaa aaaagtagta gtaactggag 480
tagaaatgtt ccgtaaatta ctagactacg ctgaagctgg cgacaacatt ggcgcacttc 540
tacgtggtgt tgctcgtgaa gatatccaac gtggtcaagt attagctaaa ccaggttcga 600
ttactccaca tactaacttc aaagctgaaa cttatgtttt aactaaagaa gaaggtggac 660
gtcatactcc attcttcaac aactaccgcc cacaattcta tttccgtact actgacgtaa 720
ctggtattgt tacacttcca gaaggtactg aaatggtaat gcctggtgat aacattgagc 780
ttgcagttga actaattgca ccaatcgcta tcgaagac 818

<210> SEQ ID NO 138
<211> LENGTH: 817
<212> TYPE: DNA
<213> ORGANISM: Listeria monocytogenes

<400> SEQUENCE: 138
cggagctatc ttagtagtat ctgctgctga tggcccaatg ccacaaactc gtgaacatat 60
cttactttca cgtcaagttg gtgttccata catcgttgta ttcatgaaca aatgtgacat 120
ggttgacgat gaagaattac tagaattagt tgaaatggaa attcgtgatc tattaactga 180
atatgaattc cctggcgatg acattcctgt aatcaaaggt tcagctctta aagcacttca 240
aggtgaagct gactgggaag ctaaaattga cgagttaatg gaagctgtag attcttacat 300
tccaactccw gaacgtgata ctgacaaacc attcatgatg ccagttgagg atgtattctc 360
aatcactggt cgtggaacag ttgcaactgg acgtgttgaa cgtggacaag ttaaagttgg 420
tgacgaagta gaagttatcg gtatcgaaga agaaagcaaa aaagtagtag taactggagt 480
agaaatgttc cgtaaattac tagactacgc tgaagctggc gacaacattg gcgcacttct 540
acgtggtgtt gctcgtgaag atatccaacr tggtcaagta ttagctaaac caggttcgat 600
tactccacac actaacttca aagctgaaac ttatgtttta actaaagaag aaggtggacg 660
tcacactcca ttcttcaaca actaccgccc acaattctat ttccgtacta ctgacgtaac 720
tggtattgtt acacttccag aaggtactga aatggtaayg cctggtgata acattgagct 780
tgcagttgaa ctaattgcac caatcgctat cgaagac 817

<210> SEQ ID NO 139
<211> LENGTH: 817
<212> TYPE: DNA
<213> ORGANISM: Listeria seeligeri

<400> SEQUENCE: 139
cggagctatc ttagtagtat ctgctgctga tggcccaatg ccacaaactc gtgaacatat 60
cttactttca cgtcaagttg gtgttccata catcgttgta ttcatgaaca aatgtgacat 120
ggttgacgat gaagaattac ttgaattagt tgaaatggaa attcgtgatc tattaactga 180
atatgaattc cctggtgatg acattcctgt aatcaaaggt tcagctctta aagcacttca 240
aggtgaagct gactgggaag ctaaaattga cgagttaatg gaagctgtag attcttacat 300
tccaactcca gaacgtgata ctgacaaacc attcatgatg ccagttgagg atgtattctc 360
aatcactggt cgtggaactg ttgcaactgg acgtgttgaa cgtggacaag ttaaagttgg 420
tgacgaagta gaagttatcg gtattgaaga agaaagcaaa aaagtaatag taactggagt 480
agaaatgttc cgtaaattac tagactacgc tgaagctggc gacaacattg gcgcacttct 540
acgtggtgtt gctcgtgaag atatccaacg tggtcaagta ttagctaaac caggttcgat 600
tactccacat actaacttca aagctgaaac ttatgtttta actaaagaag aaggtggacg 660
tcacactcca ttcttcaaca actaccgccc acaattctat ttccgtacta ctgacgtaac 720
tggtattgtt acacttccag aaggtactga aatggtaatg cctggtgata acattgagct 780
tgcagttgaa ctaattgcac caatcgctat cgaagac 817

<210> SEQ ID NO 140
<211> LENGTH: 814
<212> TYPE: DNA
<213> ORGANISM: Staphylococcus aureus

<400> SEQUENCE: 140
cggtggtatc ttagtagtat ctgctgctga cggtccaatg ccacaaactc gtgaacacat 60
tcttttatca cgtaacgttg gtgtaccagc attagtagta ttcttaaaca aagttgacat 120
ggttgacgat gaagaattat tagaattagt agaaatggaa gttcgtgact tattaagcga 180
atatgacttc ccaggtgacg atgtacctgt aatcgctggt tcagcattar aagctttaga 240
aggcgatgct caatacgaag aaaaaatctt agaattartg gaagctgtag atacttacat 300
tccaactcca gaacgtgatt ctgacaaacc attcatgatg ccagttgagg acgtattctc 360
aatcactggt cgtggtactg ttgctacagg ccgtgttgaa cgtggtcaaa tcaaagttgg 420
tgaagaagtt gaaatcatcg gtttacatga cacatctaaa acaactgtta caggtgttga 480
aatgttccgt aaattattag actacgctga agctggtgac aacattggtg cattattacg 540
tggtgttgct cgtgaagacg tacaacgtgg tcaagtatta gctgctcctg gttcaattac 600
accacatact gaattcaaag cagaagtata cgtattatca aaagacgaag gtggacgtca 660
cactccattc ttctcaaact atcgtccaca attctatttc cgtactactg acgtaactgg 720
tgttgttcac ttaccagaag gtactgaaat ggtaatgcct ggtgataacg ttgaaatgac 780
agtagaatta atcgctccaa tcgcgattga agac 814

<210> SEQ ID NO 141
<211> LENGTH: 814
<212> TYPE: DNA
<213> ORGANISM: Staphylococcus epidermidis

<400> SEQUENCE: 141
cggcggtatc ttagttgtat ctgctgctga cggtccaatg ccacaaactc gtgaacacat 60
cttattatca cgtaacgttg gtgtaccagc attagttgta ttcttaaaca aagttgacat 120
ggtagacgac gaagaattat tagaattagt tgaaatggaa gttcgtgact tattaagcga 180
atatgacttc ccaggtgacg atgtacctgt aatcgctggt tctgcattaa aagcattaga 240
aggcgatgct gaatacgaac aaaaaatctt agacttaatg caagcagttg atgattacat 300
tccaactcca gaacgtgatt ctgacaaacc attcatgatg ccagttgagg acgtattctc 360
aatcactggt cgtggtactg ttgctacagg ccgtgttgaa cgtggtcaaa tcaaagtwgg 420

```
tgaagaagtt gaaatcatcg gtatgcacga aacttctaaa acaactgtta ctggtgtaga    480

aatgttccgt aaattattag actacgctga agctggtgac aacatcggtg ctttattacg    540

tggtgttgca cgtgaagacg tacaacgtgg tcaagtatta gctgctcctg gttctattac    600

accacacaca aaattcaaag ctgaagtata cgtattatct aaagatgaag gtggacgtca    660

cactccattc ttcactaact atcgcccaca attctatttc crtactactg acgtaactgg    720

tgttgtaaac ttaccagaag gtacagaaat ggttatgcct ggcgacaacg ttgaaatgac    780

agttgaatta atcgctccaa tcgctatcga agac                                814
```

<210> SEQ ID NO 142
<211> LENGTH: 817
<212> TYPE: DNA
<213> ORGANISM: Staphylococcus saprophyticus

<400> SEQUENCE: 142

```
cggagctatc ttagtagtat ctgctgctga tggcccaatg ccacaaactc gtgaacacat     60

tcttttatca cgtracgttg gtgytccagc attagttgta ttcttaaaca aagttgacat    120

ggttgacgay gaagaattat tagaattrgt agaaatggaa gttcgtgrct tattaagcga    180

atatgacttc ccaggtgacg atgtacctgt aatctctggt tctgcattaa aagctttaga    240

aggcgacgct gactatgagc aaaaaatctt agacttaatg caagctgttg atgactycat    300

tccaacacca gaacgtgatt ctgacaaacc attcatgatg ccagttgagg acgtattctc    360

aatcactggt cgtggtactg ttgctacagg ccgtgttgaa cgtggtcaaa tcaaagtcgg    420

tgaagaaatc garatcatcg gtatgcaaga agaatcaagc aaaacaactg ttactggtgt    480

agaaatgttc cgtaaattat tagactacgc tgaagctggt gacaacattg gtgcattatt    540

acgtggtgtt tcacgtgatg atgtacaacg tggtcaagtt ttagctgctc ctggtactat    600

cacaccacat acaaaattca aagcggatgt ttacgtttta tctaaagatg aaggtggtcg    660

tcatacgcca ttcttcacta actaccgccc acaattctat ttccgtacta ctgacgtaac    720

tggtgttgtt aacttaccag aaggtactga aatggttatg cctggcgata acgttgaaat    780

ggatgttgaa ttaatttctc caatcgctat tgaagac                             817
```

<210> SEQ ID NO 143
<211> LENGTH: 817
<212> TYPE: DNA
<213> ORGANISM: Staphylococcus simulans

<400> SEQUENCE: 143

```
cggcggtatc ttagtagtat ctgctgcaga tggtccaatg ccacaaactc gtgaacacat     60

cttattatca cgtaacgttg gtgtaccagc tttagttgta ttcttaaaca aagctgacat    120

ggttgacgac gaagaattat tagaattagt tgaaatggaa gttcgtgact tattatctga    180

atacgacttc cctggtgacg atgtaccagt tatcgttggt tctgcattaa aagctttaga    240

aggcgaccca gaatacgaac aaaaaatctt agacttaatg caagctgtag atgactacat    300

cccaactcca gaacgtgact ctgataaacc attcatgatg ccagttgagg acgtattctc    360

aatcactggt cgtggtactg tagcaacagg ccgtgttgaa cgtggtcaaa tcaaagtcgg    420

tgaagaagtt gaaatcatcg gtatcactga agaaagcaag aaaacaacag ttacaggtgt    480

agaaatgttc cgtaaattat tagactacgc tgaagctggt gacaacatcg gtgctttatt    540

acgtggtgtt gcacgtgaag acgtacaacg tggacaagta ttagcagctc ctggctctat    600

tactccacac acaaaattca aagctgatgt ttacgtttta tctaaagaag aaggtggacg    660
```

-continued

```
tcatactcca ttcttcacta actaccgccc acaattctac ttccgtacta ctgacgtaac    720

tggcgttgtt cacttaccag aaggtactga aatggttatg cctggcgata acgtagaaat    780

gactgttgaa ttgatcgctc caatcgcgat tgaagac                             817
```

```
<210> SEQ ID NO 144
<211> LENGTH: 817
<212> TYPE: DNA
<213> ORGANISM: Streptococcus agalactiae

<400> SEQUENCE: 144

cggagctatc cttgtagttg cttcaactga tggaccaatg ccacaaactc gtgagcacat     60

ccttctttca cgtcaagttg gtgttaaaca ccttatcgta ttcatgaaca aagttgacct    120

tgttgatgat gaagaattgc ttgaattggt tgaaatggaa attcgtgacc ttctttcaga    180

atacgacttc ccaggtgatg accttccagt tatccaaggt tcagctctta aagcacttga    240

aggcgacgaa aaatacgaag acatcatcat ggaattgatg agcactgttg atgagtacat    300

tccagaacca gaacgtgata ctgacaaacc tttacttctt ccagttgaag atgtattctc    360

aatcactgga cgtggtacag ttgcttcagg acgtatcgac cgtggtactg ttcgtgtcaa    420

cgacgaagtt gaaatcgttg gtattaaaga agatatccaa aaagcagttg ttactggtgt    480

tgaaatgttc cgtaaacaac ttgacgaagg tcttgcaggg gacaacgttg gtgttcttct    540

tcgtggtgtt caacgtgatg aaatcgaacg tggtcaagtt cttgctaaac caggttcaat    600

caacccacac actaaattta aaggtgaagt ttacatcctt tctaaagaag aaggtggacg    660

tcatactcca ttcttcaaca actaccgtcc acaattctac ttccgtacaa ctgacgtaac    720

aggttcaatc gaacttccag caggaacaga aatggttatg cctggtgata acgttactat    780

cgaagttgaa ttgattcacc caatcgccgt agaacaa                             817
```

```
<210> SEQ ID NO 145
<211> LENGTH: 817
<212> TYPE: DNA
<213> ORGANISM: Streptococcus pneumoniae

<400> SEQUENCE: 145

cggagctatc cttgtagtag cttcaactga cggaccaatg ccacaaactc gtgagcacat     60

ccttctttca cgtcaggttg gtgttaaaca ccttatcgtc ttcatgaaca aagttgactt    120

ggttgacgac gaagaattgc ttgaattggt tgaaatggaa atccgtgacc tattgtcaga    180

atacgacttc ccaggtgacg atcttccagt tatccaaggt tcagcactta aagctcttga    240

aggtgactct aaatacgaag acatcgttat ggaattgatg aacacagttg atgagtatat    300

cccagaacca gaacgtgaca ctgacaaacc attgcttctt ccagtcgagg acgtattctc    360

aatcactgga cgtggtacag ttgcttcagg acgtatcgac cgtggtatcg ttaaagtcaa    420

cgacgaaatc gaaatcgttg gtatcaaaga agaaactcra aaagcagttg ttactggtgt    480

tgaaatgttc cgtaaacaac ttgacgaagg tcttgctgga gataacgtag gtgtccttct    540

tcgtggtgtt caacgtgatg aaatcgaacg tggacaagtt atcgctaaac caggttcaat    600

caacccacac actaaattca aaggtgaagt ctacatcctt actaaagaag aaggtggacg    660

tcacactcca ttcttcaaca actaccgtcc acaattctac ttccgtacta ctgacgttac    720

aggttcaatc gaacttccag caggtactga aatggtaatg cctggtgata acgtgacaat    780

cgacgttgag ttgattcacc caatcgccgt agaacaa                             817
```

```
<210> SEQ ID NO 146
```

<211> LENGTH: 817
<212> TYPE: DNA
<213> ORGANISM: Streptococcus salivarius

<400> SEQUENCE: 146

```
cggtgcgatc cttgtagtag catctactga cggaccaatg ccacaaactc gtgagcacat     60

ccttctttca cgtcaggttg gtgttaaaca ccttatcgtc ttcatgaaca aagttgactt    120

ggttgacgat gaagaattgc ttgaattggt tgaaatggaa atccgtgacc ttctttcaga    180

atacgatttc ccaggtgatg acattccagt tatccaaggt tcagctctta aagctcttga    240

aggtgattct aaatacgaag acatcatcat ggacttgatg aacactgttg acgaatacat    300

cccagaacca gaacgtgaca ctgacaaacc attgttgctt ccagtcgaag acgtattctc    360

aatcactggt cgtggtactg ttgcttcagg acgtatcgac cgtggtgttg ttcgtgtcaa    420

tgacgaagtt gaaatcgttg gtcttaaaga agacatccaa aaagcagttg ttactggtgt    480

tgaaatgttc cgtaaacaac ttgacgragg tattgccgga gataacgtcg gtgttcttct    540

tcgtggtatc caacgtgatg aaatcgaacg tggtcaagta ttggctgcac ctggttcaat    600

caacccacac actaaattca aaggtgaagt ttacatcctt tctaaagaag aaggtggacg    660

tcacactcca ttcttcaaca actaccgtcc acagttctac ttccgtacaa ctgacgtaac    720

aggttcaatc gaacttcctg caggtactga aatggttatg cctggtgata acgtgactat    780

cgacgttgag ttgatccacc caatcgccgt tgaacaa                             817
```

<210> SEQ ID NO 147
<211> LENGTH: 897
<212> TYPE: DNA
<213> ORGANISM: Agrobacterium tumefaciens

<400> SEQUENCE: 147

```
aacatgatca ccggtgctgc cgagatggac ggcgcgatcc tggtttgctc ggctgccgac     60

ggcccgatgc cacagacccg cgagcacatc ctgcttgccc gtcaggtggg cgttccggcc    120

atcgtcgtgt tcctcaacaa ggtcgaccag gttgacgacg ccgagcttct cgagctcgtc    180

gagcttgaag ttcgcgaact tctgtcgtcc tacgacttcc cgggcgacga tatcccgatc    240

atcaagggtt cggcacttgc tgctcttgaa gattctgaca agaagatcgg tgaagacgcg    300

atccgcgagc tgatggctgc tgtcgacgcc tacatcccga cgcctgagcg tccgatcgac    360

cagccgttcc tgatgccgat cgaagacgtg ttctcgatct cgggtcgtgg tacggttgtg    420

acgggtcgcg ttgagcgcgg tatcgtcaag gttggtgaag aagtcgaaat cgtcggcatc    480

cgtccgacct cgaagacgac tgttaccggc gttgaaatgt tccgcaagct gctcgaccag    540

ggccaggccg gcgacaacat cggtgcactc gttcgcggcg ttacccgtga cggcgtcgag    600

cgtggtcaga tcctgtgcaa gccgggttcg gtcaagccgc acaagaagtt catggcagaa    660

gcctacatcc tgacgaagga agaaggcggc cgtcatacgc cgttcttcac gaactaccgt    720

ccgcagttct acttccgtac gactgacgtt accggtatcg tttcgcttcc tgaaggcacg    780

gaaatggtta tgcctggcga caacgtcact gttgaagtcg agctgatcgt tccgatcgcg    840

atggaagaaa agctgcgctt cgctatccgc gaaggcggcc gtaccgtcgg cgccggc       897
```

<210> SEQ ID NO 148
<211> LENGTH: 885
<212> TYPE: DNA
<213> ORGANISM: Bacillus subtilis

<400> SEQUENCE: 148

```
atgatcactg gtgctgcgca aatggacgga gctatccttg tagtatctgc tgctgatggc     60

ccaatgccac aaactcgtga gcacatcctt ctttctaaaa acgttggtgt accatacatc    120

gttgtattct taaacaaatg cgacatggta gacgacgaag agcttcttga actagttgaa    180

atggaagttc gcgatcttct tagcgaatac gacttccctg gtgatgatgt accagttgtt    240

aaaggttctg ctcttaaagc tcttgaagga gacgctgagt gggaagctaa aatcttcgaa    300

cttatggatg cggttgatga gtacatccca actccagaac gcgacactga aaaaccattc    360

atgatgccag ttgaggacgt attctcaatc actggtcgtg gtacagttgc tactggccgt    420

gtagaacgcg gacaagttaa agtcggtgac gaagttgaaa tcatcggtct tcaagaagag    480

aacaagaaaa caactgttac aggtgttgaa atgttccgta agcttcttga ttacgctgaa    540

gctggtgaca acattggtgc ccttcttcgc ggtgtatctc gtgaagaaat ccaacgtggt    600

caagtacttg ctaaaccagg tacaatcact ccacacagca aattcaaagc tgaagtttac    660

gttctttcta aagaagaggg tggacgtcat actccattct tctctaacta ccgtcctcag    720

ttctacttcc gtacaactga cgtaactggt atcatccatc ttccagaagg cgtagaaatg    780

gttatgcctg gagataacac tgaaatgaac gttgaactta tttctacaat cgctatcgaa    840

gaaggaactc gtttctctat tcgtgaaggc ggacgtactg ttggt                    885
```

<210> SEQ ID NO 149
<211> LENGTH: 882
<212> TYPE: DNA
<213> ORGANISM: Bacteroides fragilis

<400> SEQUENCE: 149

```
atggttactg gtgctgctca gatggacggt gctatcattg tagttgctgc tactgatggt     60

ccgatgcctc agactcgtga gcacatcctt ttggctcgtc aggtaaacgt tccgaagctg    120

gttgtattca tgaacaagtg cgatatggtt gaagatgctg agatgttgga acttgttgaa    180

atggaaatga gagaattgct ttcattctat gatttcgacg gtgacaatac tccgatcatt    240

cagggttctg ctcttggtgc attgaacggc gtagaaaaat gggaagacaa agtaatggaa    300

ctgatggaag ctgttgatac ttggattcca ctgcctccgc gcgatgttga taaacctttc    360

ttgatgccgg tagaagacgt gttctctatc acaggtcgtg gtactgtagc tacaggtcgt    420

atcgaaactg gtgttatcca tgtaggtgat gaaatcgaaa tcctcggttt gggtgaagat    480

aagaaatcag ttgtaacagg tgttgaaatg ttccgcaaac ttctggatca gggtgaagct    540

ggtgacaacg taggtctgtt gcttcgtggt gttgacaaga acgaaatcaa acgtggtatg    600

gttctttgta aaccgggtca gattaaacct cactctaaat tcaaagcaga ggtttatatc    660

ctgaagaaag aagaaggtgg tcgtcacact ccattccata acaaatatcg tcctcagttc    720

tacctgcgta ctatggactg tacaggtgaa atcactcttc cggaaggaac tgaaatggta    780

atgccgggtg ataacgtaac tatcactgta gagttgatct atccggttgc actgaacatc    840

ggtcttcgtt tcgctatccg cgaaggtgga cgtacagtag gt                       882
```

<210> SEQ ID NO 150
<211> LENGTH: 888
<212> TYPE: DNA
<213> ORGANISM: Borrelia burgdorferi

<400> SEQUENCE: 150

```
aatatgatta caggagcagc tcaaatggat gcagcgatac ttttagttgc tgctgatagt     60

ggtgctgagc ctcaaacaaa agagcatttg cttcttgctc aaagaatggg aataaagaaa    120
```

-continued

```
ataatagttt ttttaaataa attggactta gcagatcctg aacttgttga gcttgttgaa    180

gttgaagttt tagaacttgt tgaaaaatat ggcttttcag ctgatactcc aataatcaaa    240

ggttcagctt ttggggctat gtcaaatcca gaagatcctg aatctacaaa atgcgttaaa    300

gaacttcttg aatctatgga taattatttt gatcttccag aaagagatat tgacaagcca    360

tttttgcttg ctgttgaaga tgtattttct atttcaggaa gaggcactgt tgctactggg    420

cgtattgaaa gaggtattat taaagttggt caagaagttg aaatagttgg aattaaagaa    480

accagaaaaa ctactgttac tggtgttgaa atgttccaga aaattcttga gcaaggtcaa    540

gcaggggata atgttggtct tcttttgaga ggcgttgata aaaaagacat tgagaggggg    600

caagttttgt cagctccagg tacaattact ccacacaaga aatttaaagc ttcaatttat    660

tgtttgacta aagaagaagg cggtaggcac aagccatttt tcccagggta tagaccacag    720

ttctttttta gaacaaccga tgttactgga gttgttgctt tagagggcaa agaaatggtt    780

atgcctggtg ataatgttga tattattgtt gagctgatct cttcaatagc tatggataag    840

aatgtagaat ttgctgttcg agaaggtgga agaaccgttg cttcagga                 888
```

<210> SEQ ID NO 151
<211> LENGTH: 894
<212> TYPE: DNA
<213> ORGANISM: Brevibacterium linens

<400> SEQUENCE: 151

```
aacatgatca ccggtgccgc tcagatggac ggtgcgatcc tcgtcgtcgc cgctaccgac     60

ggaccgatgc cccagacccg tgagcacgtg ctgctcgcgc gtcaggtcgg cgttccctac    120

atcgtcgtgg ctctgaacaa gtccgacatg gtcgatgacg aggagctcct cgagctcgtc    180

gaattcgagg tccgcgacct gctctcgagc caggacttcg acggagacaa cgctccggtc    240

attccggtgt ccgctctcaa ggcgctggaa ggcgacgaga agtgggtcaa gagcgttcag    300

gatctcatgg ctgccgtcga tgacaacgtt ccggagccgg agcgcgatgt cgacaagccg    360

ttcctcatgc ccgtcgagga cgtcttcacg atcaccggtc gtggaaccgt cgtcaccggt    420

cgtgtcgagc gcggcgtgct cctgcctaac gacgaaatcg aaatcgtcgg catcaaggag    480

aagtcgtcca agacgactgt caccgctatc gagatgttcc gcaagaccct gccggatgcc    540

cgtgcaggtg agaacgtcgg tctgctcctc cgcggcacca agcgcgagga tgttgagcgc    600

ggtcaggtca tcgtgaagcc gggttcgatc accccgcaca ccaagttcga ggctcaggtc    660

tacatcctga gcaaggacga gggcggacgt cacaacccgt tctactcgaa ctaccgtccg    720

cagttctact tccggaccac ggacgtcacc ggtgtcatca cgctgcccga gggcaccgag    780

atggtcatgc ccggcgacaa caccgatatg tcggtcgagc tcatccagcc gatcgctatg    840

gaggaccgcc tccgcttcgc aatccgcgaa ggtggccgca ccgtcggcgc cggt          894
```

<210> SEQ ID NO 152
<211> LENGTH: 888
<212> TYPE: DNA
<213> ORGANISM: Burkholderia cepacia

<400> SEQUENCE: 152

```
atgatcacgg gcgcagcgca gatggacggc gcgatcctgg tttgctcggc agcagacggc     60

ccgatgccgc aaacgcgtga gcacatcctg ctggcgcgtc aggttggtgt tccgtacatc    120

atcgtgttcc tgaacaagtg cgacagtgtg gacgacgctg aactgctcga gctggtcgag    180

atggaagttc gcgaactcct gtcgaagtac gacttcccgg gcgacgacac gccgatcgtg    240
```

-continued

```
aagggttcgg ccaagctggc gctggaaggc gacacgggcg agctgggcga agtggcgatc    300

atgagcctgg cagacgcgct ggacacgtac atcccgacgc cggagcgtgc agttgacggc    360

gcgttcctga tgccggtgga agacgtgttc tcgatctcgg gccgtggtac ggtggtgacg    420

ggtcgtgtcg agcgcggcat cgtgaaggtc ggcgaagaaa tcgaaatcgt cggtatcaag    480

ccgacggtga agacgacctg cacgggcgtt gaaatgttcc gcaagctgct ggaccaaggt    540

caggcaggcg acaacgtcgg tatcctgctg cgcggcacga agcgtgaaga cgtggagcgt    600

ggccaggttc tggcgaagcc gggttcgatc acgccgcaca cgcacttcac ggctgaagtg    660

tacgtgctga gcaaggacga aggcggccgt cacacgccgt tcttcaacaa ctaccgtccg    720

cagttctact tccgtacgac ggacgtgacg ggctcgatcg agctgccgaa ggacaaggaa    780

atggtgatgc cgggcgacaa cgtgtcgatc acggtgaagc tgattgctcc gatcgcgatg    840

gaagaaggtc tgcgcttcgc aatccgtgaa ggcggccgta cggtcggc                 888
```

<210> SEQ ID NO 153
<211> LENGTH: 891
<212> TYPE: DNA
<213> ORGANISM: Chlamydia trachomatis

<400> SEQUENCE: 153

```
aacatgatca ccggtgcggc tcaaatggac ggggctattc tagtagtttc tgcaacagac     60

ggagctatgc ctcaaactaa agagcatatt cttttggcaa gacaagttgg ggttccttac    120

atcgttgttt ttctcaataa aattgacatg atttccgaag aagacgctga attggtcgac    180

ttggttgaga tggagttggc tgagcttctt gaagagaaag gatacaaagg gtgtccaatc    240

atcagaggtt ctgctctgaa agctttggaa ggagatgctg catacataga gaaagttcga    300

gagctaatgc aagccgtcga tgataatatc cctactccag aaagagaaat tgacaagcct    360

ttcttaatgc ctattgagga cgtgttctct atctccggac gaggaactgt agtaactgga    420

cgtattgagc gtggaattgt taaagtttcc gataaagttc agttggtcgg tcttagagat    480

actaaagaaa cgattgttac tggggttgaa atgttcagaa aagaactccc agaaggtcgt    540

gcaggagaga acgttggatt gctcctcaga ggtattggta agaacgatgt ggaaagagga    600

atggttgttt gcttgccaaa cagtgttaaa cctcatacac agtttaagtg tgctgtttac    660

gttctgcaaa aagaagaagg tggacgacat aagcctttct tcacaggata tagacctcaa    720

ttcttcttcc gtacaacaga cgttacaggt gtggtaactc tgcctgaggg agttgagatg    780

gtcatgcctg ggataacgt tgagtttgaa gtgcaattga ttagccctgt ggctttagaa     840

gaaggtatga gatttgcgat tcgtgaaggt ggtcgtacaa tcggtgctgg a             891
```

<210> SEQ ID NO 154
<211> LENGTH: 891
<212> TYPE: DNA
<213> ORGANISM: Escherichia coli

<400> SEQUENCE: 154

```
aacatgatca ccggtgctgc gcagatggac ggcgcgatcc tggtagttgc tgcgactgac     60

ggcccgatgc cgcagactcg tgagcacatc ctgctgggtc gtcaggtagg cgttccgtac    120

atcatcgtgt tcctgaacaa atgcgacatg gttgatgacg aagagctgct ggaactggtt    180

gaaatggaag ttcgtgaact tctgtctcag tacgacttcc cgggcgacga cactccgatc    240

gttcgtggtt ctgctctgaa agcgctggaa ggcgacgcag agtgggaagc gaaaatcctg    300

gaactggctg gcttcctgga ttcttacatt ccggaaccag agcgtgcgat tgacaagccg    360
```

-continued

```
ttcctgctgc cgatcgaaga cgtattctcc atctccggtc gtggtaccgt tgttaccggt    420

cgtgtagaac gcggtatcat caaagttggt gaagaagttg aaatcgttgg tatcaaagag    480

actcagaagt ctacctgtac tggcgttgaa atgttccgca aactgctgga cgaaggccgt    540

gctggtgaga acgtaggtgt tctgctgcgt ggtatcaaac gtgaagaaat cgaacgtggt    600

caggtactgg ctaagccggg caccatcaag ccgcacacca agttcgaatc tgaagtgtac    660

attctgtcca aagatgaagg cggccgtcat actccgttct tcaaaggcta ccgtccgcag    720

ttctacttcc gtactactga cgtgactggt accatcgaac tgccggaagg cgtagagatg    780

gtaatgccgg gcgacaacat caaaatggtt gttaccctga tccacccgat cgcgatggac    840

gacggtctgc gtttcgcaat ccgtgaaggc ggccgtaccg ttggcgcggg c             891
```

<210> SEQ ID NO 155
<211> LENGTH: 891
<212> TYPE: DNA
<213> ORGANISM: Fibrobacter succinogenes

<400> SEQUENCE: 155

```
aacatggtga ctggtgctgc tcagatggac ggcgctatcc tcgttgttgc cgctactgac     60

ggtccgatgc cgcagactcg cgaacacatc cttctcgctc accaggttgg cgtgccgaag    120

atcgtcgtgt tcatgaacaa gtgcgacatg gttgacgatg ctgaaattct cgacctcgtc    180

gaaatggaag ttcgcgaact cctctccaag tatgacttcg acggtgacaa caccccgatc    240

atccgtggtt ccgctctcaa ggccctcgaa ggcgatccgg aataccagga caaggtcatg    300

gaactcatga acgcttgcga cgaatacatc ccgctcccgc agcgcgatac cgacaagccg    360

ttcctcatgc cgatcgaaga cgtgttcacg attactggcc gcggcactgt cgctactggc    420

cgtatcgaac gcggtgtcgt tcgcttgaac gacaaggttg aacgtatcgg tctcggtgaa    480

accaccgaat acgtcatcac cggtgttgaa atgttccgta agctcctcga cgacgctcag    540

gcaggtgaca acgttggtct cctcctccgt ggtgctgaaa agaaggacat cgtccgtggc    600

atggttctcg cagctccgaa gtctgtcact ccgcacaccg aatttaaggc tgaaatctac    660

gttctcacga aggacgaagg tggccgtcac acgccgttca tgaatggcta ccgtccgcag    720

ttctacttcc gcaccaccga cgttactggt acgatccagc tcccggaagg tgtcgaaatg    780

gttactccgg gtgacacggt cacgatccac gtgaacctca tcgctccgat cgctatggaa    840

aagcagctcc gcttcgctat ccgtgaaggt ggacgtactg ttggtgctgg c             891
```

<210> SEQ ID NO 156
<211> LENGTH: 894
<212> TYPE: DNA
<213> ORGANISM: Flavobacterium ferrugineum

<400> SEQUENCE: 156

```
aacatgatca ccggtgctgc ccagatggac ggtgctatct tagttgtggc tgcatcagac     60

ggtcctatgc ctcaaacaaa agaacacatc ctgcttgctg cccaggtagg tgtacctaaa    120

atggttgtgt ttctgaataa agttgacctc gttgacgacg aagagctcct ggagctggtt    180

gagatcgagg ttcgcgaaga actgactaaa cgcggtttcg acggcgacaa cactccaatc    240

atcaaaggtt ccgctacagg cgccctcgct ggtgaagaaa agtgggttaa agaaattgaa    300

aacctgatgg acgctgttga cagctacatc ccactgcctc ctcgtccggt tgatctgccg    360

ttcctgatga gcgtagagga cgtattctct atcactggtc gtggtactgt tgctaccggt    420

cgtatcgagc gtggccgtat caaagttggt gagcctgttg agatcgtagg tctgcaggag    480
```

-continued

```
tctcccctga actctaccgt tacaggtgtt gagatgttcc gcaaactcct cgacgaaggt    540

gaagctggtg ataacgccgg tctcctcctc cgtggtgttg aaaaaacaca gatccgtcgc    600

ggtatggtaa tcgttaaacc cggttccatc actccgcaca cggacttcaa aggcgaagtt    660

tacgtactga gcaaagacga aggtggccgt cacactccat tcttcaacaa ataccgtcct    720

caattctact tccgtacaac tgacgttaca ggtgaagtag aactgaacgc aggaacagaa    780

atggttatgc ctggtgataa caccaacctg accgttaaac tgatccaacc gatcgctatg    840

gaaaaaggtc tgaaattcgc gatccgcgaa ggtggccgta ccgtaggtgc agga          894
```

<210> SEQ ID NO 157
<211> LENGTH: 891
<212> TYPE: DNA
<213> ORGANISM: Haemophilus influenzae

<400> SEQUENCE: 157

```
aatatgatta ctggtgcggc acaaatggat ggtgctattt tagtagtagc agcaacagat     60

ggtcctatgc cacaaactcg tgaacacatc ttattaggtc gccaagtagg tgttccatac    120

atcatcgtat tcttaaacaa atgcgacatg gtagatgacg aagagttatt agaattagtc    180

gaaatggaag ttcgtgaact tctatctcaa tatgacttcc caggtgacga tacaccaatc    240

gtacgtggtt cagcattaca agcgttaaac ggcgtagcag aatgggaaga aaaaatcctt    300

gagttagcaa accacttaga tacttacatc ccagaaccag aacgtgcgat tgaccaaccg    360

ttccttcttc caatcgaaga tgtgttctca atctcaggtc gtggtactgt agtaacaggt    420

cgtgtagaac gaggtattat ccgtacaggt gatgaagtag aaatcgtcgg tatcaaagat    480

acagcgaaaa ctactgtaac gggtgttgaa atgttccgta aattacttga cgaaggtcgt    540

gcaggtgaaa acatcggtgc attattacgt ggtaccaaac gtgaagaaat cgaacgtggt    600

caagtattag cgaaaccagg ttcaatcaca ccacacactg acttcgaatc agaagtgtac    660

gtattatcaa aagatgaagg tggtcgtcat actccattct tcaaaggtta ccgtccacaa    720

ttctatttcc gtacaacaga cgtgactggt acaatcgaat taccagaagg cgtggaaatg    780

gtaatgccag gcgataacat caagatgaca gtaagcttaa tccacccaat tgcgatggat    840

caaggtttac gtttcgcaat ccgtgaaggt ggccgtacag taggtgcagg c             891
```

<210> SEQ ID NO 158
<211> LENGTH: 906
<212> TYPE: DNA
<213> ORGANISM: Helicobacter pylori

<400> SEQUENCE: 158

```
aacatgatca ccggtgcggc gcaaatggac ggagcgattt tggttgtttc tgcagctgat     60

ggccctatgc ctcaaactag ggagcatatc ttattgtctc gtcaagtagg cgtgcctcac    120

atcgttgttt tcttaaacaa acaagacatg gtagatgacc aagaattgtt agaacttgta    180

gaaatggaag tgcgcgaatt gttgagcgcg tatgaatttc ctggcgatga cactcctatc    240

gtagcgggtt cagctttaag agctttagaa gaagcaaagg ctggtaatgt gggtgaatgg    300

ggtgaaaaag tgcttaaact tatggctgaa gtggatgcct atatccctac tccagaaaga    360

gacactgaaa aaactttctt gatgccggtt gaagatgtgt tctctattgc gggtagaggg    420

actgtggtta caggtaggat tgaaagaggc gtggtgaaag taggcgatga agtggaaatc    480

gttggtatca gacctacaca aaaaacgact gtaaccggtg tagaaatgtt taggaaagag    540

ttggaaaaag gtgaagccgg cgataatgtg ggcgtgcttt tgagaggaac taaaaaagaa    600
```

-continued gaagtggaac gcggtatggt tctatgcaaa ccaggttcta tcactccgca caagaaattt 660
gagggagaaa tttatgtcct ttctaaagaa gaaggcggga gacacactcc attcttcacc 720
aattaccgcc cgcaattcta tgtgcgcaca actgatgtga ctggctctat caccccttcct 780 gaaggcgtag aaatggttat gcctggcgat aatgtgaaaa tcactgtaga gttgattagc 840
cctgttgcgt tagagttggg aactaaattt gcgattcgtg aaggcggtag gaccgttggt 900
gctggt 906

<210> SEQ ID NO 159
<211> LENGTH: 891
<212> TYPE: DNA
<213> ORGANISM: Micrococcus luteus

<400> SEQUENCE: 159
aacatgatca ccggcgccgc tcagatggac ggcgcgatcc tcgtggtcgc cgctaccgac 60
ggcccgatgg cccagacccg tgagcacgtg ctcctggccc gccaggtcgg cgtgccggcc 120
ctgctcgtgg ccctgaacaa gtcggacatg gtggaggacg aggagctcct cgagcgtgtc 180
gagatggagg tccggcagct gctgtcctcc aggagcttcg acgtcgacga ggccccggtc 240
atccgcacct ccgctctgaa ggccctcgag ggcgaccccc agtgggtcaa gtccgtcgag 300
gacctcatgg atgccgtgga cgagtacatc ccggacccgg tgcgcgacaa ggacaagccg 360
ttcctgatgc cgatcgagga cgtcttcacg atcaccggcc gtggcaccgt ggtgaccggt 420
cgcgccgagc gcggcaccct gaagatcaac tccgaggtcg agatcgtcgg catccgcgac 480
gtgcagaaga ccactgtcac cggcatcgag atgttccaca agcagctcga cgaggcctgg 540
gccggcgaga actgcggtct gctcgtgcgc ggtctgaagc gcgacgacgt cgagcgcggc 600
caggtgctgg tggagccggg ctccatcacc ccgcacacca acttcgaggc gaacgtctac 660
atcctgtcca aggacgaggg tggcgtcac accccgttct actcgaacta ccgcgcgcag 720
ttctacttcc gcaccaccga cgtcaccggc gtcatcacgc tgcccgaggg caccgagatg 780
gtcatgcccg gcgacaccac cgagatgtcg gtcgagctca tccagccgat cgccatggag 840
gagggcctcg gcttcgccat ccgcgagggt ggccgcaccg tgggctccgg c 891

<210> SEQ ID NO 160
<211> LENGTH: 891
<212> TYPE: DNA
<213> ORGANISM: Mycobacterium tuberculosis

<400> SEQUENCE: 160
aacatgatca ccggcgccgc gcagatggac ggtgcgatcc tggtggtcgc cgccaccgac 60
ggcccgatgc cccagacccg cgagcacgtt ctgctggcgc gtcaagtggg tgtgccctac 120
atcctggtag cgctgaacaa ggccgacgca gtggacgacg aggagctgct cgaactcgtc 180
gagatggagg tccgcgagct gctggctgcc caggaattcg acgaggacgc cccggttgtg 240
cgggtctcgg cgctcaaggc gctcgagggt gacgcgaagt gggttgcctc tgtcgaggaa 300
ctgatgaacg cggtcgacga gtcgattccg gacccggtcc gcgagaccga caagccgttc 360
ctgatgccgg tcgaggacgt cttcaccatt accggccgcg gaaccgtggt caccggacgt 420
gtggagcgcg gcgtgatcaa cgtgaacgag gaagttgaga tcgtcggcat tcgcccatcg 480
accaccaaga ccaccgtcac cggtgtggag atgttccgca agctgctcga ccagggccag 540
gcgggcgaca acgttggttt gctgctgcgg ggcgtcaagc gcgaggacgt cgagcgtggc 600
caggttgtca ccaagcccgg caccaccacg ccgcacaccg agttcgaagg ccaggtctac 660

-continued

```
atcctgtcca aggacgaggg cggccggcac acgccgttct tcaacaacta ccgtccgcag    720

ttctacttcc gcaccaccga cgtgaccggt gtggtgacac tgccggaggg caccgagatg    780

gtgatgcccg gtgacaacac caacatctcg gtgaagttga tccagcccgt cgccatggac    840

gaaggtctgc gtttcgcgat ccgcgagggt ggccgcaccg tgggcgccgg c             891
```

```
<210> SEQ ID NO 161
<211> LENGTH: 891
<212> TYPE: DNA
<213> ORGANISM: Mycoplasma genitalium

<400> SEQUENCE: 161

aatatgatca caggtgctgc acaaatggat ggagctattc tagttgtttc agcaactgat     60

agtgtgatgc cccaaacccg cgagcacatc ttacttgccc gccaagtagg ggttcctaaa    120

atggtagttt ttctaaacaa gtgtgatatt gctagtgatg aagaggtaca agaacttgtt    180

gctgaagaag tacgtgatct gttaacttcc tatggttttg atggtaagaa cactcctatt    240

atttatggct cagctttaaa agcattggaa ggtgatccaa agtgggaggc taagatccat    300

gatttgatta aagcagttga tgaatggatt ccaactccta cacgtgaagt agataaacct    360

ttcttattag caattgaaga tacgatgacc attactggta gaggtacagt tgttacagga    420

agagttgaaa gaggtgaact caaagtaggt caagaagttg aaattgttgg tttaaaacca    480

attagaaaag cagttgttac tggaattgaa atgttcaaaa aggaacttga ttcagcaatg    540

gctggtgaca atgctggggt attattacgt ggtgttgaac gtaaagaagt tgaaagaggt    600

caagttttag caaaaccagg ctctattaaa ccgcacaaga aatttaaagc tgagatctat    660

gctttaaaga aagaagaagg tggtagacac actggttttt taaacggtta ccgtcctcaa    720

ttctatttcc gtaccactga tgtaactggt tctattgctt tagctgaaaa tactgaaatg    780

gttctacctg gtgataatgc ttctattact gttgagttaa ttgctcctat cgcttgtgaa    840

aaaggtagta agttctcaat tcgtgaaggt ggtagaactg taggggcagg c             891
```

```
<210> SEQ ID NO 162
<211> LENGTH: 891
<212> TYPE: DNA
<213> ORGANISM: Neisseria gonorrhoeae

<400> SEQUENCE: 162

aacatgatta ccggcgccgc acaaatggac ggtgcaatcc tggtatgttc tgctgccgac     60

ggccctatgc cgcaaacccg cgaacacatc ctgctggccc gtcaagtagg cgtaccttac    120

atcatcgtgt tcatgaacaa atgcgacatg gtcgacgatg ccgagctgtt ccaactggtt    180

gaaatggaaa tccgcgacct gctgtccagc tacgacttcc ccggcgacga ctgcccgatc    240

gtacaaggtt ccgcactgaa agccttggaa ggcgatgccg cttacgaaga aaaaatcttc    300

gaactggcta ccgcattgga cagatacatc ccgactcccg agcgtgccgt ggacaaacca    360

ttcctgctgc ctatcgaaga cgtgttctcc atttccggcc gcggtaccgt agtcaccggc    420

cgtgtagagc gaggtatcat ccacgttggt gacgagattg aaatcgtcgg tctgaaagaa    480

acccaaaaaa ccacctgtac cggcgttgaa atgttccgca aactgctgga cgaaggtcag    540

gcgggcgaca acgtaggcgt attgctgcgc ggtaccaaac gtgaagacgt agaacgcggt    600

caggtattgg ccaaacgggg tactatcact cctcacacca agttcaaagc agaagtgtac    660

gtattgagca aagaagaggg cggcccccat accccgtttt tcgccaacta ccgtccccaa    720

ttctacttcc gtaccactga cgtaaccggc acgattactt tggaaaaagg tgtggaaatg    780
```

-continued gtaatgccgg gtgagaacgt aaccattact gtagaactga ttgcgcctat cgctatggaa 840
gaaggtctgc gctttgcgat tcgcgaaggc ggccgtaccg tgggtgccgg c 891

<210> SEQ ID NO 163
<211> LENGTH: 891
<212> TYPE: DNA
<213> ORGANISM: Rickettsia prowazekii

<400> SEQUENCE: 163
aatatgataa ctggtgccgc tcagatggat ggtgctatat tagtagtttc tgctgctgat 60
ggtcctatgc ctcaaactag agaacatata ttactggcaa aacaggtagg tgtacctgct 120
atggtagtat ttttgaataa agtagatatg gtagatgatc ctgacctatt agaattagtt 180
gagatggaag taagagaatt attatcaaaa tatggtttcc ctggtaatga aatacctatt 240
attaaaggtt ctgcacttca agctttagaa ggaaaacctg aaggtgaaaa agctattaat 300
gagttaatga atgcagtaga tacgtatata cctcagccta tagagctaca agataaacct 360
tttttaatgc caatagagga tgtattttct atttcaggca gaggtaccgt tgtaactggt 420
agagtggagt caggcataat taaggtgggt gaagaaattg aaatagtagg tctaaaaaat 480
acgcaaaaaa cgacttgtac aggtgtagaa atgttcagaa aattacttga tgaaggacaa 540
tctggagata atgtcggtat attactacgt ggtacaaaaa gagaagaagt agaaagagga 600
caagtacttg caaaacctgg gagcataaaa ccgcatgata aatttgaagc tgaagtgtat 660
gtgcttagta aagaggaagg tggacgtcat accccattta ctaatgatta tcgcccacag 720
ttctatttta gaacaacaga tgttaccggc acaataaaat tgccttctga taagcagatg 780
gttatgcctg gagataatgc tactttttca gtagaattaa ttaagccgat tgctatgcaa 840
gaagggttaa aattctctat acgtgaaggt ggtagaacag taggagccgg t 891

<210> SEQ ID NO 164
<211> LENGTH: 891
<212> TYPE: DNA
<213> ORGANISM: Salmonella typhimurium

<400> SEQUENCE: 164
aacatgatca ccggtgctgc tcagatggac ggcgcgatcc tggttgttgc tgcgactgac 60
ggcccgatgc cgcagacccg tgagcacatc ctgctgggtc gtcaggtagg cgttccgtac 120
atcatcgtgt tcctgaacaa atgcgacatg gttgatgacg aagagctgct ggaactggtt 180
gagatggaag ttcgcgaact gctgtctcag tacgacttcc cgggcgacga cactccgatc 240
gttcgtggtt ctgctctgaa agcgctggaa ggcgacgcag agtgggaagc gaaaatcatc 300
gaactggctg gcttcctgga ttcttatatt ccggaaccag agcgtgcgat tgacaagccg 360
ttcctgctgc cgatcgaaga cgtattctcc atctccggtc gtggtaccgt tgttaccggt 420
cgtgtagagc gcggtatcat caaagtgggc gaagaagttg aaatcgttgg tatcaaagag 480
actcagaagt ctacctgtac tggcgttgaa atgttccgca aactgctgga cgaaggccgt 540
gccggtgaga acgtaggtgt tctgctgcgt ggtatcaaac gtgaagaaat cgaacgtggt 600
caggtactgg ctaagccggg caccatcaag ccgcacacca agttcgaatc tgaagtgtac 660
attctgtcca aagatgaagg cggccgtcat actccgttct tcaaaggcta ccgtccgcag 720
ttctacttcc gtactactga cgtgactggt accatcgaac tgccggaagg cgtagagatg 780
gtaatgccgg gcgacaacat caaaatggtt gttaccctga tccacccgat cgcgatggac 840
gacggtctgc gtttcgcaat ccgtgaaggc ggccgtaccg ttggcgcggg c 891

-continued

<210> SEQ ID NO 165
<211> LENGTH: 881
<212> TYPE: DNA
<213> ORGANISM: Shewanella putida

<400> SEQUENCE: 165
atgatcactg gtgctgcaca gatggacggc gcgattctgg tagtcgcttc aacagacggt 60
ccaatgccac agactcgtga gcacatcctg ctttctcgtc aggttggcgt accattcatc 120
atcgtattca tgaacaaatg tgacatggta gatgacgaag agctgttaga gctagttgag 180
atggaagtgc gtgaactgtt atcagaatac gatttcccag gtgatgactt accggtaatc 240
caaggttcag ctctgaaagc gctagaaggc gagccagagt gggaagcaaa aatccttgaa 300
ttagcagcgg cgctggattc ttacattcca gaaccacaac gtgacatcga taagccgttc 360
ctactgccaa tcgaagacgt attctcaatt tcaggccgtg gtacagtagt aacaggtcgt 420
gttgagcgtg gtattgtacg cgtaggcgac gaagttgaaa tcgttggtgt acgtgcgaca 480
actaagacaa cgtgtactgg tgtagaaatg ttccgtaaac tgcttgacga aggtcgtgca 540
ggtgagaact gtggtatttt gttacgtggt actaagcgtg atgacgtaga acgtggtcaa 600
gtattagcga agccaggttc aatcaaccca cacactactt ttgaatcaga agtttacgta 660
ctgtcaaaag aagaaggtgg tcgtcacacg ccattcttca aaggctaccg tccacagttc 720
tacttccgta caactgacgt aaccggtact atcgaactgc cagaaggcgt agagatggta 780
atgccaggcg ataacatcaa gatggtagtg acactgattt gcccaatcgc gatggacgaa 840
ggtttacgct tcgcaatccg tgaaggcggt cgtacagtgg t 881

<210> SEQ ID NO 166
<211> LENGTH: 897
<212> TYPE: DNA
<213> ORGANISM: Stigmatella aurantiaca

<400> SEQUENCE: 166
aacatgatca cgggcgcggc gcagatggac ggagcgattc tggtggtgtc cgcggccgac 60
ggcccgatgc cccagacgcg tgagcacatc ctgctggcca ggcaggtggg cgtgccctac 120
atcgtcgtct tcctgaacaa ggtggacatg ctggacgatc cggagctgcg cgagctggtg 180
gagatggagg tgcgcgacct gctcaagaag tacgagttcc cgggcgacag catccccatc 240
atccctggca gcgcgctcaa ggcgctggag ggagacacca gcgacatcgg cgagggagcg 300
atcctgaagc tgatggcggc ggtggacgag tacatcccga cgccgcagcg tgcgacggac 360
aagccgttcc tgatgccggt ggaagacgtg ttctccatcg caggccgagg aacggtggcg 420
acgggccgag tggagcgcgg caagatcaag gtgggcgagg aagtggagat cgtggggatc 480
cgtccgacgc agaagacggt catcacgggg gtggagatgt tccgcaagct gctggacgag 540
ggcatggcgg gagacaacat cggagcgctg ctgcgaggcc tgaagcgcga ggacctggag 600
cgtgggcagg tgctggcgaa ctgggggagc atcaacccgc acacgaagtt caaggcgcag 660
gtgtacgtgc tgtcgaagga agagggaggg cggcacacgc cgttcttcaa gggataccgg 720
ccgcagttct acttccggac gacggacgtg accggaacgg tgaagctgcc ggacaacgtg 780
gagatggtga tgccgggaga caacatcgcc atcgaggtgg agctcattac tccggtcgcc 840
atggagaagg agctgccgtt cgccatccgt gagggtggcc gcacggtggg cgccggc 897

<210> SEQ ID NO 167
<211> LENGTH: 894
<212> TYPE: DNA

<213> ORGANISM: Streptococcus pyogenes

<400> SEQUENCE: 167
aacatgatca ctggtgccgc tcaaatggac ggagctatcc ttgtagttgc ttcaactgat 60
ggaccaatgc cacaaactcg tgagcacatc cttctttcac gtcaggttgg tgttaaacac 120
cttatcgtgt tcatgaacaa agttgacctt gttgatgacg aagagttgct tgaattagtt 180
gagatggaaa ttcgtgacct tctttcagaa tacgatttcc caggtgatga ccttccagtt 240
atccaaggtt cagctcttaa agctcttgaa ggcgacacta aatttgaaga catcatcatg 300
gaattgatgg atactgttga ttcatacatt ccagaaccag aacgcgacac tgacaaacca 360
ttgcttcttc cagtcgaaga cgtattctca attacaggtc gtggtacagt tgcttcagga 420
cgtatcgacc gtggtactgt tcgtgtcaac gacgaaatcg aaatcgttgg tatcaaagaa 480
gaaactaaaa aagctgttgt tactggtgtt gaaatgttcc gtaaacaact tgacgaaggt 540
cttgcaggag acaacgtagg tatccttctt cgtggtgttc aacgtgacga aatcgaacgt 600
ggtcaagtta ttgctaaacc aagttcaatc aacccacaca ctaaattcaa aggtgaagta 660
tatatccttt ctaaagacga aggtggacgt cacactccat tcttcaacaa ctaccgtcca 720
caattctact tccgtacaac tgacgtaaca ggttcaatcg aacttccagc aggtacagaa 780
atggttatgc ctggtgataa cgtgacaatc aacgttgagt tgatccaccc aatcgccgta 840
gaacaaggta ctactttctc aatccgtgaa ggtggacgta ctgttggttc aggt 894

<210> SEQ ID NO 168
<211> LENGTH: 897
<212> TYPE: DNA
<213> ORGANISM: Thiobacillus cuprinus

<400> SEQUENCE: 168
aacatgatca ccggtgcggc ccagatggac ggcgccatcc tggtcgtgtc cgccgccgac 60
ggccccatgc cccaaacccg cgagcacatc ctgctggcgc gtcaggtggg cgtgccctac 120
atcatcgtgt tcctcaacaa gtgcgacatg gtcgacgacg ccgagctgct cgaactcgtc 180
gagatggaag tgcgcgagct gctgtccaag tacgacttcc ccggtgacga cacccccatc 240
atcaagggct cggccaagct ggccctcgaa ggcgacaagg gcgaactggg cgaaggcgcc 300
attctcaagc tggccgaggc cctggacacc tacatcccca cgcccgagcg ggccgtcgac 360
ggcgcgttcc tcatgcccgt ggaagacgtg ttctccatct ccgggcgcgg cacggtggtc 420
accgggcgtg tggagcgcgg catcatcaag gtcggcgagg aaatcgagat tgtcggcctc 480
aagcccaccc tcaagaccac ctgcaccggc gtggaaatgt tcaggaagct gctcgaccag 540
ggccaggccg gcgacaacgt cggcatcttg ctgcgcggca ccaagcgcga ggaagtcgag 600
cgcggccagg tgctgtgcaa acccggctcg atcaagcccc acacccactt caccgccgag 660
gtgtacgtgc tgagcaagga cgagggcggc cgccacaccc ccttcttcaa caactaccgc 720
ccgcagttct acttccgcac caccgacgtc accggcgcca tcgaactgcc caaggacaag 780
gaaatggtca tgcccggcga taatgtgagc atcaccgtca agctcatcgc ccccatcgcc 840
atggaagaag gcctgcgctt cgccatccgc gaaggcggcc gcaccgtcgg cgccggc 897

<210> SEQ ID NO 169
<211> LENGTH: 894
<212> TYPE: DNA
<213> ORGANISM: Treponema pallidum

<400> SEQUENCE: 169

-continued

```
aatatgatca cgggtgctgc gcagatggac ggtggtattc tcgtcgtgtc tgcgcctgac      60

ggcgttatgc cacagacgaa ggagcatctt ctgctcgccc gtcaggttgg tgttccctcc     120

atcattgttt ttttgaacaa ggttgatttg gttgatgatc ctgagttgct agagctggtg     180

gaagaagagg tgcgtgatgc gcttgctgga tatgggtttt cgcgtgagac gcctatcgtc     240

aaggggtctg cgtttaaagc tctgcaggat ggcgcttccc cggaggatgc agcttgtatt     300

gaggaactgc ttgcggccat ggattcctac tttgaagacc cagtgcgtga cgacgcaaga     360

cctttcttgc tctctatcga ggatgtgtac actatttctg ggcgtggtac cgttgtcacg     420

gggcgcatcg aatgtggggt aattagtctg aatgaagagg tcgagatcgt cgggattaag     480

cccactaaga aaacagtggt tactggcatt gagatgttta ataagttgct tgatcaggga     540

attgcaggtg ataacgtggg gctgcttttg cgcggggtgg ataaaaaaga ggttgagcgc     600

ggtcaggtgc tttctaagcc cggttctatt aagccacaca ccaagtttga ggcgcagatc     660

tacgtgctct ctaaggaaga gggtggccgt cacagtcctt tttttcaagg ttatcgtccg     720

cagttttatt ttagaactac tgacattacc ggtacgattt ctcttcctga aggggtagac     780

atggtgaagc cgggggataa caccaagatt ataggtgagc tcatccaccc gatagctatg     840

gacaagggtc tgaagcttgc gattcgtgaa ggggggcgca ctattgcttc tggt           894
```

```
<210> SEQ ID NO 170
<211> LENGTH: 891
<212> TYPE: DNA
<213> ORGANISM: Ureaplasma urealyticum

<400> SEQUENCE: 170

aatatgatta caggggcagc acaaatggat ggagcaattt tagttattgc tgcatctgat      60

ggggttatgg ctcaaactaa agaacatatt ttattagcac gtcaagttgg tgttccaaaa     120

atcgttgttt tcttaaacaa atgtgatttc atgacagatc cagatatgca agatcttgtt     180

gaaatggaag ttcgtgaatt attatctaaa tatggatttg atggcgataa cacaccagtt     240

attcgtggtt caggtcttaa ggctttagaa ggagatccag tttgagaagc aaaaattgat     300

gaattaatgg acgcagttga ttcatgaatt ccattaccag aacgtagtac tgacaaacca     360

ttcttattag caattgaaga tgtattcaca atttcaggac gtggtacagt agtaactgga     420

cgtgttgaac gtggtgtatt aaaagttaat gatgaggttg aaattgttgg tctaaaagac     480

actcaaaaaa ctgttgttac aggaattgaa atgtttagaa aatcattaga tcaagctgaa     540

gctggtgata atgctggtat tttattacgt ggtattaaaa aagaagatgt tgaacgtggt     600

caagtacttg taaaaccagg atcaattaaa cctcaccgta cttttactgc taaagtttat     660

attcttaaaa aagaagaagg tggacgtcat acacctattg tttcaggata ccgtccacaa     720

ttctatttta gaacaacaga tgtaacaggt gctatttcat tacctgctgg tgttgatttg     780

gttatgccag gtgatgacgt tgaaatgact gtagaattaa ttgctccagt tgcgattgaa     840

gatggatcta aattctcaat ccgtgaaggt ggtaaaactg taggtcatgg t              891
```

```
<210> SEQ ID NO 171
<211> LENGTH: 909
<212> TYPE: DNA
<213> ORGANISM: Wolinella succinogenes

<400> SEQUENCE: 171

aacatgatta caggtgctgc tcaaatggat ggcgcgattc ttgttgtttc tgcggcggat      60

ggccccatgc cccaaactag ggagcacatt cttctttctc gacaagtagg cgttccttac     120
```

-continued

```
atcgtggttt tcttgaacaa agaagatatg gttgatgacg ctgagcttct tgagcttgtt    180

gaaatggaag ttagagaact tcttagcaac tacgacttcc ctggagatga cactcctatc    240

gttgcaggtt ccgctcttaa agctcttgaa gaggctaacg accaggaaaa tgttggcgag    300

tggggcgaga aagtattgaa gcttatggct gaggttgacc gatatattcc tacgcctgag    360

cgagatgtgg ataagccttt ccttatgcct gttgaagacg tattctccat cgcgggtcgt    420

ggaaccgttg tgacaggaag aattgaaaga ggcgtggtta aagtcggtga cgaagtagaa    480

atcgttggta tccgaaacac acaaaaaaca accgtaactg gcgttgagat gttccgaaaa    540

gagctcgaca agggtgaggc gggtgacaac gttggtgttc ttttgagagg caccaagaaa    600

gaagatgttg agagaggtat ggttctttgt aaaataggtt ctatcactcc tcacactaac    660

tttgaaggtg aagtttacgt tctttccaaa gaggaaggcg gacgacacac tccattcttc    720

aatggatacc gacctcagtt ctatgttaga actacagacg ttaccggttc tatctctctt    780

cctgagggcg tagagatggt tatgcctggt gacaacgtta agatcaatgt tgagcttatc    840

gctcctgtag ccctcgaaga gggaacacga ttcgcgatcc gtgaaggtgg tcgaaccgtt    900

ggtgcgggt                                                             909
```

```
<210> SEQ ID NO 172
<211> LENGTH: 26
<212> TYPE: DNA
<213> ORGANISM: Artificial Sequence
<220> FEATURE:
<223> OTHER INFORMATION: synthetic DNA
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (18)
<223> OTHER INFORMATION: i

<400> SEQUENCE: 172

tartcngtra angcytcnac rcacat                                           26


<210> SEQ ID NO 173
<211> LENGTH: 21
<212> TYPE: DNA
<213> ORGANISM: Artificial Sequence
<220> FEATURE:
<223> OTHER INFORMATION: synthetic DNA

<400> SEQUENCE: 173

tctttagcag aacaggatga a                                                21


<210> SEQ ID NO 174
<211> LENGTH: 20
<212> TYPE: DNA
<213> ORGANISM: Artificial Sequence
<220> FEATURE:
<223> OTHER INFORMATION: synthetic DNA

<400> SEQUENCE: 174

gaataattcc atatcctccg                                                  20


<210> SEQ ID NO 175
<211> LENGTH: 54
<212> TYPE: DNA
```

-continued

<213> ORGANISM: Agrobacterium tumefaciens

<400> SEQUENCE: 175
cgactgttac cggcgttgaa atgttccaaa tggttatgcc tggcgacaac gtca 54

<210> SEQ ID NO 176
<211> LENGTH: 54
<212> TYPE: DNA
<213> ORGANISM: Bacillus subtilis

<400> SEQUENCE: 176
caactgttac aggtgttgaa atgttccaaa tggttatgcc tggagataac actg 54

<210> SEQ ID NO 177
<211> LENGTH: 54
<212> TYPE: DNA
<213> ORGANISM: Bacteroides fragiles

<400> SEQUENCE: 177
cagttgtaac aggtgttgaa atgttccaaa tggtaatgcc gggtgataac gtaa 54

<210> SEQ ID NO 178
<211> LENGTH: 54
<212> TYPE: DNA
<213> ORGANISM: Borrelia burgdorferi

<400> SEQUENCE: 178
ctactgttac tggtgttgaa atgttccaaa tggttatgcc tggtgataat gttg 54

<210> SEQ ID NO 179
<211> LENGTH: 54
<212> TYPE: DNA
<213> ORGANISM: Brevibacterium linens

<400> SEQUENCE: 179
cgactgtcac cgctatcgag atgttccaga tggtcatgcc cggcgacacc accg 54

<210> SEQ ID NO 180
<211> LENGTH: 54
<212> TYPE: DNA
<213> ORGANISM: Burkholderia cepacia

<400> SEQUENCE: 180
cgacctgcac gggcgttgaa atgttccaaa tggtcatgcc gggcgacaac gtgt 54

<210> SEQ ID NO 181
<211> LENGTH: 54
<212> TYPE: DNA
<213> ORGANISM: Chlamydia trachomatis

<400> SEQUENCE: 181
cgattgttac tggggttgaa atgttcaaga tggtcatgcc tggggataac gttg 54

<210> SEQ ID NO 182
<211> LENGTH: 54
<212> TYPE: DNA
<213> ORGANISM: Escherichia coli

<400> SEQUENCE: 182
ctacctgtac tggcgttgaa atgttccata tggtaatgcc gggcgacaac atca 54

<210> SEQ ID NO 183
<211> LENGTH: 54
<212> TYPE: DNA

<213> ORGANISM: Fibrobacter succinogenes

<400> SEQUENCE: 183
acgtcatcac cggtgttgaa atgttccaaa tggttactcc gggtgacacg gtca 54

<210> SEQ ID NO 184
<211> LENGTH: 54
<212> TYPE: DNA
<213> ORGANISM: Flavobacterium ferrugineum

<400> SEQUENCE: 184
ctaccgttac aggtgttgag atgttccaaa tggttatgcc tggtgataac acca 54

<210> SEQ ID NO 185
<211> LENGTH: 54
<212> TYPE: DNA
<213> ORGANISM: Haemophilus influenzae

<400> SEQUENCE: 185
ctactgtaac gggtgttgaa atgttccaaa tggtaatgcc aggcgataac atca 54

<210> SEQ ID NO 186
<211> LENGTH: 54
<212> TYPE: DNA
<213> ORGANISM: Helicobacter pylori

<400> SEQUENCE: 186
cgactgtaac cggtgtagaa atgtttaaaa tggttatgcc tggcgataat gtca 54

<210> SEQ ID NO 187
<211> LENGTH: 54
<212> TYPE: DNA
<213> ORGANISM: Micrococcus luteus

<400> SEQUENCE: 187
ccactgtcac cggcatcgag atgttccaga tggtcatgcc cggcgacaac accg 54

<210> SEQ ID NO 188
<211> LENGTH: 54
<212> TYPE: DNA
<213> ORGANISM: Myocbacterium tuberculosis

<400> SEQUENCE: 188
ccaccgtcac cggtgtggag atgttccaga tggtgatgcc cggtgacaac acca 54

<210> SEQ ID NO 189
<211> LENGTH: 54
<212> TYPE: DNA
<213> ORGANISM: Mycoplasma genitalium

<400> SEQUENCE: 189
cagttgttac tggaattgaa atgttcaaaa tggttctacc tggtgataat gctt 54

<210> SEQ ID NO 190
<211> LENGTH: 54
<212> TYPE: DNA
<213> ORGANISM: Neisseria gonorrhoeae

<400> SEQUENCE: 190
ccacctgtac cggcgttgaa atgttccaaa tggtaatgcc gggtgagaac gtaa 54

<210> SEQ ID NO 191
<211> LENGTH: 54
<212> TYPE: DNA

<213> ORGANISM: Rickettsia prowazekii

<400> SEQUENCE: 191
cgacttgtac aggtgtagaa atgttcaaga tggttatgcc tggagataat gcta 54

<210> SEQ ID NO 192
<211> LENGTH: 54
<212> TYPE: DNA
<213> ORGANISM: Salmonellla typhimurium

<400> SEQUENCE: 192
cgacttgtac aggtgtagaa atgttcaaga tggttatgcc tggagacaac atca 54

<210> SEQ ID NO 193
<211> LENGTH: 54
<212> TYPE: DNA
<213> ORGANISM: Shewanella putida

<400> SEQUENCE: 193
caacgtgtca tggtgtagaa atgttccaga tggtaatgcc aggcgataac atca 54

<210> SEQ ID NO 194
<211> LENGTH: 54
<212> TYPE: DNA
<213> ORGANISM: Stigmatella aurantiaca

<400> SEQUENCE: 194
cggtcatcac gggggtggag atgttccaga tggtgatgcc gggagacaac atcg 54

<210> SEQ ID NO 195
<211> LENGTH: 54
<212> TYPE: DNA
<213> ORGANISM: Streptococcus pyogenes

<400> SEQUENCE: 195
ctgttgttac tggtgttgaa atgttccaaa tggttatgcc tggtgataac gtga 54

<210> SEQ ID NO 196
<211> LENGTH: 54
<212> TYPE: DNA
<213> ORGANISM: Thiobacillus cuprinus

<400> SEQUENCE: 196
ccacctgcac cggcgtggaa atgttcaaaa tggtcatgcc cggcgataat gtga 54

<210> SEQ ID NO 197
<211> LENGTH: 54
<212> TYPE: DNA
<213> ORGANISM: Treponema pallidum

<400> SEQUENCE: 197
cagtggttac tggcattgag atgtttaaca tggtgaagcc gggggataac acca 54

<210> SEQ ID NO 198
<211> LENGTH: 54
<212> TYPE: DNA
<213> ORGANISM: Ureaplasma urealyticum

<400> SEQUENCE: 198
ctgttgttac aggaattgaa atgtttaatt tggttatgcc aggtgatgac gttg 54

<210> SEQ ID NO 199
<211> LENGTH: 54
<212> TYPE: DNA

<213> ORGANISM: Wolniella succinogenes

<400> SEQUENCE: 199
caaccgtaac tggcgttgag atgttccaga tggttatgcc tggtgacaac gtta 54

<210> SEQ ID NO 200
<211> LENGTH: 54
<212> TYPE: DNA
<213> ORGANISM: Schizosacchharomyces pombe

<400> SEQUENCE: 200
gtgtcactac cgaagtcaag tctgttgaga agattgagga gtcccctaag tttg 54

<210> SEQ ID NO 201
<211> LENGTH: 54
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 201
tgacaggcat tgagatgttc cacaagaaga aggagcttgc catgcccggg gagg 54

<210> SEQ ID NO 202
<211> LENGTH: 54
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 202
tgacaggcat tgagatgttc cacaagaaga aggagcttgc catgcccggg gagg 54

<210> SEQ ID NO 203
<211> LENGTH: 70
<212> TYPE: DNA
<213> ORGANISM: Bordetella pertussis

<400> SEQUENCE: 203
ctcgagatca ccgacgcgct ggtgcgctcg ggctcggccc gcctgatgag ccaggcgctg 60
cgcaagctga 70

<210> SEQ ID NO 204
<211> LENGTH: 70
<212> TYPE: DNA
<213> ORGANISM: Burholderia cepacia

<400> SEQUENCE: 204
ctcgaaatca ccgatgcgct ggtgcgctcg ggctcggccc gcctgatgtc gcaggcgctg 60
cgcaagctga 70

<210> SEQ ID NO 205
<211> LENGTH: 70
<212> TYPE: DNA
<213> ORGANISM: Campylobacter jejuni

<400> SEQUENCE: 205
ttagaaattg tagaaactat agcaagaagt ggcgcagcaa gacttatgtc tcaagctcta 60
agaaaactta 70

<210> SEQ ID NO 206
<211> LENGTH: 70
<212> TYPE: DNA

<213> ORGANISM: Chamydia trachomatis

<400> SEQUENCE: 206
ttgagtattg cagagctctt agcgcgttct ggacgagctc gcatgatgtc gcaggctcta 60
cgcaaattaa 70

<210> SEQ ID NO 207
<211> LENGTH: 70
<212> TYPE: DNA
<213> ORGANISM: Clostridium perfringens

<400> SEQUENCE: 207
ttagaaataa cagaagcttt agttagatca ggagcagcta gattaatgtc acaagcctta 60
agaaagttaa 70

<210> SEQ ID NO 208
<211> LENGTH: 70
<212> TYPE: DNA
<213> ORGANISM: Corynebacterium pseudotuberculosis

<400> SEQUENCE: 208
ctggagattg cagatatgct tgttcgctct ggagcagcgc gtttgatgag tcaggcgctg 60
cgtaagcttg 70

<210> SEQ ID NO 209
<211> LENGTH: 70
<212> TYPE: DNA
<213> ORGANISM: Enterobacterium agglomerans

<400> SEQUENCE: 209
ctggaaatct gtgatgcgct gacccgttca ggcgcagctc gtatgatgag ccaggcgatg 60
cgtaagcttg 70

<210> SEQ ID NO 210
<211> LENGTH: 70
<212> TYPE: DNA
<213> ORGANISM: Enterococcus faecium

<400> SEQUENCE: 210
ttagagattg ccgatgcctt agtttcaagt ggtgcagctc gactaatgtc tcaagcacta 60
cgtaaattat 70

<210> SEQ ID NO 211
<211> LENGTH: 70
<212> TYPE: DNA
<213> ORGANISM: Escherichia coli

<400> SEQUENCE: 211
ctggaaatct gtgacgccct ggcgcgttct ggcgcggcac gtatgatgag ccaggcgatg 60
cgtaagctgg 70

<210> SEQ ID NO 212
<211> LENGTH: 70
<212> TYPE: DNA
<213> ORGANISM: Haemophilus influenzae

<400> SEQUENCE: 212
gcgaacagaa gaatagaatt ttaatgcatt accgcgacct gtgagtttac gcaaagcttg 60
agacattaaa 70

<210> SEQ ID NO 213
<211> LENGTH: 70
<212> TYPE: DNA
<213> ORGANISM: Helicobacter pylori

<400> SEQUENCE: 213
ttagaaattt tagaaacgat caccagaagc ggaggagcaa ggcttatgag ccatgcgtta 60
agaaaaatca 70

<210> SEQ ID NO 214
<211> LENGTH: 70
<212> TYPE: DNA
<213> ORGANISM: Lactococcus lactis

<400> SEQUENCE: 214
cttcaaattg ctgaaaaatt gattacttct ggagcagcac gtatgatgtc acaagccatg 60
cgtaaacttg 70

<210> SEQ ID NO 215
<211> LENGTH: 70
<212> TYPE: DNA
<213> ORGANISM: Legionella pneumophila

<400> SEQUENCE: 215
ctggaaatta ctgatatgct ggtgcgttct gcagcggcaa gattgatgtc gcaagccctg 60
cgtaaattga 70

<210> SEQ ID NO 216
<211> LENGTH: 70
<212> TYPE: DNA
<213> ORGANISM: Mycoplasma gentalium

<400> SEQUENCE: 216
tttgctctta tcgaatcatt aattaaaaca aacaatgcaa gaatgatgtc aaaaggtttg 60
cgaagaatac 70

<210> SEQ ID NO 217
<211> LENGTH: 70
<212> TYPE: DNA
<213> ORGANISM: Proteus mirabilis

<400> SEQUENCE: 217
ctggaaattt gtgatgcatt atctcgctct ggtgccgcac gtatgatgag ccaagctatg 60
cgtaaactag 70

<210> SEQ ID NO 218
<211> LENGTH: 70
<212> TYPE: DNA
<213> ORGANISM: Pseudomonas aeruginosa

<400> SEQUENCE: 218
ctggaaatca ccgacatgct ggtgcgctcc aacgcggcac gcctgatgtc ccaggcgctg 60
cgcaagatca 70

<210> SEQ ID NO 219
<211> LENGTH: 70
<212> TYPE: DNA
<213> ORGANISM: Serratia Marcescens

<400> SEQUENCE: 219

-continued ctggaaatct gtgatgcgct gacccgctcc ggcgcggcgc gcatgatgag ccaggcgatg 60
cgtaagctgg 70

<210> SEQ ID NO 220
<211> LENGTH: 70
<212> TYPE: DNA
<213> ORGANISM: Shigella flexneri

<400> SEQUENCE: 220
ctggaaatct gtgacgccct ggcgcgttct ggcgcggcac gtatgatgag ccaggcgatg 60
cgtaagctgg 70

<210> SEQ ID NO 221
<211> LENGTH: 70
<212> TYPE: DNA
<213> ORGANISM: Staphylococcus aureus

<400> SEQUENCE: 221
cttgaaatcg ccgaagcatt tgttagaagt ggtgcagctc gtttaatgtc acaagcgtta 60
cgtaaacttt 70

<210> SEQ ID NO 222
<211> LENGTH: 70
<212> TYPE: DNA
<213> ORGANISM: Vibrio cholerae

<400> SEQUENCE: 222
ctggaaattt gtgatgcact ggctcgctct ggtgcagcgc gtatgttgtc gcaagcaatg 60
cgtaaactga 70

<210> SEQ ID NO 223
<211> LENGTH: 70
<212> TYPE: DNA
<213> ORGANISM: Yersinia pestis

<400> SEQUENCE: 223
ctggaaattt gtgatgcgct gactcgctct ggtgccgcgc gtatgatgag ccaggctatg 60
cgtaagctgg 70

<210> SEQ ID NO 224
<211> LENGTH: 44
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 224
gaaattgcag gaaattgatt gaatgatgag tcagccatgc gtaa 44

<210> SEQ ID NO 225
<211> LENGTH: 23
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: 3, 6, 9, 12, 15
<223> OTHER INFORMATION: n = inosine
<220> FEATURE:
<221> NAME/KEY: misc_feature
<222> LOCATION: 4, 5
<223> OTHER INFORMATION: k = t or g
<220> FEATURE:

-continued

```
<221> NAME/KEY: misc_feature
<222> LOCATION: 18
<223> OTHER INFORMATION: r = a or g

<400> SEQUENCE: 225

acnkknacng gngtngarat gtt                                              23


<210> SEQ ID NO 226
<211> LENGTH: 23
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: 6, 9, 12, 18
<223> OTHER INFORMATION: n = inosine
<220> FEATURE:
<221> NAME/KEY: misc_feature
<222> LOCATION: 3
<223> OTHER INFORMATION: r = a or g
<220> FEATURE:
<221> NAME/KEY: misc_feature
<222> LOCATION: 2
<223> OTHER INFORMATION: y = c or t

<400> SEQUENCE: 226

ayrttntcnc cnggcatnac cat                                              23
```